US011459336B2

(12) United States Patent
Gelin

(10) Patent No.: US 11,459,336 B2
(45) Date of Patent: Oct. 4, 2022

(54) PYRAZINE CARBAMATES AND THEIR USE AS GLUN2B RECEPTOR MODULATORS

(71) Applicant: JANSSEN PHARMACEUTICA NV, Beerse (BE)

(72) Inventor: Christine Gelin, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 168 days.

(21) Appl. No.: 16/899,817

(22) Filed: Jun. 12, 2020

(65) Prior Publication Data

US 2020/0392155 A1    Dec. 17, 2020

Related U.S. Application Data

(60) Provisional application No. 62/861,642, filed on Jun. 14, 2019.

(51) Int. Cl.
| | |
|---|---|
| *C07D 498/10* | (2006.01) |
| *A61P 25/18* | (2006.01) |
| *A61P 25/24* | (2006.01) |
| *A61P 25/08* | (2006.01) |
| *C07D 413/06* | (2006.01) |
| *C07D 413/14* | (2006.01) |

(52) U.S. Cl.
CPC ............ *C07D 498/10* (2013.01); *A61P 25/08* (2018.01); *A61P 25/18* (2018.01); *A61P 25/24* (2018.01); *C07D 413/06* (2013.01); *C07D 413/14* (2013.01)

(58) Field of Classification Search
CPC .. C07D 498/10; C07D 413/06; C07D 413/14; A61P 25/08; A61P 25/18; A61P 25/24; A61P 25/00; A61K 31/497; A61K 31/5355
See application file for complete search history.

(56) References Cited

U.S. PATENT DOCUMENTS

| | | |
|---|---|---|
| 7,622,486 B2 | 11/2009 | Pal et al. |
| 8,765,784 B2 | 7/2014 | Arrington et al. |
| 8,785,438 B2 | 7/2014 | Ohtsuka et al. |
| 8,877,772 B2 | 11/2014 | Gelbard et al. |
| 8,987,473 B2 | 3/2015 | Nagai et al. |
| 9,174,993 B2 | 11/2015 | Nazare et al. |
| 9,434,743 B2 | 9/2016 | Cheruvallath et al. |
| 9,963,447 B2 | 5/2018 | Chrovian et al. |
| 9,981,950 B2 | 5/2018 | Schindler et al. |
| 10,071,988 B2 | 9/2018 | Chen et al. |
| 10,155,727 B2 | 12/2018 | Schindler et al. |
| 10,233,173 B2 | 3/2019 | Chen et al. |
| 10,323,021 B2 | 6/2019 | Schindler et al. |
| 10,377,753 B2 | 8/2019 | Chrovian et al. |
| 10,617,676 B2 | 4/2020 | Chrovian et al. |
| 2007/0275965 A1 | 11/2007 | Thomas et al. |
| 2008/0300239 A1 | 12/2008 | Adams et al. |
| 2011/0130384 A1 | 6/2011 | Setoh et al. |
| 2014/0275011 A1 | 9/2014 | Mastracchio et al. |
| 2015/0210681 A1 | 7/2015 | Bourque et al. |
| 2016/0024087 A1 | 1/2016 | Gelbard et al. |
| 2018/0125826 A1 | 5/2018 | Chrovian et al. |
| 2018/0208595 A1 | 7/2018 | Chrovian et al. |
| 2018/0282305 A1 | 10/2018 | Schindler et al. |
| 2018/0334451 A1 | 11/2018 | Chen et al. |
| 2019/0135791 A1 | 5/2019 | Chen et al. |
| 2019/0308950 A1 | 10/2019 | Ziff et al. |
| 2020/0392113 A1 | 12/2020 | Dvorak et al. |
| 2020/0392130 A1 | 12/2020 | Hiscox et al. |
| 2020/0392154 A1 | 12/2020 | Gelin et al. |
| 2021/0017168 A1 | 1/2021 | Hiscox et al. |
| 2021/0017169 A1 | 1/2021 | Hiscox et al. |

FOREIGN PATENT DOCUMENTS

| | | |
|---|---|---|
| CN | 110294756 A | 10/2019 |
| EP | 928789 A1 | 7/1999 |
| EP | 2194045 A1 | 6/2010 |
| JP | 2004-501901 A1 | 1/2001 |
| JP | 2012-188363 A | 4/2012 |
| WO | 1995028400 A1 | 10/1995 |
| WO | 2002060877 A1 | 8/2002 |
| WO | 2003082868 A1 | 10/2003 |
| WO | 2003097637 A1 | 11/2003 |
| WO | 2003/101968 A1 | 12/2003 |
| WO | 2005080379 A1 | 9/2005 |
| WO | 2008145616 A1 | 12/2008 |
| WO | 2009004430 A1 | 1/2009 |
| WO | 2009058261 A1 | 5/2009 |
| WO | 2009118187 A1 | 10/2009 |
| WO | 2009/157196 A1 | 12/2009 |
| WO | 2010043396 A1 | 4/2010 |
| WO | 2010108187 A1 | 9/2010 |

(Continued)

OTHER PUBLICATIONS

International Search Report and Written Opinion of the International Searching Authority for International Application No. PCT/EP2020/066400, dated Jul. 28, 2020.
International Search Report and Written Opinion of the International Searching Authority for International Application No. PCT/EP2020/066392, dated Sep. 21, 2020.
International Search Report and Written Opinion of the International Searching Authority for International Application No. PCT/EP2020/066384, dated Jul. 28, 2020.
International Search Report and Written Opinion of the International Searching Authority for International Application No. PCT/EP2020/066391, dated Jul. 29, 2020.

(Continued)

*Primary Examiner* — Robert H Havlin
(74) *Attorney, Agent, or Firm* — Biospark Intellectual Property Law

(57) ABSTRACT

Pyridine carbamates, pharmaceutical compositions containing pyridine carbamates, and uses of the pyridine carbamates and pharmaceutical compositions for modulating GluN2B receptors and for treating diseases, disorders, and medical conditions mediated by GluN2B receptor activity.

32 Claims, No Drawings

(56) References Cited

FOREIGN PATENT DOCUMENTS

| WO | 2011/022348 A1 | 2/2011 |
|---|---|---|
| WO | 2011140202 A2 | 11/2011 |
| WO | 2013060029 A1 | 5/2013 |
| WO | 2013130855 A1 | 9/2013 |
| WO | 2014124651 A1 | 8/2014 |
| WO | 2014145051 A1 | 9/2014 |
| WO | 2015002754 A2 | 1/2015 |
| WO | 2015017502 A1 | 2/2015 |
| WO | 2016025917 A1 | 2/2016 |
| WO | 2016081649 A1 | 5/2016 |
| WO | 2016/150971 A1 | 9/2016 |
| WO | 2017/007938 | 1/2017 |
| WO | 2018/067786 | 4/2018 |
| WO | 2018/231745 A1 | 12/2018 |
| WO | 2020/249785 A1 | 12/2020 |
| WO | 2020/249791 A1 | 12/2020 |
| WO | 2020/249792 A1 | 12/2020 |
| WO | 2020/249796 A1 | 12/2020 |
| WO | 2020/249799 A1 | 12/2020 |
| WO | 2020/249802 A1 | 12/2020 |

OTHER PUBLICATIONS

International Search Report and Written Opinion of the International Searching Authority for International Application No. PCT/EP2020/066405, dated Jul. 29, 2020.

First Examination Report dated Nov. 30, 2020 in connection with European application No. 17859165.7.

Iadarola et al., 2015 Therapeutic Advances in Chronic Disease, vol. 6 (3), p. 97-114.

Machado-Vieira et al., 2017, "New Targets for Rapid Antidepressant Action" Prog. Neurobiol. 152-21-37.

Sun et al., 2020 "Synthesis and preliminary evaluation of novel C-labled GluN2B-selective NMDA receptor negative allosteric modulators" Acta Pharmacologica Sinica, pp. 1-8.

Davies et al., 2012, "A novel series of benzimidazole NR2B-selective NMDA receptor antagonists," Bioorganic & Medicinal Chemistry Letters 22:2620-2623.

Layton et al., 2006, "Recent Advances in the Development of NR2B Subtype-Selective NMDA Receptor Antagonist," Current Topics in Medicinal Chemistry 6:697-709.

Mao et al., 2014, "Phosphorylation and regulation of glutamate receptors by CaMKII," Acta Physiologica Sinica 66(3):365-372.

Pratap et al., 2007, "Guanidine and amidine mediated synthesis of bridgehead triazaphenalenes, pyrimidines and pyridines through domino reactions," Tetrahedron Letters 48:5845-5849.

Vippagunta et al., 2001, "Crystalline Solids" Advanced Drug Delivery Reviews 48:3-26.

International Search Report and Written Opinion of the International Searching Authority for International Application No. PCT/EP2020/066396, dated Jul. 28, 2020.

International Search Report and Written Opinion of the International Searching Authority for International Application No. PCT/US2015/045412, dated Nov. 10, 2015.

International Search Report and Written Opinion of the International Searching Authority for International Application No. PCT/US2015/045413, dated Nov. 27, 2015.

International Search Report and Written Opinion of the International Searching Authority for International Application No. PCT/US2016/041339 dated Sep. 27, 2016.

International Search Report and Written Opinion of the International Searching Authority for International Application No. PCT/US2017/017093, dated Apr. 7, 2017.

International Search Report and Written Opinion of the International Searching Authority issued in connection with PCT/US2017/055278, dated Mar. 9, 2018.

International Search Report and Written Opinion of the International Searching Authority for International Application No. PCT/IB2019/052731, dated Nov. 1, 2019.

Addy, et al., Single-Dc3e Administration of MK-0657, an N112B-Selective NMDA Antagonist, Does Not Result in Clinically Meaningful Improvement in Motor Function in Patients 127ith Moderate Parkinson's Disease, Journal of Clinical Pharmacology, 2009, pp. 856-864, vol. 49.

Andreas Straube., Pharmacology of vertigo/nystagmus/oscillopsia, Current Opinion in Neurology, 2005, pp. 11-14, vol. 18 Issue 1.

Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 Issue 2.

Bagshawe, Kenneth D., 1995, "Antibody-Directed Enzyme prodrug Therapy : A Review," Drug Development Research, 34:220-230.

Berberich, et al., The role of NMDAR subtypes and charge transfer during hippocampal LTP induction, Neuropharmacology, 2007, pp. 77-86, vol. 52 Issue 1.

Berge, et al., Pharmaceutical Salts, Journal of Pharmaceutical Sciences, 1977, pp. 1-19, vol. 66, No. 1.

Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.

Bodor, Nicholas, 1984, "Novel Approaches to the Design of Safer Drugs: Soft Drugs and Site-Specific Chemical Delivery Systems," Advances in Drug Research, 13:256-331.

Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.

Buonarati, et al., Role of sulfation and acetylation in the activation of 2-hydroxyamino-1-methyl-6-phenylimidazo[4,5-b]pyridine to intermediates which bind DNA, Mutation Research, Jun. 21, 1990, pp. 185-190, vol. 245.

Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.

Chrovian, et al., "1H-Pyrrolo[3,2-b]pyridine GluN2B-Selective Negative Allosteric Modulators", ACS Med. Chem. Lett, 2019, vol. 10, pp. 261-266.

Chemical Abstract Service (CAS), Database Registry [Online], Database Registry [Online], STN Sep. 18, 2012, pp. 1-1, Database Accession No. 1394745_67_5.

Collingridge, et al., "A nomenclature for ligand-gated ion channels" Neuropharmacology, 2009, vol. 56, pp. 2-5.

Cull-Candy, et al., NMDA receptor subunits: diversity, development and disease, Current Opinion in Neurobiology, 2001, pp. 327-335, vol. 11 Issue 3.

Dalmau, et al., Anti-NMDA-receptor encephalitis: case series and analysis of the eff ects of antibodies, Lancet Neurol, Dec. 2008, pp. 1091-1098, vol. 7 Issue 12.

Dorval, et al., Association of the glutamate receptor subunit gene GRIN2B with attention-deficit/hyperactivity disorder, Genes, Brain and Behavior, 2007, pp. 444-452, vol. 6 Issue 5.

Duty, Susan, 2012, "Targeting Glutamate Receptors to Tackle the Pathogenesis, Clinical Symptoms and Levodopa-Induced Dyskinesia Associated with Parkinson's Disease," CNS Drugs, 26(12):1017-1032.

Farjam, et al., Inhibition of NR2B-Containing N-methyl-D-Aspartate Receptors (NMDARs) in Experimental Autoimmune Encephalomyelitis, a Model of Multiple Sclerosis, Iranian Journal of Pharmaceutical Research, 2014, pp. 695-705, vol. 13 Issue 2.

Fleisher, et al., Improved oral drug delivery: solubility limitations overcome by the use of prodrugs, Advanced Drug Delivery Reviews, 1996, pp. 115-130, vol. 19.

Fuller, et al., Differential expression of the NMDA NR2B receptor subunit in motoneuron populations susceptible and resistant to amyotrophic lateral sclerosis, Neuroscience Letters, Jan. 26, 2006, pp. 157-161, vol. 399 Issue (1-2).

Glenn D. Considine, Van Nostrand's Encyclopedia of Chemistry,, Encyclopedia of Chemistry, 2005, pp. 261, Chapter 5.

(56) References Cited

OTHER PUBLICATIONS

Grasselli, et al., Abnormal NMDA receptor function exacerbates experimental autoimmune encephalomyelitis, British Journal of Pharmacology, 2013, pp. 502-517, vol. 168 Issue 2.
Grimwood, et al., NR2B-containing NMDA receptors are upregulated in temporal cortex in schizophrenia, NeuroReport, Feb. 25, 1999, pp. 461-465, vol. 10 Issue 3.
Guitton, et al., Blockade of Cochlear NMDA Receptors Prevents Long-Term Tinnitus during a Brief Consolidation Window after Acoustic Trauma, Neural Plasticity, Dec. 12, 2007, pp. 1-11, Article ID 80904.
Haller, et al., NR2B subunit-specific NMDA antagonist Ro25-6981 inhibits the expression of conditioned fear: a comparison with the NMDA antagonist MK-801 and fluoxetine, Behavioural Pharmacology, 2011, pp. 113-121, vol. 22 Issue 2.
Hanson, et al., Altered GluN2B NMDA receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Houston, et al., "Methods for Predicting In Vivo Pharmacokinetics Using Data from In Vitro Assays" Current Drug Metabolism, 2008, vol. 9, pp. 940-951.
Ito, et al., A Medium-term rat liver bioassay for rapid in vivo detection of carcinogenic potential of chemicals, Cancer Sci, 2003, pp. 3-8, vol. 94 Issue 1.
Jozsef Nagy, The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kamalesh B. Ruppa et al., Chapter 7: NMDA Antagonists of GluN2B Subtype and Modulators of GluN2A, GluN2C, and GluN2D Subtypes—Recent Results and Developments, Annual Reports in Medicinal Chemistry, Jan. 1, 2012, pp. 89-103, vol. 47.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.
Layton, et al., Discovery of 5-aryl-1,3-dihydro-2H-imidazo[4,5-b]pyridin-2-ones as positive allosteric modulators of metabotropic glutamate subtype-2(mGlu2) receptors with efficacy in a preclinical model of psychosis, Bioorganic & Medicinal Chemistry Letters, Feb. 15, 2016, pp. 1260-1264, vol. 26.
Leaderbrand, et al., Co-activation of NR2A and NR2B subunits induces resistance to fear extinction, Neurobiol Learn Mem, 2013, pp. 35-40, vol. 113.
Leaver, et al., Neuroprotective Effects of a Selective N-Methyl-d-Aspartate NR2B Receptor Antagonist in the 6-Hydroxydopamine Rat Model of Parkinson's Disease, Clinical and Experimental Pharmacology and Physiology, May 27, 2008, pp. 1388-1394, vol. 35 Issue 11.
Leyva, et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.
Li, et al., Enhanced Striatal NR2B-Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B-Containing NMDA Receptors, The Journal of Neuroscience, May 4, 2011, pp. 6627-6638, vol. 31 Issue 18.
Lima-Ojeda, et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Martucci, et al., N-methyl-d-aspartate receptor NR2B subunit gene GRIN2B in schizophrenia and bipolar disorder: Polymorphisms and mRNA levels, Schizophrenia Research, Mar. 20, 2006, pp. 214-221, vol. 84 Issue (2-3).
Massey, et al., Differential Roles of NR2A and NR2B-Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B-containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp. 12-19, vol. 100 Issue (1-2).
Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.
Orgogozo, et al., Efficacy and Safety of Memantine in Patients With Mild to Moderate Vascular Dementia A Randomized, Placebo-Controlled Trial (MMM 300), Stroke, 2002, pp. 1834-1839, vol. 33.
Paoletti, et al., NMDA receptor subunit diversity: impact on receptor properties, synaptic plasticity and disease, Nature Reviews | Neuroscience, 2013, pp. 383-400, vol. 14 Issue 6.
Park et al. "Metabolism of Fluorine-containing drugs", Annu. Rev. Pharmacol. Toxicol. 2001. vol. 41, pp. 443-470, entire document.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.
Porsolt, et al., Behavioural Despair in Mice: A Primary Screening Test for Antidepressants, Arch int Pharmacodyn, 1977, pp. 327-336, vol. 229.
Preskorn, et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology, Dec. 2008, pp. 631-637, vol. 28 Issue 6.
PubChem-CID-90046926, Create Date: Feb. 13, 2015 (Feb. 13, 2015), entire document.
Remington, Remington Pharmaceutical Sciences., Pharmaceutical Sciences., 1985, pp. 1418, vol. 76.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Shan, et al., Prodrug Strategies Based on Intramolecular Cyclization Reactions, Journal of Pharmaceutical Sciences, Jul. 1997, pp. 765-767, vol. 86 Issue 7.
Shen, et al., Heroin relapse requires long-term potentiation-like plasticity mediated by NMDA2b-containing receptors, PNAS, Nov. 29, 2011, pp. 19407-19412, vol. 108 Issue 48.

(56) References Cited

OTHER PUBLICATIONS

Starck, et al., Drug therapy for acquired pendular nystagmus in multiple sclerosis, J Neurol, 1997, pp. 9-16, vol. 244 Issue 1.

Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.

STN Registry database entry for CAS RN 1394745-67-5, entered STN Sep. 18, 2012, Accessed Sep. 8, 2017.

STN Registry database entry for CAS RN 1493474-46-6, 1491341-24-2, 1479235-62-5, and 1477636-42-2, Accessed Apr. 10, 2019.

Tang, et al., 2005, "Disturbed Ca2+ signaling and apoptosis of medium spiny neurons in Huntington's disease," PNAS, 102(7):2602-2607.

Tang, et al., Genetic enchancement of learning and memory in mice, Nature, Sep. 2, 1999, pp. 63-69, vol. 401 Issue 6748.

Traynelis, et al., Glutamate Receptor Ion Channels: Structure, Regulation, and Function, Pharmacol Rev, 2010, pp. 405-496, vol. 62 Issue 3.

Wang, et al., Targeting the NMDA receptor subunit NR2B for treating or preventing age-related memory decline, Expert Opin. Ther. Targets, 2014, pp. 1121-1130, vol. 18 Issue 10.

Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.

Weickert, et al., Molecular evidence of N-methyl-D-aspartate receptor hypofunction in schizophrenia, Molecular Psychiatry, 2013, pp. 1185-1192, vol. 18.

Won, et al., Autistic-like social behaviour in Shank2-mutant mice improved by restoringNMDA receptor function, Nature, Jun. 14, 2012, pp. 261-265, vol. 486.

Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.

Youssif, S. "Recent trends in the chemistry of pyridine N-oxides" Arkivoc, 2001, pp. 242-268.

Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.

Zarate, et al., A Randomized Trail of an N-methyl_D-aspartate Antagonist in Treatment-Resistant Major Depression, Arch Gen Psychiatry, 2006, pp. 856-864, vol. 63.

PYRAZINE CARBAMATES AND THEIR USE AS GLUN2B RECEPTOR MODULATORS

1. CROSS-REFERENCE TO RELATED APPLICATIONS

This application claims the priority benefit of U.S. provisional application No. 62/861,642, filed Jun. 14, 2019, the contents of which are incorporated herein in their entireties by reference thereto.

2. BACKGROUND

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluN2B subunits (also known as NR2B; see, Collingridge, et al, *Neuropharmacology*, 2009, 56:2-5) play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res,* 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskorn S H et al. *J Clin Psychopharmacol.* 2008; 28(6):631-7) and other mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. *Stroke* 2002, 33: 1834-1839), Parkinson's disease (Duty S, CNS Drugs. 2012; 26(12):1017-32; Steece-Collier K et al., *Exp Neurol.* 2000; 163(1):239-43; Leaver K R et al. *Clin Exp Pharmacol Physiol.* 2008; 35(11):1388-94), Huntington's chorea (Tang T S et al., *Proc Natl Acad Sci USA.* 2005; 102(7):2602-7; Li L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014; 18(10):1121-30), head injury (Bullock M R et al., *Ann NY Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2):12-9), movement disorders (e.g. dyskinesias) (Morissette M et al., *Mov Disord.* 2006; 21(1):9-17), various neurodegenerative diseases (e.g. amyotrophic lateral sclerosis (Fuller P I et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, *Neurotherapeutics.* 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, Neural Plast. 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1):11-4; Starck M et al. *J Neurol.* 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79; Shen H et al., *Proc Natl Acad Sci USA.* 2011; 108(48):19407-12).

In view of the clinical importance of GluN2B, the identification of compounds that modulate GluN2B receptor function represents an attractive avenue into the development of new therapeutic agents. Such compounds are provided herein.

3. SUMMARY

In one aspect, this disclosure provides compounds of Formula (I):

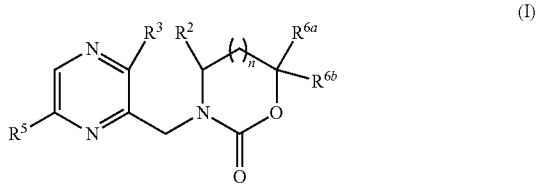

and pharmaceutically acceptable salts, solvates, isotopic variants, and N-oxides thereof, wherein:

n is 0 or 1;
$R^2$ is H or alkyl;
$R^3$ is H or alkyl;
$R^5$ is aryl which is optionally substituted with one or two substituents each of which is independently halogen, haloalkyl, or O-haloalkyl; and
$R^{6a}$ and $R^{6b}$ are, are, each independent from the other, H or alkyl which is optionally substituted with (=O) and a heterocycloalkyl, —NHCH$_3$, or —N(CH$_3$)$_2$; or $R^{6a}$ and $R^{6b}$ together with the carbon atom to which they are attached form (i) a cycloalkyl ring or (ii) a heterocycloalkyl ring which is optionally substituted with alkyl.

In certain embodiments, the compounds of Formula (I) are compounds selected from those species described or exemplified in the detailed description below.

In another aspect, the disclosure provides pharmaceutically acceptable prodrugs of compounds of Formula (I) and pharmaceutically active metabolites of compounds of Formula (I).

In a further aspect, the disclosure provides enantiomers and diastereomers of the compounds of Formula (I), as well as the pharmaceutically acceptable salts, solvates, isotopic variants, N-oxides, pharmaceutically acceptable prodrugs and pharmaceutically active metabolites of compounds of such enantiomers and diastereomers.

Exemplary features of the compounds of the disclosure (which include, for example, compounds of Formula (I), salts of compounds of Formula (I), solvates of compounds of Formula (I), isotopic variants of compounds of Formula (I), N-oxides of compounds of Formula (I), prodrugs of compounds of Formula (I), metabolites of compounds of Formula (I), enantiomers and diastereomers of compounds of Formula (I) etc.), are described in Section 4.3 and numbered embodiments, 1 to 84, infra.

In another aspect, the disclosure provides pharmaceutical compositions comprising a compound of the disclosure. Such pharmaceutical compositions can be used, for example, for treating a disease, disorder, or medical condition mediated by GluN2B receptor activity. In some embodiments, a pharmaceutical composition of the disclosure comprises at least one compound selected from compounds of Formula (I), pharmaceutically acceptable salts of compounds of Formula (I), solvates of compounds of Formula (I), isotopic variants of compounds of Formula (I), and N-oxides of compounds of Formula (I). Pharmaceutical compositions of the disclosure typically comprise one or more pharmaceutically acceptable excipients. Exemplary features of pharmaceutical compositions of the disclosure are described in Section 4.4 and numbered embodiments 85 to 91, infra.

In another aspect, the disclosure is directed to a method for modulating GluN2B receptor activity, including when such receptor is in a subject, comprising exposing GluN2B receptors to an effective amount of at least one compound of the disclosure (e.g., at least one compound selected from compounds of Formula (I), pharmaceutically acceptable salts of compounds of Formula (I), solvates of compounds of Formula (I), isotopic variants of compounds of Formula (I), and N-oxides of compounds of Formula (I)). In some aspects, the disclosure is directed to a method of treating a subject suffering from, or diagnosed with a disease, disorder, or medical condition mediated by GluN2B receptor activity, comprising administering to the subject an effective amount of at least one compound of the disclosure (e.g., at least one compound selected from compounds of Formula (I), pharmaceutically acceptable salts of compounds of Formula (I), solvates of compounds of Formula (I), isotopic variants of compounds of Formula (I), and N-oxides of compounds of Formula (I)). Exemplary features of methods for using compounds of the disclosure to treat diseases, disorders, and medical conditions mediated by GluN2B receptor activity are described in Section 4.5 and numbered embodiments 92 to 103, infra.

Additional aspects of this disclosure include methods of making compounds of the disclosure. Exemplary methods for making compounds of the disclosure are described in Sections 4.3 and 4.6.

4. DETAILED DESCRIPTION

In various aspects, this disclosure provides compounds, for example compounds of Formula (I) as described in the Summary and Section 4.3, pharmaceutical compositions comprising at least one compound of the disclosure, for example, as described in Section 4.4, methods of using the compounds of the disclosure, for example, as described in Section 4.5, and methods of making compounds of the disclosure, for example as described in Section 4.6.

4.1. Definitions

Abbreviations, acronyms, and trademarks used in this disclosure include the following:

TABLE 1

| Term | Acronym/Abbreviation/Trademark |
|---|---|
| [1,1'-bis(diphenylphosphino)ferrocene] dichloropalladium(II) | Pd(dppf)Cl$_2$ |
| [1,1'-bis(diphenylphosphino)ferrocene] dichloropalladium(II), complex with dichloromethane | Pd(dppf)Cl$_2$•CH$_2$Cl$_2$ |
| [1,1'-Bis(di-tert-butylphosphino)ferrocene]dichloropalladium(II) | PdCl2(dtbpf) |
| Dichlorobis(triphenylphosphine)palladium(II), Palladium(II)bis(triphenylphosphine) dichloride | Pd(PPh$_3$)Cl$_2$ |
| Acetonitrile | ACN, MeCN |
| Aqueous | aq |

TABLE 1-continued

| Term | Acronym/Abbreviation/Trademark |
| --- | --- |
| Broad | br |
| Cesium carbonate | $Cs_2CO_3$ |
| Diatomaceous Earth | Celite ® 545, Celite ® |
| 1,1'-Carbonyl-diimidazole | CDI |
| (Diethylamino)sulfur trifluoride | DAST |
| Dichlorethane | DCE |
| Methylene chloride, dichloromethane | DCM |
| Bis(2-methoxyethyl)aminosulfur trifluoride | Deoxo-Fluor ® |
| N,N-Diisopropylethylamine, Hunig's base | DIPEA |
| N,N-Dimethylformamide | DMF |
| Deutero-dimethyl sulfoxide | $DMSO-d_6-d_6$ |
| Diphenyl phosphoryl azide | DPPA |
| Electrospray Ionization | ESI |
| Diethyl ether | $Et_2O$ |
| Ethyl Acetate | EtOAc, or EA, or AcOEt |
| Ethanol | EtOH |
| Flash Column Chromatography | FCC |
| Grams | g |
| 1-[Bis(dimethylamino)methylene]-1H-1,2,3-triazolo[4,5-b]pyridinium 3-oxide hexafluorophosphate | HATU |
| Hours | h |
| High-pressure liquid chromatography | HPLC |
| Hertz | Hz |
| Potassium iodide | KI |
| Potassium acetate | KOAc |
| Potassium carbonate | $K_2CO_3$ |
| Lithium aluminum hydride | LAH |
| Liquid chromatography and mass spectrometry | LCMS |
| Molar | M |
| Mass to charge ratio | m/z |
| Milligrams | mg |
| Minute | min |
| Milliliter | mL |
| Microliter | μL |
| Mass spectrometry | MS |
| Deteromethanol | $MeOD-d_4$ |
| Methanol | MeOH |
| (2-Dicyclohexylphospino-2',6'-diisopropoxy-1.1'-biphenyl)[3-(3]-amino-1,1'biphenyl)]palladium(II) methanesulfonate, RuPhos-G3-Palladacycle | RuPhos Pd G3 |
| Sodium borohydride | $NaBH_4$ |
| Sodium carbonate | $Na_2CO_3$ |
| Sodium hydride | NaH |
| Sodium azide | $NaN_3$ |
| Sodium nitrite | $NaNO_2$ |
| Nuclear magnetic resonance | NMR |
| Triphenylphosphine | $PPh_3$ |
| Precipitate | ppt |
| Room temperature | rt |
| Saturated | sat |
| Supercritical Fluid Chromatography | SFC |
| Thionyl chloride | $SOCl_2$ |
| tert-butanol | t-BuOH |
| Triethyl amine | TEA |
| Trifluoroacetic acid | TFA |
| Trifluoroacetic anhydride | TFAA |
| Tetrahydrofuran | THF |

"Alkyl" refers to a straight- or branched-chain alkyl group having from 1 to 12 carbon atoms in the chain. Examples of alkyl groups include methyl (Me, which also can be structurally depicted by the symbol, "I"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-6}$alkyl as used here refers to a straight- or branched-chain alkyl group having from 1 to 6 carbon atoms in the chain. The term $C_{1-4}$alkyl as used here refers to a straight- or branched-chain alkyl group having from 1 to 4 carbon atoms in the chain. The term $C_{1-3}$alkyl as used here refers to a straight- or branched-chain alkyl group having from 1 to 3 carbon atoms in the chain. The term $C_{1-2}$alkyl as used here refers to an alkyl group having from 1 to 2 carbon atoms in the chain.

"Aryl" refers to a monocyclic, aromatic carbocycle (ring structure having ring atoms that are all carbon) having 6 atoms per ring. Carbon atoms in the aryl groups are $sp^2$ hybridized.

"Compounds of Formula (I)" refers to compounds encompassed by Formula (I) as described in the Summary. Unless required otherwise by context, the term "compounds of Formula (I)" encompasses compounds of Formula (Ia), Formula (Ib), Formula (Ic), and Formula (Id) as described in this disclosure. Thus, unless required otherwise by context, disclosure of an embodiment relating to a "compound of Formula (I)" is also a disclosure of an embodiment relating a compound of Formula (Ia), a disclosure of an embodiment relating to a compound of Formula (Ib), a disclosure of an embodiment relating to a compound of Formula (Ic), and a disclosure of an embodiment relating to a compound of Formula (Id).

"Cycloalkyl" refers to a saturated or partially saturated carbocycle having from 3 to 12 ring atoms per carbocycle. Illustrative examples of cycloalkyl groups include the following entities, in the form of properly bonded moieties:

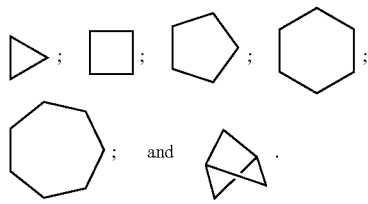

"Effective amount" means an amount or dose of an agent (e.g., a compound of the disclosure or a pharmaceutical composition of the disclosure) sufficient to generally bring about the desired therapeutic or prophylactic benefit in a subject in need of treatment for a designated disease, disorder, or condition. Effective amounts or doses of the compounds or pharmaceutical compositions of the disclosure can be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician.

"Halo" or "halogen" represents chloro, fluoro, bromo or iodo.

"Haloalkyl" refers to a straight- or branched-chain alkyl group having from 1 to 12 carbon atoms in the chain optionally substituting hydrogens with halogens. The term "$C_{1-6}$haloalkyl" as used here refers to a straight- or branched-chain alkyl group having from 1 to 6 carbon atoms in the chain, substituting one or more hydrogens with halogens. The term "$C_{1-3}$haloalkyl" as used here refers to a straight- or branched-chain alkyl group having from 1 to 3 carbon atoms in the chain, substituting one or more hydrogens with halogens. Examples of haloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

"Heterocycloalkyl" or "heterocycloalkyl ring" refers to a monocyclic ring structure that is saturated or partially saturated and has from 4 to 7 ring atoms per ring structure selected from carbon atoms and up to two heteroatoms selected from nitrogen, oxygen, and sulfur. Illustrative entities, in the form of properly bonded moieties, include:

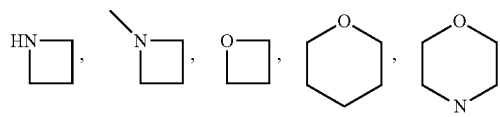

"Isotopic variant" refers to a compound of the disclosure (e.g., a compound of Formula (I)) that is isotopically labeled. Isotopic variants have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

"Pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

"Pharmaceutically active metabolite" means a pharmacologically active product of metabolism in the body of a compound.

"Phenyl" refers to the following moiety:

"Prodrug" means a precursor of a compound that, following administration to a subject, yields the compound in vivo via a chemical or physiological process such as solvolysis or enzymatic cleavage, or under physiological conditions (e.g., a prodrug on being brought to physiological pH is converted to a compound of Formula (I). A "pharmaceutically acceptable prodrug" is a prodrug that is biologically tolerable and otherwise biologically suitable for administration to a subject.

"Substituted" means that the specified group or moiety bears one or more substituents. "Unsubstituted" means that the specified group bears no substituents. "Optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

"Subject" refers to a mammalian subject, preferably a human.

"Treat," "treatment" or "treating" refers to administration of a compound or pharmaceutical composition of the disclosure to a subject for the purpose of affecting a therapeutic or prophylactic benefit. Unless required otherwise by context, treating includes reversing, ameliorating, alleviating, inhibiting the progress of, lessening the severity of, or preventing a disease, disorder, or condition, or one or more symptoms of such disease, disorder or condition.

Those skilled in the art will recognize that the species of groups listed or illustrated in this Section are not exhaustive, and that additional species within the scope of these defined terms can also be selected.

4.2. Additional Terminology

To provide a more concise description, some of the quantitative expressions given in this disclosure are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical structural formulae are provided throughout the disclosure. For a given formula, this disclosure encompasses the compound(s) depicted by the formula as well as certain variations and forms thereof. For example, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (e.g., cis and trans isomers), as tautomers, or as atropisomers.

The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬ and ◀ are used as meaning the same spatial arrangement in chemical structures shown herein. Analogously, the symbols ⦀⦀⦀⦀⦀ and ⸱⸱⸱⸱⦀⦀⦀ are used as meaning the same spatial arrangement in chemical structures shown herein.

When referring to any formula given herein, the selection of a particular moiety from a list of possible species for a specified variable is not intended to define the same choice of the species for the variable appearing elsewhere. In other words, where a variable appears more than once, the choice of a species from a specified list is independent of the choice of another species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this disclosure given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. Shorter terminology, such as, "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^2$, $R^3$, $R^5$, $R^{6a}$, $R^{6b}$, $R^7$, $R^8$, and any other generic substituent symbol used herein.

Furthermore, when more than one assignment is given for any member or substituent, embodiments of this disclosure comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this disclosure for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. Shorter terminology, such as "$S_{example}$ is one of $S_1$, $S_2$, and $S_3$," is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^2$, $R^3$, $R^5$, $R^{6a}$, $R^{6b}$, $R^7$, $R^8$, and any other generic substituent symbol used herein.

The nomenclature "$C_{i-j}$" with j>i, when applied herein to a class of substituents, is meant to refer to embodiments of this disclosure for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

4.3. Compounds of the Disclosure

In one aspect, this disclosure provides compounds of Formula (I):

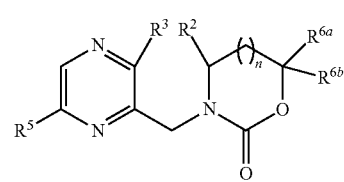

(I)

and pharmaceutically acceptable salts, solvates, isotopic variants, and N-oxides of compounds of Formula (I), wherein:

n is 0 or 1;

$R^2$ is H or alkyl;

$R^3$ is H or alkyl;

$R^5$ is aryl which is optionally substituted with one or two substituents each of which is independently halogen, haloalkyl, or O-haloalkyl; and $R^{6a}$ and $R^{6b}$ are, each independent from the other, H or alkyl which is optionally substituted with (=O) and a heterocycloalkyl, —NHCH$_3$, or —N(CH$_3$)$_2$; or $R^{6a}$ and $R^{6b}$ together with the carbon atom to which they are attached form (i) a cycloalkyl ring or (ii) a heterocycloalkyl ring which is optionally substituted with alkyl.

In some embodiments, the compound of Formula (I) is a compound of Formula (Ia):

(Ia)

In other embodiments, the compound of Formula (I) is a compound of Formula (Ib):

(Ib)

In other embodiments, the compound of Formula (I) is a compound of Formula (Ic):

(Ic)

wherein $R^7$ is H or halogen, and $R^8$ is haloalkyl or O-haloalkyl.

In other embodiments, the compound of Formula (I) is a compound of Formula (Id):

(Id)

wherein each of $R^7$ is H or halogen, and $R^8$ is haloalkyl or O-haloalkyl.

In another aspect, the disclosure provides enantiomers of compounds of Formula (I).

In another aspect, the disclosure provides diastereomers of compounds of Formula (I).

In another aspect, the disclosure provides pharmaceutically acceptable prodrugs of compounds of Formula (I).

In another aspect, the disclosure provides pharmaceutically active metabolites of compounds of Formula (I).

Further embodiments relating to variables $R^2$, $R^3$, $R^5$ $R^{6a}$, and $R^{6b}$ are described in Sections 4.3.1 to 4.3.4. It should be understood that an embodiment relating to a given variable described in one of Sections 4.3.1 to 4.3.4 can be combined with one or more embodiments in one or more of the other of Sections 4.3.1 to 4.3.4 (e.g., an embodiment relating to $R^2$ described in Section 4.3.1 can be combined with an embodiment relating to $R^3$ described in Section 4.3.2, an embodiment relating to $R^5$ described in Section 4.3.3, and an embodiment relating to $R^{6a}$ and $R^{6b}$ described in Section 4.3.4), and that such combinations are within the scope of the disclosure.

4.3.1. $R^2$

In some embodiments of the compounds of the disclosure, $R^2$ is H or alkyl, for example, C$_1$-C$_6$alkyl or C$_1$-C$_3$alkyl. In some embodiments, $R^2$ is H. In other embodiments, $R^2$ is —CH$_3$.

In some embodiments of compounds of the disclosure, the stereochemistry at the carbon to which $R^2$ is attached is (R). In other embodiments of compounds of the disclosure, the stereochemistry at the carbon to which $R^2$ is attached is (S).

4.3.2. $R^3$

In some embodiments of the compounds of the disclosure, $R^3$ is H or alkyl (e.g., C$_1$-C$_6$alkyl or C$_1$-C$_3$alkyl). In some embodiments of the compounds of the disclosure, $R^3$ is H. In other embodiments of the compounds of the disclosure, $R^3$ is alkyl (e.g., C$_1$-C$_6$alkyl, C$_1$-C$_3$alkyl, or C$_1$-C$_2$alkyl). In some embodiments of the compounds of the disclosure, $R^3$ is —CH$_3$.

4.3.3. $R^5$

In some embodiments of the compounds of the disclosure, $R^5$ is aryl which is optionally substituted with one or two substituents each of which is independently halogen (e.g., F or Cl), haloalkyl (e.g., C$_1$-C$_6$haloalkyl, C$_1$-C$_3$haloalkyl, or C$_1$-C$_2$haloalkyl), or O-haloalkyl (e.g., O—C$_1$-C$_6$haloalkyl, O—C$_1$-C$_3$haloalkyl, or O—C$_1$-C$_2$haloalkyl). In some embodiments of the compounds of the disclosure, $R^5$ is aryl substituted with one substituent. In other embodiments of the compounds of the disclosure, $R^5$ is aryl substituted with two substituents.

In some embodiments of the compounds of the disclosure, $R^5$ is

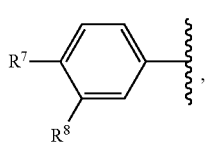

wherein $R^7$ is H or halogen (e.g., F or Cl) and $R^8$ is haloalkyl (e.g., $C_1$-$C_6$haloalkyl, $C_1$-$C_3$haloalkyl, or $C_1$-$C_2$haloalkyl), or O-haloalkyl (e.g., O—$C_1$-$C_6$haloalkyl, O—$C_1$-$C_3$haloalkyl, or O—$C_1$-$C_2$haloalkyl).

In some embodiments of the compounds of the disclosure, $R^7$ is H, F or Cl. In some embodiments of the compounds of the disclosure, $R^7$ is H. In some embodiments of the compounds of the disclosure, $R^7$ is F. In some embodiments of the compounds of the disclosure, $R^7$ is Cl.

In some embodiments of the compounds of the disclosure $R^8$ is haloalkyl (e.g., $C_1$-$C_6$haloalkyl, $C_1$-$C_3$haloalkyl, or $C_1$-$C_2$haloalkyl). In some embodiments of the compounds of the disclosure $R^8$ is —$CHF_2$ or —$CF_2CH_3$. In some embodiments of the compounds of the disclosure $R^8$ is —$CHF_2$. In some embodiments of the compounds of the disclosure $R^8$ is —$CF_2CH_3$.

In some embodiments of the compounds of the disclosure $R^8$ is O-haloalkyl (e.g., O—$C_1$-$C_6$haloalkyl, O—$C_1$-$C_3$haloalkyl, or O—$C_1$-$C_2$haloalkyl). In some embodiments of the compounds of the disclosure $R^8$ is —$OCHF_2$.

In some embodiments of the compounds of the disclosure $R^7$ is H, F or Cl, and $R^8$ is —$CHF_2$, —$CF_2CH_3$ or —$OCHF_2$.

In some embodiments of the compounds of the disclosure, $R^5$ is:

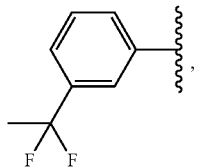 , 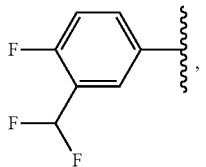 ,

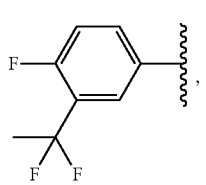 , 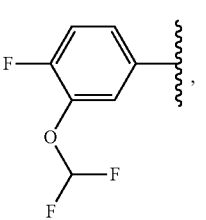 , or

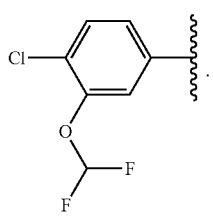

In some embodiments of the compounds of the disclosure, $R^5$ is

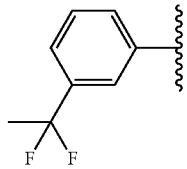 [SMILES: *c1cccc(C(C)(F)F)c1]

In other embodiments of the compounds of the disclosure, $R^5$ is

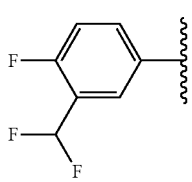

In other embodiments of the compounds of the disclosure, $R^5$ is

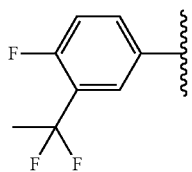

In other embodiments of the compounds of the disclosure, $R^5$ is

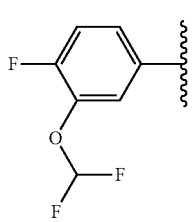

In other embodiments of the compounds of the disclosure, $R^5$ is

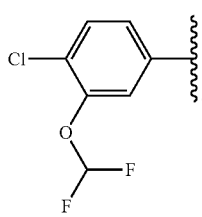

4.3.4. $R^{6a}$ and $R^{6b}$

In some embodiments of the compounds of the disclosure, $R^{6a}$ and $R^{6b}$ are, each independent from the other, H or alkyl which is optionally substituted with (=O) and a heterocycloalkyl, —$NHCH_3$, or —$N(CH_3)_2$; or $R^{6a}$ and $R^{6b}$ together with the carbon atom to which they are attached form (i) a cycloalkyl ring or (ii) a heterocycloalkyl ring which is optionally substituted with alkyl.

In some embodiments of the compounds of the disclosure, $R^{6a}$ and $R^{6b}$ are, each independent from the other, H or $C_1$-$C_6$alkyl which is optionally substituted with (=O) and a 4 to 6 membered heterocycloalkyl, —NHCH$_3$, or —N(CH$_3$)$_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_6$alkyl.

In some embodiments of the compounds of the disclosure, $R^{6a}$ and $R^{6b}$ are, each independent from the other, H or $C_1$-$C_3$alkyl which is optionally substituted with (=O) and a 4 to 6 membered heterocycloalkyl, —NHCH$_3$, or —N(CH$_3$)$_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_3$alkyl.

In some embodiments of the compounds of the disclosure, $R^{6a}$ and $R^{6b}$ are both H.

In some embodiments of the compounds of the disclosure, one of $R^{6a}$ and $R^{6b}$ is H and the other is alkyl (e.g., $C_1$-$C_6$alkyl or $C_1$-$C_3$alkyl) which is optionally substituted with (=O) and a heterocycloalkyl (e.g., a 4 to 6 membered heterocycloalkyl ring), —NHCH$_3$, or —N(CH$_3$)$_2$.

In some embodiments of the compounds of the disclosure, one of $R^{6a}$ and $R^{6b}$ is H and the other is —CH$_3$.

In some embodiments of the compounds of the disclosure, one of $R^{6a}$ and $R^{6b}$ is H and the other is

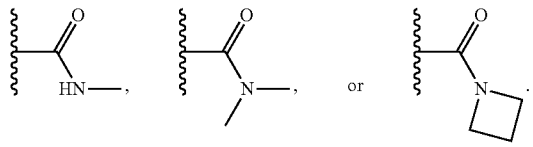

In some embodiments of the compounds of the disclosure, $R^{6a}$ and $R^{6b}$ are both alkyl (e.g., $C_1$-$C_6$alkyl or $C_1$-$C_2$alkyl).

In some embodiments of the compounds of the disclosure, $R^{6a}$ and $R^{6b}$ are both —CH$_3$.

In some embodiments of the compounds of the disclosure, $R^{6a}$ and $R^{6b}$ together with the carbon atom to which they are attached form a cycloalkyl ring (e.g., a $C_3$-$C_6$cycloalkyl ring) or a heterocycloalkyl ring (e.g., a 4 to 6 membered heterocycloalkyl ring) which is optionally substituted with alkyl (e.g., $C_1$-$C_6$alkyl or $C_1$-$C_3$alkyl).

In some embodiments of the compounds of the disclosure, $R^{6a}$ and $R^{6b}$ together with the carbon atom to which they are attached form a cyclopropyl ring.

In some embodiments of the compounds of the disclosure, $R^{6a}$ and $R^{6b}$ together with the carbon atom to which they are attached form

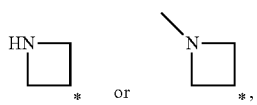

wherein * denotes the point of attachment of the ring to the remainder of the molecule.

In some embodiments of the compounds of the disclosure, the stereochemistry at the carbon to which $R^{6a}$ and $R^{6b}$ are attached is (R). In other embodiments of the compounds of the disclosure the stereochemistry at the carbon to which $R^{6a}$ and $R^{6b}$ are attached is (S).

4.3.5. Compound Forms

A compounds of the disclosure can be, for example, a compound of Formula (I) in the form of a free acid or a free base. A compound of the disclosure can also be a compound of Formula (I) in the form of a pharmaceutically acceptable salt. A compound of the disclosure can also be a compound of Formula (I) in the form of a solvate. A compound of the disclosure can also be an isotopic variant of a compound of Formula (I). A compound of the disclosure can also be in the form of an N-oxide of a compound of Formula (I). A compound of the disclosure can also be in the form of a prodrug of a compound of Formula (I). A compound of the disclosure can also be in the form of a metabolite of a compound of Formula (I).

4.3.5.1. Pharmaceutically Acceptable Salts

In some embodiments, a compound of Formula (I) is the form of a pharmaceutically acceptable salt. Pharmaceutically acceptable salts are preferably salts that are non-toxic, biologically tolerable, or otherwise biologically suitable for administration to a subject. Preferably, a pharmaceutically acceptable salt of a compound of Formula (I) possesses the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) is a base, a desired pharmaceutically acceptable salt can be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, a desired pharmaceutically acceptable salt can be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

4.3.5.2. Solvates

In some embodiments, a compound of Formula (I) is in the form of a solvate. Many organic compounds can form solvates with solvents in which they are reacted or from which they are precipitated or crystallized. Solvates include those formed from the interaction or complexation of compounds of the disclosure with one or more solvents, either in solution or as a solid or crystalline form. In some embodiments, the solvent is water and the solvates are hydrates.

4.3.5.3. Isotopic Variants

In some embodiments, a compound of Formula (I) is the form of an isotopic variant, e.g., a deuterated compound of Formula (I). Such isotopic variants are useful in metabolic studies (preferably with $^{14}C$), reaction kinetic studies (with, for example deuterium (abbreviated "D" or "$^2H$"); or tritium (abbreviated "T" or "$^3H$")), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound can be particularly preferred for PET or SPECT studies. Further, substitution with heavier isotopes such as deuterium can afford certain therapeutic advantages resulting from greater metabolic stability, for example increased in vivo half-life or reduced dosage requirements. Isotopically labeled compounds of this disclosure can generally be prepared by carrying out the procedures disclosed in the schemes or in the examples described herein by substituting a readily available isotopically labeled reagent for a non-isotopically labeled reagent.

4.3.5.4. N-oxides

In some embodiments, a compound of Formula (I) is the form of an N-oxide. N-oxides can be prepared according to techniques known in the art. See, e.g., Yousif, S., Arkivoc, 2001, 2001(1):242-268.

4.3.5.5. Prodrugs and Pharmaceutically Active Metabolites

The disclosure also provides pharmaceutically acceptable prodrugs of the compounds of Formula (I) and treatment methods employing such pharmaceutically acceptable prodrugs. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

The present disclosure also relates to pharmaceutically active metabolites of the compounds of Formula (I). Prodrugs and active metabolites of a compound can be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, Drug Dev Res. 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

4.3.6. Exemplary Compounds of Formula (I)

Exemplary compounds of the disclosure are listed in Table 2, below. In various aspects, the disclosure provides, for example, pharmaceutically acceptable salts, solvates, isotopic variants, and N-oxides of the compounds listed in Table 2.

TABLE 2

| Example # | Compound Name |
|---|---|
| 1 | 3-[[6-[3-(Difluoromethyl)-4-fluoro-phenyl]pyrazin-2-yl]methyl]oxazolidin-2-one; |
| 2 | 3-[[6-[3-(Difluoromethoxy)-4-fluoro-phenyl]pyrazin-2-yl]methyl]oxazolidin-2-one; |
| 3 | 5-[[6-[3-(Difluoromethyl)-4-fluoro-phenyl]pyrazin-2-yl]methyl]-7-oxa-5-azaspiro[2.4]heptan-6-one; |
| 4 | 3-[[6-[3-(Difluoromethyl)-4-fluoro-phenyl]pyrazin-2-yl]methyl]-5,5-dimethyl-oxazolidin-2-one; |
| 5 | (5R)-3-[[6-[3-(Difluoromethyl)-4-fluoro-phenyl]pyrazin-2-yl]methyl]-5-methyl-oxazolidin-2-one; |
| 6 | (5S)-3-[[6-[3-(Difluoromethyl)-4-fluoro-phenyl]pyrazin-2-yl]methyl]-5-methyl-oxazolidin-2-one; |
| 7 | (4R)-3-[[6-[3-(Difluoromethyl)-4-fluoro-phenyl]pyrazin-2-yl]methyl]-4-methyl-oxazolidin-2-one; |
| 8 | (4S)-3-[[6-[3-(Difluoromethyl)-4-fluoro-phenyl]pyrazin-2-yl]methyl]-4-methyl-oxazolidin-2-one; |

TABLE 2-continued

| Example # | Compound Name |
|---|---|
| 9 | 3-[[6-[3-(Difluoromethyl)-4-fluoro-phenyl]pyrazin-2-yl]methyl]-1,3-oxazinan-2-one; |
| 10 | 5-[[6-[3-(Difluoromethyl)-4-fluoro-phenyl]-3-methyl-pyrazin-2-yl]methyl]-7-oxa-5-azaspiro[2.4]heptan-6-one; |
| 11 | (4R)-3-[[6-[3-(Difluoromethyl)-4-fluoro-phenyl]-3-methyl-pyrazin-2-yl]methyl]-4-methyl-oxazolidin-2-one; |
| 12 | (4S)-3-[[6-[3-(Difluoromethyl)-4-fluoro-phenyl]-3-methyl-pyrazin-2-yl]methyl]-4-methyl-oxazolidin-2-one; |
| 13 | (5R)-3-[[6-[3-(Difluoromethyl)-4-fluoro-phenyl]-3-methyl-pyrazin-2-yl]methyl]-5-methyl-oxazolidin-2-one; |
| 14 | (5S)-3-[[6-[3-(Difluoromethyl)-4-fluoro-phenyl]-3-methyl-pyrazin-2-yl]methyl]-5-methyl-oxazolidin-2-one; |
| 15 | 3-[[6-[3-(Difluoromethyl)-4-fluoro-phenyl]-3-methyl-pyrazin-2-yl]methyl]-1,3-oxazinan-2-one; |
| 16 | 5-[[6-[3-(Difluoromethoxy)-4-fluoro-phenyl]pyrazin-2-yl]methyl]-7-oxa-5-azaspiro[2.4]heptan-6-one; |
| 17 | 3-[[6-[3-(Difluoromethoxy)-4-fluoro-phenyl]pyrazin-2-yl]methyl]-5,5-dimethyl-oxazolidin-2-one; |
| 18 | (4R)-3-[[6-[3-(Difluoromethoxy)-4-fluoro-phenyl]pyrazin-2-yl]methyl]-4-methyl-oxazolidin-2-one; |
| 19 | (4S)-3-[[6-[3-(Difluoromethoxy)-4-fluoro-phenyl]pyrazin-2-yl]methyl]-4-methyl-oxazolidin-2-one; |
| 20 | (5R)-3-[[6-[3-(Difluoromethoxy)-4-fluoro-phenyl]pyrazin-2-yl]methyl]-5-methyl-oxazolidin-2-one; |
| 21 | (5S)-3-[[6-[3-(Difluoromethoxy)-4-fluoro-phenyl]pyrazin-2-yl]methyl]-5-methyl-oxazolidin-2-one; |
| 22 | 3-[[6-[3-(Difluoromethoxy)-4-fluoro-phenyl]pyrazin-2-yl]methyl]-1,3-oxazinan-2-one; |
| 23 | 5-[[6-[3-(Difluoromethoxy)-4-fluoro-phenyl]-3-methyl-pyrazin-2-yl]methyl]-7-oxa-5-azaspiro[2.4]heptan-6-one; |
| 24 | (4R)-3-[[6-[3-(Difluoromethoxy)-4-fluoro-phenyl]-3-methyl-pyrazin-2-yl]methyl]-4-methyl-oxazolidin-2-one; |
| 25 | (4S)-3-[[6-[3-(Difluoromethoxy)-4-fluoro-phenyl]-3-methyl-pyrazin-2-yl]methyl]-4-methyl-oxazolidin-2-one; |
| 26 | (5R)-3-[[6-[3-(Difluoromethoxy)-4-fluoro-phenyl]-3-methyl-pyrazin-2-yl]methyl]-5-methyl-oxazolidin-2-one; |
| 27 | (5S)-3-[[6-[3-(Difluoromethoxy)-4-fluoro-phenyl]-3-methyl-pyrazin-2-yl]methyl]-5-methyl-oxazolidin-2-one; |
| 28 | 3-[[6-[3-(Difluoromethoxy)-4-fluoro-phenyl]-3-methyl-pyrazin-2-yl]methyl]-1,3-oxazinan-2-one; |
| 29 | 5-[[6-[4-Chloro-3-(difluoromethoxy)phenyl]pyrazin-2-yl]methyl]-7-oxa-5-azaspiro[2.4]heptan-6-one; |
| 30 | 3-[[6-[4-Chloro-3-(difluoromethoxy)phenyl]pyrazin-2-yl]methyl]-5,5-dimethyl-oxazolidin-2-one; |
| 31 | (5R)-3-[[6-[4-Chloro-3-(difluoromethoxy)phenyl]pyrazin-2-yl]methyl]-5-methyl-oxazolidin-2-one; |
| 32 | (5S)-3-[[6-[4-Chloro-3-(difluoromethoxy)phenyl]pyrazin-2-yl]methyl]-5-methyl-oxazolidin-2-one; |
| 33 | (4R)-3-[[6-[4-Chloro-3-(difluoromethoxy)phenyl]pyrazin-2-yl]methyl]-4-methyl-oxazolidin-2-one; |
| 34 | (4S)-3-[[6-[4-Chloro-3-(difluoromethoxy)phenyl]pyrazin-2-yl]methyl]-4-methyl-oxazolidin-2-one; |
| 35 | 3-[[6-[4-Chloro-3-(difluoromethoxy)phenyl]pyrazin-2-yl]methyl]-1,3-oxazinan-2-one; |
| 36 | 5-[[6-[4-Chloro-3-(difluoromethoxy)phenyl]-3-methyl-pyrazin-2-yl]methyl]-7-oxa-5-azaspiro[2.4]heptan-6-one; |
| 37 | 3-[[6-[4-Chloro-3-(difluoromethoxy)phenyl]-3-methyl-pyrazin-2-yl]methyl]-1,3-oxazinan-2-one; |
| 38 | 5-[[6-[3-(1,1-Difluoroethyl)phenyl]pyrazin-2-yl]methyl]-7-oxa-5-azaspiro[2.4]heptan-6-one; |
| 39 | 3-[[6-[3-(1,1-Difluoroethyl)phenyl]pyrazin-2-yl]methyl]-5,5-dimethyl-oxazolidin-2-one; |
| 40 | (5R)-3-[[6-[3-(1,1-Difluoroethyl)phenyl]pyrazin-2-yl]methyl]-5-methyl-oxazolidin-2-one; |
| 41 | (5S)-3-[[6-[3-(1,1-Difluoroethyl)phenyl]pyrazin-2-yl]methyl]-5-methyl-oxazolidin-2-one; |
| 42 | 3-[[6-[3-(1,1-Difluoroethyl)phenyl]pyrazin-2-yl]methyl]-1,3-oxazinan-2-one; |
| 43 | 5-[[6-[3-(1,1-Difluoroethyl)phenyl]-3-methyl-pyrazin-2-yl]methyl]-7-oxa-5-azaspiro[2.4]heptan-6-one; |
| 44 | 3-[[6-[3-(1,1-Difluoroethyl)phenyl]-3-methyl-pyrazin-2-yl]methyl]-5,5-dimethyl-oxazolidin-2-one; |
| 45 | 3-[[6-[3-(1,1-Difluoroethyl)phenyl]-3-methyl-pyrazin-2-yl]methyl]-1,3-oxazinan-2-one; |
| 46 | (4R)-3-[[6-[3-(1,1-Difluoroethyl)-4-fluoro-phenyl]pyrazin-2-yl]methyl]-4-methyl-oxazolidin-2-one; |
| 47 | (4S)-3-[[6-[3-(1,1-Difluoroethyl)-4-fluoro-phenyl]pyrazin-2-yl]methyl]-4-methyl-oxazolidin-2-one; |

TABLE 2-continued

| Example # | Compound Name |
|---|---|
| 48 | 6-[[6-[3-(1,1-Difluoroethyl)phenyl]pyrazin-2-yl]methyl]-8-oxa-6-azaspiro[2.5]octan-7-one; |
| 49 | 6-[[6-[3-(Difluoromethoxy)-4-fluoro-phenyl]pyrazin-2-yl]methyl]-8-oxa-6-azaspiro[2.5]octan-7-one; |
| 50 | 6-[[6-[4-Chloro-3-(difluoromethoxy)phenyl]pyrazin-2-yl]methyl]-8-oxa-6-azaspiro[2.5]octan-7-one; |
| 51 | 6-[[6-[4-Chloro-3-(difluoromethoxy)phenyl]-3-methyl-pyrazin-2-yl]methyl]-8-oxa-6-azaspiro[2.5]octan-7-one; |
| 52 | 6-[[6-[3-(Difluoromethyl)-4-fluoro-phenyl]pyrazin-2-yl]methyl]-8-oxa-6-azaspiro[2.5]octan-7-one; |
| 53 | 6-[[6-[3-(Difluoromethyl)-4-fluoro-phenyl]-3-methyl-pyrazin-2-yl]methyl]-8-oxa-6-azaspiro[2.5]octan-7-one; |
| 54 | 6-[[6-[3-(Difluoromethoxy)-4-fluoro-phenyl]-3-methyl-pyrazin-2-yl]methyl]-8-oxa-6-azaspiro[2.5]octan-7-one; |
| 55 | (R/S)-3-[[6-[4-Chloro-3-(difluoromethoxy)phenyl]pyrazin-2-yl]methyl]-N,N-dimethyl-2-oxo-oxazolidine-5-carboxamide; |
| 56 | (R/S)-3-[[6-[4-Chloro-3-(difluoromethoxy)phenyl]pyrazin-2-yl]methyl]-N-methyl-2-oxo-oxazolidine-5-carboxamide; |
| 57 | 5-(Azetidine-1-carbonyl)-3-[[6-[4-chloro-3-(difluoromethoxy)phenyl]pyrazin-2-yl]methyl]oxazolidin-2-one; |
| 58 | (R/S)-5-(Azetidine-1-carbonyl)-3-[[6-[3-(difluoromethyl)-4-fluoro-phenyl]pyrazin-2-yl]methyl]oxazolidin-2-one; |
| 59 | (R/S)-3-[[6-[3-(Difluoromethyl)-4-fluoro-phenyl]pyrazin-2-yl]methyl]-N-methyl-2-oxo-oxazolidine-5-carboxamide; |
| 60 | (R/S)-3-[[6-[3-(Difluoromethoxy)-4-fluoro-phenyl]pyrazin-2-yl]methyl]-N-methyl-2-oxo-oxazolidine-5-carboxamide; |
| 61 | (R/S)-5-(Azetidine-1-carbonyl)-3-[[6-[3-(difluoromethoxy)-4-fluoro-phenyl]pyrazin-2-yl]methyl]oxazolidin-2-one; |
| 62 | (R/S)-3-[[6-[3-(1,1-Difluoroethyl)-4-fluoro-phenyl]pyrazin-2-yl]methyl]-N,N-dimethyl-2-oxo-oxazolidine-5-carboxamide; |
| 63 | (R/S)-3-[[6-[3-(1,1-Difluoroethyl)-4-fluoro-phenyl]pyrazin-2-yl]methyl]-N-methyl-2-oxo-oxazolidine-5-carboxamide; |
| 64 | (R/S)-5-(Azetidine-1-carbonyl)-3-[[6-[3-(1,1-difluoroethyl)-4-fluoro-phenyl]pyrazin-2-yl]methyl]oxazolidin-2-one; |
| 65 | (R/S)-3-[[6-[3-(Difluoromethyl)-4-fluoro-phenyl]pyrazin-2-yl]methyl]-N,N-dimethyl-2-oxo-oxazolidine-5-carboxamide; |
| 66 | (R/S)-3-[[6-[3-(Difluoromethoxy)-4-fluoro-phenyl]pyrazin-2-yl]methyl]-N,N-dimethyl-2-oxo-oxazolidine-5-carboxamide; |
| 67 | 6-[[6-[4-Chloro-3-(difluoromethoxy)phenyl]pyrazin-2-yl]methyl]-8-oxa-2,6-diazaspiro[3.4]octan-7-one; and |
| 68 | 6-[[6-[4-Chloro-3-(difluoromethoxy)phenyl]pyrazin-2-yl]methyl]-2-methyl-8-oxa-2,6-diazaspiro[3.4]octan-7-one. |

In the event of an inconsistency between a compound name shown in Table 2 and a structure provided herein for the compound, the structure shall control unless it is clear from context that the structure is incorrect.

Exemplary compounds of the disclosure are listed in Table 3, below. In various aspects, the disclosure provides, for example, pharmaceutically acceptable salts, solvates, isotopic variants, and N-oxides of the compounds listed in Table 3.

TABLE 3

| Example # | Compound Name |
|---|---|
| 3 | 5-[[6-[3-(Difluoromethyl)-4-fluoro-phenyl]pyrazin-2-yl]methyl]-7-oxa-5-azaspiro[2.4]heptan-6-one; |
| 8 | 3-[[6-[3-(Difluoromethoxy)-4-fluoro-phenyl]pyrazin-2-yl]methyl]-1,3-oxazinan-2-one; |
| 11 | 5-[[6-[4-Chloro-3-(difluoromethoxy)phenyl]pyrazin-2-yl]methyl]-7-oxa-5-azaspiro[2.4]heptan-6-one; |
| 15 | 3-[[6-[4-Chloro-3-(difluoromethoxy)phenyl]pyrazin-2-yl]methyl]-1,3-oxazinan-2-one; and |
| 59 | 3-[[6-[3-(Difluoromethoxy)-4-fluoro-phenyl]-3-methyl-pyrazin-2-yl]methyl]-1,3-oxazinan-2-one. |

In the event of an inconsistency between a compound name shown in Table 3 and a structure provided herein for the compound, the structure shall control unless it is clear from context that the structure is incorrect.

4.4. Pharmaceutical Compositions

The disclosure further provides pharmaceutical compositions comprising a compound of the disclosure (e.g., a compound of Formula (I) or a pharmaceutically acceptable salt, solvate, isotopic variant, or N-oxide thereof). Pharmaceutical compositions of the disclosure can comprise a single compound of the disclosure or more than one compound of the disclosure. Pharmaceutical compositions of the disclosure typically comprise at least one pharmaceutically acceptable excipient (e.g., one or more than one pharmaceutically acceptable excipient).

In some embodiments, a pharmaceutical composition of the disclosure comprises at least one compound selected from compounds of Formula (I), pharmaceutically acceptable salts of compounds of Formula (I), solvates of compounds of Formula (I), isotopic variants of compounds of Formula (I), N-oxides of compounds of Formula (I) and solvates of compounds of Formula (I), pharmaceutically acceptable prodrugs of compounds of Formula (I), and pharmaceutically active metabolites of compounds of Formula (I); and at least one pharmaceutically acceptable excipient.

In some further embodiments, a pharmaceutical composition of the disclosure comprises at least one compound selected from compounds of Formula (Ia), pharmaceutically acceptable salts of compounds of Formula (Ia), solvates of compounds of Formula (Ia), isotopic variants of compounds of Formula (Ia), N-oxides of compounds of Formula (Ia) and solvates of compounds of Formula (Ia), pharmaceutically acceptable prodrugs of compounds of Formula (Ia), and pharmaceutically active metabolites of compounds of Formula (Ia); and at least one pharmaceutically acceptable excipient.

In some further embodiments, a pharmaceutical composition of the disclosure comprises at least one compound selected from compounds of Formula (Ib), pharmaceutically acceptable salts of compounds of Formula (Ib), solvates of compounds of Formula (Ib), isotopic variants of compounds of Formula (Ib), N-oxides of compounds of Formula (Ib) and solvates of compounds of Formula (Ib), pharmaceutically acceptable prodrugs of compounds of Formula (Ib), and pharmaceutically active metabolites of compounds of Formula (Ib); and at least one pharmaceutically acceptable excipient.

In some further embodiments, a pharmaceutical composition of the disclosure comprises at least one compound selected from compounds of Formula (Ic), pharmaceutically acceptable salts of compounds of Formula (Ic), solvates of compounds of Formula (Ic), isotopic variants of compounds of Formula (Ic), N-oxides of compounds of Formula (Ic) and solvates of compounds of Formula (Ic), pharmaceutically acceptable prodrugs of compounds of Formula (Ic), and pharmaceutically active metabolites of compounds of Formula (Ic); and at least one pharmaceutically acceptable excipient.

In some further embodiments, a pharmaceutical composition of the disclosure comprises at least one compound selected from compounds of Formula (Id), pharmaceutically acceptable salts of compounds of Formula (Id), solvates of compounds of Formula (Id), isotopic variants of compounds of Formula (Id), N-oxides of compounds of Formula (Id) and solvates of compounds of Formula (Id), pharmaceutically acceptable prodrugs of compounds of Formula (Id), and pharmaceutically active metabolites of compounds of Formula (Id); and at least one pharmaceutically acceptable excipient.

In some embodiments, a pharmaceutical composition of the disclosure comprises at least compound selected from compounds in Table 2, pharmaceutically acceptable salts, solvates, isotopic variants, and N-oxides of compounds in Table 2, pharmaceutically acceptable prodrugs of compounds in Table 2, and pharmaceutically active metabolites of compounds in Table 2; and at least one pharmaceutically acceptable excipient.

The pharmaceutically acceptable excipient(s) included in the pharmaceutical compositions of the disclosure are preferably non-toxic, biologically tolerable, and otherwise biologically suitable for administration to a subject. Pharmaceutically acceptable excipients include inert substances, which can be added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Pharmaceutical compositions of the disclosure can be formulated for various routes of delivery, e.g., oral, parenteral, rectal, topical, or ocular routes, or by inhalation.

Pharmaceutical compositions can be in the form of tablets, capsules, sachets, dragees, powders, granules, lozenges, powders for reconstitution, liquid preparations, or suppositories. Pharmaceutical compositions can be formulated, for example, for intravenous infusion, topical administration, or oral administration.

For oral administration, the compounds of the disclosure can be provided in the form of tablets or capsules, or as a solution, emulsion, or suspension. Oral tablets can include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents can include starch and gelatin. The lubricating agent, if present, can be magnesium stearate, stearic acid or talc. If desired, the tablets can be coated with a material, such as glyceryl monostearate or glyceryl distearate, to delay absorption in the gastrointestinal tract, or can be coated with an enteric coating.

Capsules for oral administration include hard and soft gelatin capsules. To prepare hard gelatin capsules, compounds of the disclosure can be mixed with a solid, semi-solid, or liquid diluent. Soft gelatin capsules can be prepared by mixing the compound of the disclosure with water, an oil such as peanut oil or olive oil, liquid paraffin, a mixture of mono and di-glycerides of short chain fatty acids, polyethylene glycol 400, propylene glycol, or am mixture of any of the foregoing.

Liquids for oral administration can be in the form of suspensions, solutions, emulsions or syrups or can be lyophilized or presented as a dry product for reconstitution with water or other suitable vehicle before use. Such liquid compositions can optionally contain, for example: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of the disclosure can also be administered by non-oral routes. For example, the compositions can be formulated for rectal administration as a suppository. For parenteral use, including intravenous, intramuscular, intraperitoneal, or subcutaneous routes, the compounds of the disclosure can be provided in sterile aqueous solutions or suspensions, buffered to an appropriate pH and isotonicity or in parenterally acceptable oil. Suitable aqueous vehicles include Ringer's solution and isotonic sodium chloride. Such forms can be presented in unit-dose form such as ampules or disposable injection devices, in multi-dose forms such as vials from which the appropriate dose can be withdrawn, or in a solid form or pre-concentrate that can be used to prepare an injectable formulation.

For topical pharmaceutical compositions, compounds of the disclosure can be mixed with a pharmaceutical carrier. Another mode of administering the compounds of the disclosure can utilize a patch formulation to affect transdermal delivery.

Compounds of the disclosure can alternatively be administered in methods of this disclosure by inhalation, via the nasal or oral routes, e.g., in a spray formulation also containing a suitable carrier.

4.5. Uses of Compounds of the Disclosure

Compounds of the disclosure are useful as modulators of the GluN2B receptor. As such modulators, the compounds can act, for example, as antagonists, agonists, or inverse agonists. The term "modulators" include both inhibitors and activators, where "inhibitors" refer to compounds that decrease, prevent, inactivate, desensitize, or down-regulate the GluN2B receptor expression or activity, and "activators" are compounds that increase, activate, facilitate, sensitize, or up-regulate GluN2B receptor expression or activity.

In one aspect, the disclosure provides methods of treating a subject suffering from or diagnosed with a disease, disorder, or medical condition mediated by GluN2B receptor activity, comprising administering to the subject a therapeutically effective amount of a compound of the disclosure, for example a compound of Formula (I) or a pharmaceutically acceptable salt, solvate, isotopic variant, or N-oxide thereof, or a therapeutically effective amount of a pharmaceutical composition of the disclosure, for example a unit dosage form as described in Section 4.4. The treatment methods described herein can comprise, for example, administering at least one (e.g., one) compound of the disclosure or at least one (e.g., one) pharmaceutical composition of the disclosure) to the subject.

In some embodiments, the disease, disorder, or medical condition comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

In some embodiments, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present disclosure include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder. In specific embodiments, the mood disorders and mood affective disorders that can be treated according to the present disclosure are major depressive disorder, treatment-resistant depression and bipolar disorder.

Examples of disorders belonging to the neurotic, stress-related and somatoform disorders that can be treated according to the present disclosure include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present disclosure include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present disclosure include but are not limited to mental and behavioral disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present disclosure include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present disclosure include but are not limited to dystonia including but not limited to focal dystonia, multiple-focal or segmental dystonia, torsion dystonia, hemispheric, generalised and tardive dystonia (induced by psychopharmacological drugs). Focal dystonia includes cervical dystonia (torticolli), blepharospasm (cramp of the eyelid), appendicular dystonia (cramp in the extremities, like the writer's cramp), oromandibular dystonia and spasmodic dysphonia (cramp of the vocal cord).

Examples for episodic and paroxysmal disorders that can be treated according to the present disclosure include, but are not limited to epilepsy, including localization-related (focal)(partial) idiopathic epilepsy and epileptic syndromes with seizures of localized onset, localization-related (focal) (partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present disclosure include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

Once improvement of a subject's disease, disorder, or condition has occurred, the dose can be adjusted for preventative or maintenance treatment. For example, the dosage or the frequency of administration, or both, can be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In some embodiments, administration of a compound of the disclosure (e.g., a compound of Formula (I) or a pharmaceutically acceptable salt thereof), is effective in preventing the disease or delaying onset of symptoms of the disease; for example, preventing a disease, condition or disorder or a symptom thereof in an individual who may be predisposed to the disease, condition or disorder but does not yet experience or display the pathology or symptomatology of the disease.

Compounds and pharmaceutical compositions of the disclosure can be administered as monotherapy, or they can be administered in combination with one or more additional active agents. For example, the additional active agent can be an agent known or discovered to be effective in the treatment of conditions, disorders, or diseases mediated by GluN2B activity, such as another GluN2B modulator or a compound active against another target associated with a subject's particular condition, disorder, or disease. The combination may serve to increase efficacy (e.g., by including in the combination a compound potentiating the potency or effectiveness of a compound of the disclosure), decrease one or more side effects, or decrease the required dose of a compound of the disclosure.

4.6. Exemplary Methods of Making Compounds of the Disclosure

Illustrative synthetic schemes for the general preparation of compounds of Formula (I) are described below. Artisans will recognize that, to obtain the various compounds described herein, starting materials can be suitably selected so that the ultimately desired substituents will be carried through the reaction scheme with or without protection as appropriate to yield the desired product. Alternatively, it can be desirable to employ, in the place of the ultimately desired substituent, a suitable group that can be carried through the reaction scheme and replaced as appropriate with the desired substituent. Unless otherwise specified, the variables are as defined above in reference to Formula (I). Reactions can be performed between the melting point and the reflux temperature of the solvent, and preferably between 0° C. and the reflux temperature of the solvent. Reactions can be heated employing conventional heating or microwave heating. Reactions can also be conducted in sealed pressure vessels above the normal reflux temperature of the solvent.

Compounds of Formula (I) can be converted to their corresponding salts using methods known to one of ordinary skill in the art. For example, an amine of Formula (I) can be treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts can be obtained as a result of reverse phase HPLC purification conditions. Crystalline forms of pharmaceutically acceptable salts of compounds of Formula (I) can be obtained in crystalline form by recrystallization from polar solvents (including mixtures of polar solvents and aqueous mixtures of polar solvents) or from non-polar solvents (including mixtures of non-polar solvents).

Where the compounds according to this disclosure have at least one chiral center, they can accordingly exist as enantiomers. Where the compounds possess two or more chiral centers, they can additionally exist as diastereomers. It is to be understood that all such isomers and mixtures thereof are encompassed within the scope of the present disclosure.

Compounds prepared according to the schemes described below can be obtained as single forms, such as single enantiomers, by form-specific synthesis, or by resolution. Compounds prepared according to the schemes below can alternately be obtained as mixtures of various forms, such as racemic (1:1) or non-racemic (not 1:1) mixtures. Where racemic and non-racemic mixtures of enantiomers are obtained, single enantiomers can be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers can be separated using conventional methods such as chromatography or crystallization.

SCHEME 1

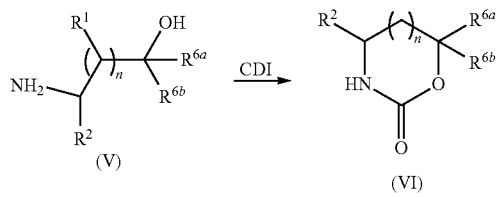

According to SCHEME 1, a compound of formula (VI), where $R^2$, n, $R^{6a}$, and $R^{6b}$ are as defined in the Summary, is commercially available or synthetically accessible from a compound of formula (V). A compound of formula (V), where n is 0 or 1; $R^2$ is H or alkyl; $R^{6a}$ and $R^{6b}$ are independently H or alkyl, can be cyclized with a reagent such as CDI, triphosgene, diethyl carbonate, and the like; in a suitable solvent such as THF, DCM, DMF, and the like; at temperatures ranging from room temperature to 100° C.; for a period of 1 h to 2 days; to provide a compound of formula (VI). In a preferred embodiment the reagent employed for cyclization is CDI, the solvent is THF and the reaction is stirred at room temperature for 2 days.

SCHEME 2

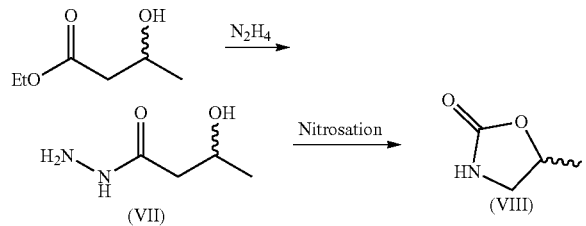

According to SCHEME 2, a compound of formula (VII) is synthetically accessible from commercially available, enantiopure starting material ethyl (R)-3-hydroxybutanoate or ethyl (S)-3-hydroxybutanoate, by reaction with hydrazine. In a preferred embodiment, the reagent employed for hydrazide formation is hydrazine, the solvent is EtOH, and the reaction is stirred at 90° C. for 16 h, to give a compound of formula (VII). A compound of formula (VII) can undergo a nitrosation followed by cyclization, under acidic conditions, such as sodium nitrite and $H_2SO_4$, in a solvent such as water, at temperatures ranging from 0° C. to room temperature, for a period of 2 h to provide a compound of formula (VIII).

SCHEME 3

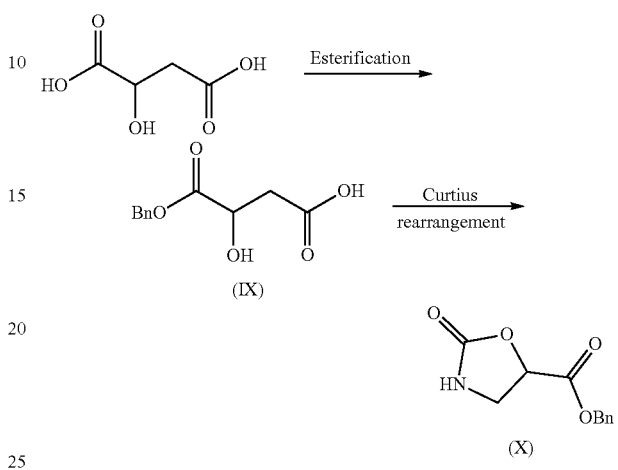

According to SCHEME 3, a compound of formula (IX), is synthetically accessible from commercially available DL-malic acid through selective monoesterification of the diacid. In a preferred embodiment, DL-malic acid is treated with trifluoroacetic anhydride at room temperature for 40 min, followed by exposure to benzyl alcohol at room temperature for 16 h. A compound of formula (IX) can undergo a Curtius rearrangement to give a compound of formula (X). In a preferred embodiment, the conditions used for the Curtius rearrangement are diphenyl phosphoryl azide (DPPA), trimethylamine, t-BuOH, and the reaction mixture is refluxed for 4 h.

SCHEME 4

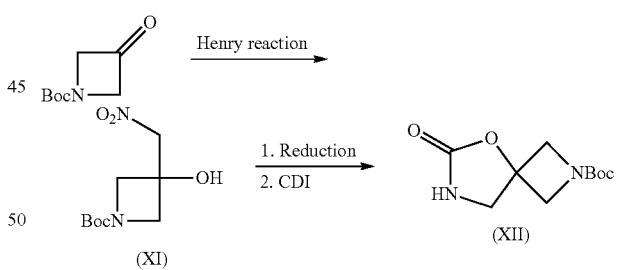

According to SCHEME 4, a compound of formula (XI) is synthetically accessible through a Henry reaction of commercially available tert-butyl 3-oxoazetidine-1-carboxylate. In a preferred embodiment, the conditions used are nitromethane, triethylamine, EtOH, and the reaction mixture is stirred at room temperature for 16 h. A compound of formula (XI) can be transformed to a compound of formula (XII), by reduction of the nitro group followed by cyclization, for example, as described in SCHEME 1. In a preferred embodiment, a compound of formula (XI) is reduced with Pd/C under a hydrogen atmosphere in MeOH at 50° C. for 16 h. The amino alcohol intermediate can then be cyclized with a reagent such as CDI, triphosgene, diethyl carbonate, and the like; in a suitable solvent such as THF, DCM, DMF, and the like; at temperatures ranging from room temperature to 100° C.; for a period of 1 h to 2 days; to provide a compound of formula (XII).

SCHEME 5

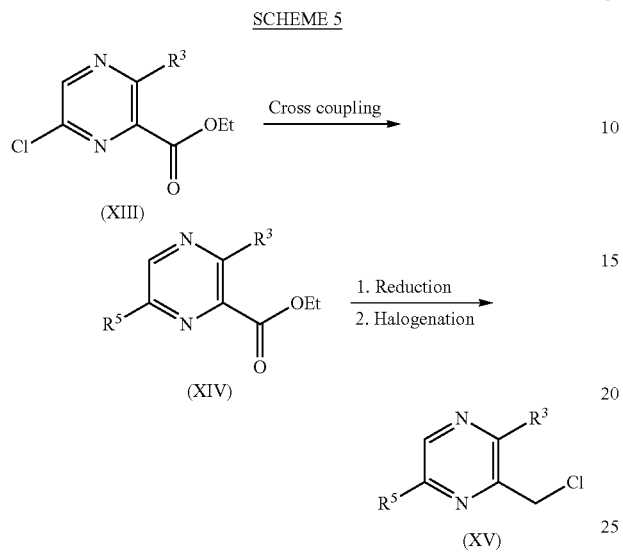

According to SCHEME 5, a compound of formula (XIII), where $R^3$ is H, is reacted in a metal-mediated cross coupling reaction such as a Suzuki reaction, to provide a compound of formula (XIV). For example, a compound of formula (XIV), where $R^3$ is H and $R^5$ is defined as in the Summary, can be reacted with a commercially available or synthetically accessible suitably substituted aryl boronic acid or boronic ester; in the presence of a palladium catalyst such as $Pd(PPh_3)Cl_2$, RuPhos Pd G3, $Pd(PPh_3)_4$, $Pd(dppf)Cl_2$, $PdCl_2(dppf)\text{-}CH_2Cl_2$, $PdCl_2(dtbpf)$, and the like; a suitable base such as $Na_2CO_3$, $Cs_2CO_3$, $K_2CO_3$, and the like; in a solvent such as 1,4-dioxane, water, or a mixture thereof; employing conventional or microwave heating; at temperatures ranging from room temperature to 90° C.; for a period of 1 h to overnight, to give a compound of formula (XIV), where $R^3$ is H and $R^5$ is as defined in the Summary. A compound of formula (XIV), where $R^3$ is H and $R^5$ is as defined in the Summary, can be reduced with a reducing agent such as $NaBH_4$, $LiAlH_4$, $LiBH_4$, diisobutylaluminum hydride (DIBAL or DIBAL-H), and the like; in a suitable solvent such as tetrahydrofuran (THF), methanol (MeOH), ethanol (EtOH), and the like; at temperatures ranging from −78 to 0° C.; for a period of 30 min to 16 h; to provide the alcohol intermediate. The alcohol intermediate can be subsequently chlorinated with thionyl chloride; in a suitable solvent such as dichloroethane (DCE), and the like; at temperatures ranging from 0 to 60° C.; for a period of 30 min to 1 h; to provide a compound of formula (XV).

SCHEME 6

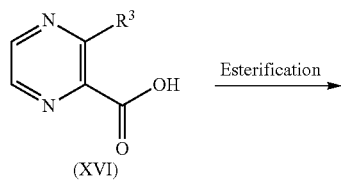

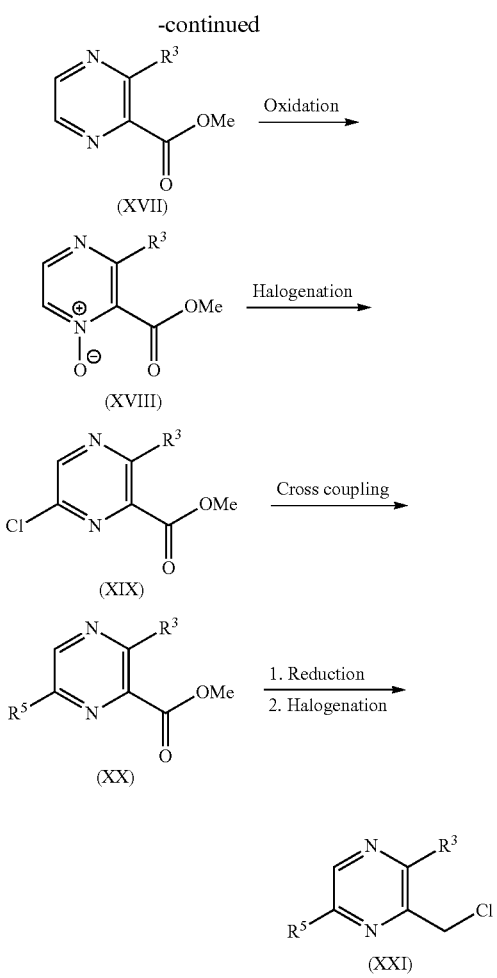

According to SCHEME 6, a compound of formula (XVI), where $R^3$ is Me, is esterified to provide a compound of formula (XVII). For example, a compound of formula (XVI) can be treated with $H_2SO_4$ in methanol and stirred at 60° C. for 4 h. A compound of formula (XVII) can be converted to the N-oxide by reaction with an oxidizing agent to give a compound of formula (XVIII), where $R^3$ is Me. For example, a compound of formula (XVII) in DCM can be treated with hydrogen peroxide-urea adduct at 0° C., followed by trifluoroacetic anhydride at 0° C.; at temperatures ranging from 0° C. to room temperature overnight, to give a compound of formula (XVIII). A compound of formula (XVIII) can be treated with a chlorinating agent, such as $POCl_3$, $SOCl_2$, $PCl_5$, and the like, in a suitable solvent such as DMF or toluene, at a temperature of 60 to 100° C. for 12 to 24 h, to provide a compound of formula (XIX), where $R^3$ is Me. A compound of formula (XIX) can then be reacted under metal mediated cross coupling conditions as previously described, with an aryl boronic ester or boronic acid to afford a compound of formula (XX), where $R^3$ is Me and $R^5$ is as defined in the Summary. A compound of formula (XXI), where $R^3$ is Me and $R^5$ is as defined in the Summary, can be prepared in two steps from a compound of formula (XX), employing reduction and halogenation conditions previously described.

SCHEME 7

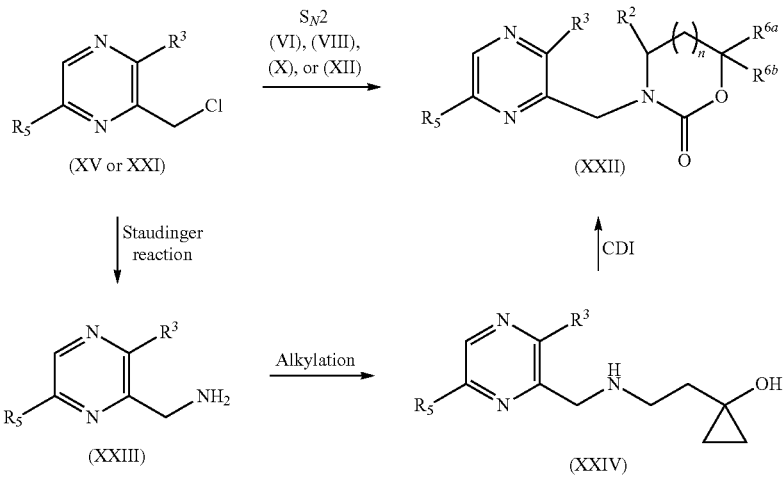

According to SCHEME 7, a compound of formula (XV) or (XXI), where $R^3$ is H or Me, and $R^5$ is as defined in the Summary; can be reacted with a commercially available or synthetically accessible carbamate of formula (VI), where $R^2$, n, $R^{6a}$ an $R^{6b}$ are as defined in the Summary, (VIII), (X), or (XII); in the presence of a base such as NaH, $K_2CO_3$, $Cs_2CO_3$, and the like; in a solvent such as dimethylformamide (DMF), DCM, and the like; for a period of 30 min to 18 h; at room temperature; to provide a compound of formula (XXII).

When a compound of formula (X) is used in the $S_N2$ step, deprotection of the tert-butyloxycarbonyl protecting group of tert-butyl 6-oxo-5-oxa-2,7-diazaspiro[3.4]octane-2-carboxylate, can be accomplished by methods known to one skilled in the art. For example, a compound of formula (XXII), where $R^3$ is H or Me, and $R^5$ is as defined in the Summary, with tert-butyl 6-oxo-5-oxa-2,7-diazaspiro[3.4]octane-2-carboxylate attached, can be deprotected under acidic conditions, such as trifluoracetic acid, and the like; in a solvent such as DCM, and the like; at 0° C. to room temperature. The deprotected product of a compound of formula (XXII) can undergo further reaction with an alkylating agent, such as methyl iodide, in the presence of a base, such as NaH.

When a compound of formula (XII) is used in the $S_N2$ step, saponification of the ester under basic, aqueous conditions, such as aqueous lithium hydroxide (LiOH), gives the intermediate acid. The intermediate acid can then be transformed to the amide using conditions known to one skilled in the art. A compound of formula (XXII), where $R^3$ is H or Me, and $R^5$ is as defined in the Summary; bearing an ester at $R^{6a}$ or $R^{6b}$, can undergo an amide coupling reaction of the intermediate acid and an amine, such as azetidine, methylamine, dimethylamine, and the like; in a solvent such as DMF, DCM, and the like; at room temperature; in the presence of a dehydrating agent such as HATU, hydroxybenzotriazole/1-ethyl-3-(3-dimethylaminopropyl)carbodiimide (HOBt/EDCI), and the like to afford a compound of formula (XXII) bearing an amide at $R^{6a}$ or $R^{6b}$. Alternatively, the amide can be obtained from the intermediate acid through generation of the acid chloride using oxalyl chloride, followed by nucleophilic attack with an amine, such as azetidine, methylamine, dimethylamine, and the like; in a solvent such as DMF, DCM, and the like; at room temperature.

Alternatively, a compound of formula (XV) or (XXI), where $R^3$ is H or Me, and $R^5$ is as defined in the Summary; can undergo a Staudinger reaction to give a compound of formula (XXIII). In a preferred embodiment, the conditions used are sodium azide in DMF, and the reaction is stirred at rt for 18 h. The azide intermediate is then treated with triphenylphosphine in THF, and the reaction is stirred at rt for 16 h. Aqueous workup leads to the amine, a compound of formula (XXIII), where $R^3$ is H or Me, and $R^5$ is as defined in the Summary. A compound of formula (XXIII), can then undergo an alkylation, with an alkylating agent such as 1-(2-chloroethyl)cyclopropan-1-ol, and the like, with an additive such as potassium iodide (KI), and the like, with a base such as $K_2CO_3$, and the like, in a suitable solvent such as acetonitrile, and the like, to provide a compound of formula (XXIV). A compound of formula (XXIV), where $R^3$ is Me and $R^5$ is as defined in the Summary, can be cyclized using conditions previously described above to give a compound of formula (XXII).

SCHEME 8

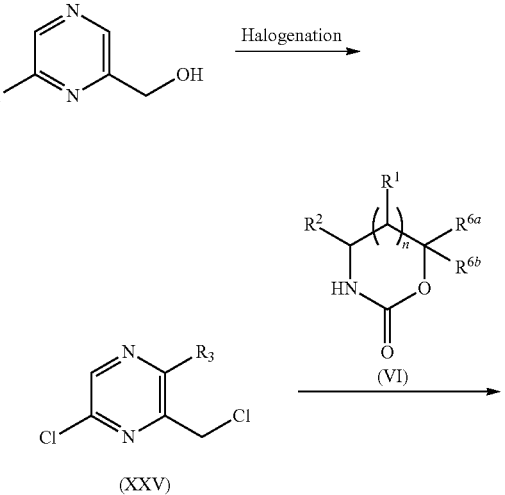

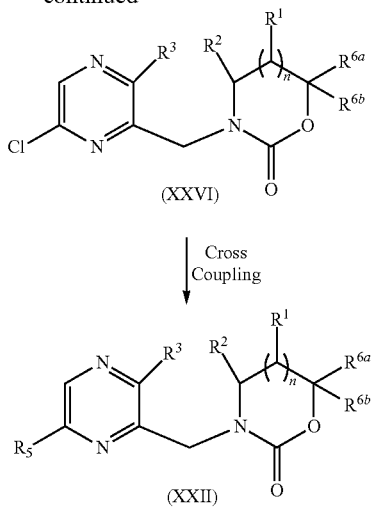

According to SCHEME 8, a compound of formula (XXV), where $R^3$ is H, is accessible from (6-chloropyrazin-2-yl)methanol through chlorination with a chlorinating reagent such as thionyl chloride, and the like; in a suitable solvent such as dichloromethane (DCM), and the like; at temperatures ranging from 0 to 30° C.; for a period of 30 min to 48 h; to provide a compound of formula (XXV). An $S_N2$ reaction of a compound of formula (XXV), with a commercially available or synthetically accessible carbamate of formula (VI); in the presence of a base such as $Na_2CO_3$, NaH, $K_2CO_3$, $Cs_2CO_3$, and the like; in a solvent such as DMF, ACN, DCM, and the like; for a period of 30 min to 18 hours; at room temperature; provides a compound of formula (XXVI), where $R^3$ is H, and $R^2$, n, $R^{6a}$ an $R^{6b}$ are as defined in the Summary. A compound of formula (XXVI) can be reacted in a metal mediated cross coupling reaction as previously described, with a commercially available or synthetically accessible differentially substituted aryl boronic acid or boronic ester to provide a compound of Formula (XXII), where $R^3$ is Me and $R^5$ is as defined in the Summary.

5. EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel ($SiO_2$) using prepacked cartridges.

Preparative reverse-phase high performance liquid chromatography (RP HPLC) was performed with:
Method A. A Gilson HPLC with an XBridge C18 column (5 µm, 50×100 mm or 50×250 mm), mobile phase of 5-99% ACN in 20 mM $NH_4OH$ over 10 min and then hold at 99% ACN for 2 min, at a flow rate of 80 mL/min.
or
Method B. A Teledyne ACCQPrep HP125 with an XBridge C18 column (5 µm, 50×100 mm or 50×250 mm), mobile phase of 0-100% ACN in 20 mM $NH_4OH$ over 16 min or 42 min and then hold at 100% ACN for 2 min, at a flow rate of 80 mL/min.
or
Method C. A Teledyne ACCQPrep HP125 with a Sunfire Prep C18 column (5 µm, 30×250 mm), mobile phase of 5-100% ACN with 0.05% TFA in water with 0.05% TFA over 22 min and then hold at 100% ACN for 2 min, at a flow rate of 42.5 mL/min.
or
Method D. A Gilson HPLC with a Phenomenex C18 column (5 µm, 21.2×100 mm), mobile phase of 0.1% HCOOH and ACN:MeOH (1:1).
or
Method E. A Gilson HPLC with a Phenomenex C18 column (5 µm, 21.2×100 mm), mobile phase of water (25 mM $NH_4HCO_3$) and ACN:MeOH (1:1).
or
Method F. A Gilson HPLC with a Phenomenex C18 column (5 µm, 21.2×100 mm), mobile phase of 65 mM $NH_4OAc$: ACN (9:1) and ACN:MeOH (1:1).

Preparative supercritical fluid high performance liquid chromatography (SFC) was performed on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

All the LC/MS analyses were performed using an Agilent G1956A LC/MS quadrupole coupled to an Agilent 1100 series liquid chromatography (LC) system consisting of a binary pump with degasser, autosampler, thermostated column compartment, and diode array detector. The mass spectrometer (MS) was operated with an atmospheric pressure electrospray ionization (API-ES) source in positive ion mode. The capillary voltage was set to 3000 V and the fragmentor voltage to 70 V, and the quadrupole temperature was maintained at 100° C. The drying gas flow and temperature values were 12.0 L/min and 350° C., respectively. Nitrogen was used as the nebulizer gas at a pressure of 35 psi. Data acquisition was performed with Agilent Chemstation software. Analyses were carried out on a YMC pack ODS-AQ C18 column (50 mm long×4.6 mm ID; 3 µm particle size) at 35° C., with a flow rate of 2.6 mL/min. A gradient elution was performed from 95% (water+0.1% formic acid)/5% acetonitrile to 5% (water+0.1% formic acid)/95% acetonitrile in 4.8 min; the resulting composition was held for 1.0 min; from 5% (water+0.1% formic acid)/ 95% acetonitrile to 95% (water+0.1% formic acid)/5% acetonitrile in 0.2 min. The standard injection volume was 2 µL. Acquisition ranges were set to 190-400 nm for the UV-PDA detector and 100-1400 m/z for the MS detector.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, Mass.) or OEMetaChem V1.4.0.4 (Open Eye).

Compounds designated as R* or S* are enantiopure compounds where the absolute configuration was not determined.

5.1. Intermediates: Intermediates 1-27

Intermediate 1: 4-Oxa-6-azaspiro[2.4]heptan-5-one

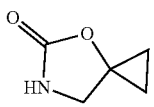

In a round bottom flask, a mixture of 1-(aminomethyl)-cyclopropanol (0.2 g, 2.3 mmol, 1 equiv), CDI (0.37 g 2.3 mmol, 1 equiv) and THF (10 mL) was stirred at room temperature for 16 h. The reaction mixture was concentrated under reduced pressure, and the crude was purified by flash column chromatography (silica, AcOEt in heptane from 0/100 to 30/70) to give the title compound (183 mg, 1.6 mmol, 70%) as an off white solid. MS (ESI): mass calcd. for $C_5H_7NO_2$, 113.1; m/z found, 114 $[M+H]^+$.

Intermediate 2: (R)-5-Methyloxazolidin-2-one

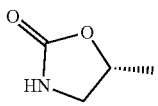

Step A: (R)-3-hydroxybutanehydrazide. In a round bottom flask, ethyl (R)-(-)-3-hydroxybutyrate (0.49 mL, 3.8 mmol, 1 equiv) was dissolved in ethanol (4 mL), and then hydrazine monohydrate (0.44 g, 5.7 mmol, 64%, 1.5 equiv) was added at room temperature. The reaction mixture was then heated to 90° C. for 16 h. Upon completion, the crude reaction was concentrated under vacuum and a white solid precipitated. The precipitate was filtered and washed with diethyl ether. The solid was dried under vacuum to give the title compound (413 mg, 3.5 mmol, 92%) as an off white solid. MS (ESI): mass calcd. for $C_4H_{10}N_2O_2$, 118.1; m/z found, 119 $[M+H]^+$.

Step B: (R)-5-Methyloxazolidin-2-one. In a round bottom flask, a solution of (R)-3-hydroxybutanehydrazide (0.41 g, 3.5 mmol, 1 equiv) in water (5 mL) was cooled to 0° C., and a solution of $H_2SO_4$ (0.28 mL, 5.2 mmol, 1.5 equiv) in 1 ml of water was added dropwise. Then, $NaNO_2$ (0.36 g, 5.2 mmol, 1.5 equiv) was added portion-wise and the reaction mixture was stirred at room temperature for 2 h. Ethanol was added and the reaction mixture was concentrated under reduced pressure. The residue was filtered and washed with AcOEt. The filtrate was collected and concentrated under reduced pressure to afford the title compound (200 mg, 1.98 mmol, 57%) as a colorless oil. MS (ESI): mass calcd. for $C_4H_7NO_2$, 101.1; m/z found, 102 $[M+H]^+$.

Intermediate 3: (S)-5-Methyloxazolidin-2-one

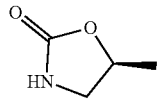

Prepared analogous to (R)-5-Methyloxazolidin-2-one (Intermediate 2), using (S)-3-hydroxybutanehydrazide in Step A. MS (ESI): mass calcd. for $C_4H_7NO_2$, 101.1; m/z found, 102 $[M+H]^+$.

Intermediate 4: 1-(2-Chloroethyl)cyclopropan-1-ol

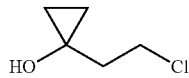

In a round bottom flask, ethylmagnesium bromide (6.66 mL, 20.0 mmol, 3 M in diethyl ether, 3 equiv) was added dropwise to a solution of ethyl 3-chloropropionate (1 mL, 6.7 mmol, 1 equiv) and titanium (IV) isopropoxide (0.197 mL, 0.67 mmol, 0.1 equiv) in $Et_2O$ (8 mL) at 0° C. Then, the reaction mixture was stirred at 0° C. for 2 h. The reaction mixture was quenched with $H_2SO_4$ (aq, 10%) at 0° C. The two layers were separated, and the organic layer was washed with water, a saturated aqueous solution of $NaHCO_3$ and brine, dried over $MgSO_4$, and filtered. The combined organics were evaporated under vacuum, keeping the temperature of the bath below 35° C., to afford the title compound (858 mg, 6.4 mmol, 96%) as a yellow oil. The title compound was used immediately without further purification. Decomposition of the product was observed within hours.

Intermediate 5: (R/S)-Benzyl 2-oxooxazolidine-5-carboxylate

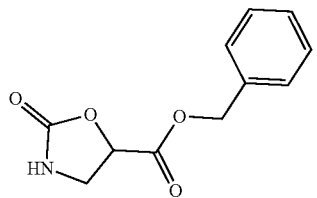 [SMILES: O=C1NCC(C(=O)OCc2ccccc2)O1]

Step A: 4-(Benzyloxy)-3-hydroxy-4-oxobutanoic acid. In round bottom flask, a mixture of DL-malic acid (5 g, 37.3 mmol, 1 equiv) and trifluoroacetic anhydride (22 mL, 158.3 mmol, 4.2 equiv) was stirred at rt for 40 min. Then, excess trifluoroacetic anhydride was removed under vacuum. Benzyl alcohol (22 mL, 212.6 mmol, 5.7 equiv) was added to the residue, and the mixture was stirred at rt for 16 h. The reaction was concentrated under vacuum and the crude was purified by chromatography (silica; AcOEt in heptane 0/100 to 40/60) to give the title compound (6.79 g, 30.3 mmol, 81%). $^1$H NMR (300 MHz, $CDCl_3$) δ 7.35 (s, 5H), 5.23 (s, 2H), 4.54 (s, 1H), 3.02-2.74 (m, 2H).

Step B: (R/S)-Benzyl 2-oxooxazolidine-5-carboxylate. In a round bottom flask equipped with a condenser, diphenyl phosphoryl azide (3.6 mL, 16.7 mmol, 1.1 equiv) and trimethylamine (2.3 mL, 16.7 mmol, 1.1 equiv) were added to a solution of 4-(benzyloxy)-3-hydroxy-4-oxobutanoic acid (3.4 g, 15.2 mmol, 1 equiv) in tert-butanol (76 mL). The reaction mixture was refluxed for 4 h and then cooled down to rt. The solvent was removed under reduced pressure, the residue was dissolved in EtOAc and washed with a sat. aq. solution of NaHCO$_3$ and water. The organics were separated and dried over MgSO$_4$, filtered, and concentrated under vacuum. The crude product was purified by chromatography (silica; AcOEt in heptane 0/100 to 100/0) to give the title compound (2.14 g, 9.2 mmol, 61%). MS (ESI): mass calcd. for C$_{11}$H$_{11}$NO$_4$, 221.1; m/z found, 222 [M+H]$^+$. $^1$H NMR (300 MHz, DMSO-d$_6$) δ 7.37 (s, 5H), 5.66 (s, 1H), 5.26 (s, 2H), 5.05 (dd, J=9.2, 5.5 Hz, 1H), 3.94-3.61 (m, 2H).

Intermediate 6: tert-Butyl 6-oxo-5-oxa-2,7-diazaspiro[3.4]octane-2-carboxylate

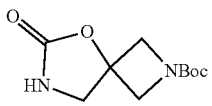

Step A: 3-Hydroxy-3-nitromethyl-azetidine-1-carboxylic acid tert-butyl ester. In a round bottom flask, nitromethane (3.6 mL, 66.5 mmol, 3.8 equiv), and TEA (488 μL, 3.5 mmol, 0.2 equiv) were added to a solution of tert-butyl 3-oxoazetidine-1-carboxylate (3 g, 17.5 mmol, 1 equiv) in EtOH (12 mL), and the reaction mixture was stirred at rt for 16 h. The crude mixture was concentrated under vacuum to yield the title compound (4 g, 17.2 mmol, 98%) as a white solid. The product was used in the next step without further purification. $^1$H NMR (300 MHz, CDCl$_3$) δ 4.70 (s, 2H), 3.99 (s, 4H), 3.73 (s, 1H), 1.44 (s, 9H).

Step B: 3-Aminomethyl-3-hydroxy-azetidine-1-carboxylic acid tert-butyl ester. In a round bottom flask, Pd/C (400 mg, 10%) was added to a solution of 3-hydroxy-3-nitromethyl-azetidine-1-carboxylic acid tert-butyl ester (4 g, 17.2 mmol, 1 equiv) in MeOH (80 mL). The reaction mixture was stirred at 50° C. for 16 hours under a hydrogen atmosphere. Then, the reaction mixture was filtered through Celite® and evaporated under vacuum to give the title compound (3.9 g, 17.0 mmol, 99%). The product was used in the next step without further purification.

Step C: Tert-butyl 6-oxo-5-oxa-2,7-diazaspiro[3.4]octane-2-carboxylate. Prepared analogous to 4-Oxa-6-azaspiro[2.4]heptan-5-one (Intermediate 1), using 3-aminomethyl-3-hydroxy-azetidine-1-carboxylic acid tert-butyl ester from Step B. $^1$H NMR (300 MHz, CDCl$_3$) δ 5.43 (s, 1H), 4.30 (d, J=9.9 Hz, 2H), 4.02 (d, J=9.9 Hz, 2H), 3.79 (s, 2H), 1.44 (s, 9H).

Intermediate 7: 2-(Chloromethyl)-6-(3-(difluoromethyl)-4-fluorophenyl)pyrazine

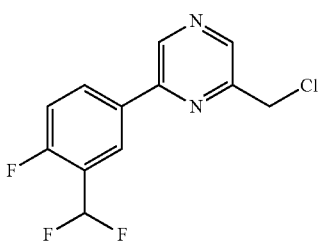 [SMILES: Fc1ccc(-c2cncc(CCl)n2)cc1C(F)F]

Step A: Ethyl 6-(3-(difluoromethyl)-4-fluorophenyl)pyrazine-2-carboxylate. In a sealed tube, a mixture of ethyl-6-chloropyrazine-2-carboxylate (0.6 g, 3.5 mmol, 1 equiv), 2-(3-(difluoromethyl)-4-fluorophenyl)-4,4,5,5-tetramethyl-1,3,2-dioxaborolane (Intermediate 23) (1.1 g, 4.2 mmol, 1.2 equiv), sodium carbonate (0.79 g, 7.4 mmol, 2.1 equiv), water (3 mL), and 1,4-dioxane (12 mL) was purged with nitrogen for 5 min. Then, bis(triphenylphosphine)palladium (II) dichloride (0.12 g, 0.2 mmol, 0.05 equiv) was added, and the reaction mixture was stirred overnight at 90° C. Upon completion, the reaction mixture was cooled down to room temperature. LCMS analysis showed partial hydrolysis of the ester group. To recover the ester group, the crude reaction mixture was concentrated under vacuum, and ethanol (25 mL) and H$_2$SO$_4$ (few drops) were added and the reaction was stirred at 80° C. for 2 h. Then, the mixture was diluted with water and extracted with dichloromethane (3×50 mL). The combined organics were dried over MgSO$_4$, filtered, and the solvents were evaporated under vacuum. The crude product was purified by flash column chromatography (silica; AcOEt in heptane 0/100 to 100/0) to give the title compound (900 mg, 3.04 mmol, 87%) as a pale yellow solid. MS (ESI): mass calcd. for C$_{14}$H$_{11}$F$_3$N$_2$O$_2$, 296.1; m/z found, 297 [M+H]$^+$.

Step B: (6-(3-(Difluoromethyl)-4-fluorophenyl)pyrazin-2-yl)methanol. In a round bottom flask, lithium aluminum hydride (0.115 g, 3 mmol, 1 equiv) was added portion-wise to a suspension of ethyl 6-(3-(difluoromethyl)-4-fluorophenyl)pyrazine-2-carboxylate (0.9 g, 3 mmol, 1 equiv) in dry THF (40 mL) at 0° C. and stirred for 30 min. Then, water and ethyl acetate was slowly added at 0° C., followed by al 0% aqueous solution of NaOH (13 mL) and water (26 mL). The layers were separated, and the aqueous layer was further extracted with ethyl acetate (3×50 mL). The combined organics were dried over MgSO$_4$, filtered, and the solvents evaporated. The crude product was purified by flash column chromatography (silica; EtOAc in heptane, from 0/100 to 30/70) to give the title compound (234 mg, 0.83 mmol, 27%) as a yellow solid. MS (ESI): mass calcd. for C$_{12}$H$_9$F$_3$N$_2$O, 254.1; m/z found, 256 [M+H]$^+$.

Step C: 2-(Chloromethyl)-6-(3-(difluoromethyl)-4-fluorophenyl)pyrazine. In a round bottom flask, thionyl chloride (116.43 μL, 1.6 mmol, 1.5 equiv) was added to a solution of (6-(3-(difluoromethyl)-4-fluorophenyl)pyrazin-2-yl)methanol (0.27 g, 1.1 mmol, 1 equiv) in dry 1,2-dichlorethane (4 mL) at room temperature. The resulting mixture was stirred at 60° C. for 1 h. Then, the reaction mixture was concentrated under vacuum and water and dichloromethane were added. The organic layer was separated, dried over MgSO$_4$, filtered, and concentrated to yield the title compound (264 mg, 0.97 mmol, 90%) as a brown oil. The product was used without further purification.

Intermediate 8: 2-(Chloromethyl)-6-(3-(difluoromethoxy)-4-fluorophenyl)pyrazine

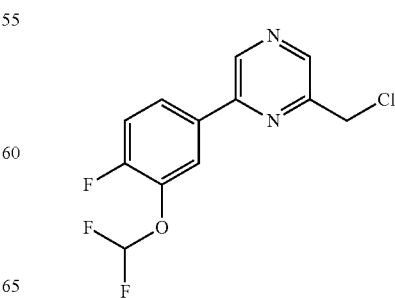

Prepared analogous to 2-(Chloromethyl)-6-(3-(difluoromethyl)-4-fluorophenyl) pyrazine (Intermediate 7), using 2-(3-(difluoromethoxy)-4-fluorophenyl)-4,4,5,5-tetramethyl-1,3,2-dioxaborolane (Intermediate 26) in Step A. MS (ESI): mass calcd. for $C_{12}H_8ClF_3N_2O$, 288.0; m/z found, 289 [M+H]$^+$.

Intermediate 9: 2-(4-Chloro-3-(difluoromethoxy)phenyl)-6-(chloromethyl)pyrazine

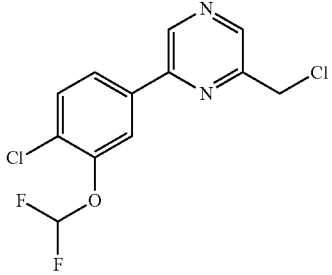 [SMILES: FC(F)Oc1cc(-c2cncc(CCl)n2)ccc1Cl]

Prepared analogous to 2-(Chloromethyl)-6-(3-(difluoromethyl)-4-fluorophenyl) pyrazine (Intermediate 7), using 2-(4-chloro-3-(difluoromethoxy)phenyl)-4,4,5,5-tetramethyl-1,3,2-dioxaborolane (Intermediate 27) in Step A.

Intermediate 10: 2-(Chloromethyl)-6-(3-(1,1-difluoroethyl)phenyl)pyrazine

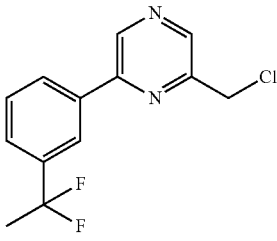 [SMILES: CC(F)(F)c1cccc(-c2cncc(CCl)n2)c1]

Prepared analogous to 2-(Chloromethyl)-6-(3-(difluoromethyl)-4-fluorophenyl) pyrazine (Intermediate 7), using 2-(3-(1,1-difluoroethyl)phenyl)-4,4,5,5-tetramethyl-1,3,2-dioxaborolane (Intermediate 25) in Step A.

Intermediate 11: 2-(Chloromethyl)-6-(3-(1,1-difluoroethyl)-4-fluorophenyl)pyrazine

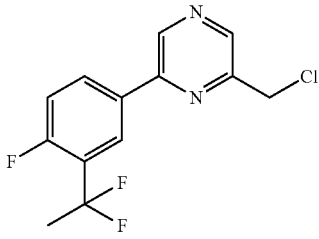 [SMILES: CC(F)(F)c1cc(-c2cncc(CCl)n2)ccc1F]

Prepared analogous to 2-(Chloromethyl)-6-(3-(difluoromethyl)-4-fluorophenyl) pyrazine (Intermediate 7), using 2-(3-(1,1-difluoroethyl)-4-fluorophenyl)-4,4,5,5-tetramethyl-1,3,2-dioxaborolane (Intermediate 24) in Step A. MS (ESI): mass calcd. for $C_{13}H_{10}ClF_3N_2$, 286.1; m/z found, 287 [M+H]$^+$.

Intermediate 12: 3-(Chloromethyl)-5-(3-(1,1-difluoroethyl)phenyl)-2-methylpyrazine

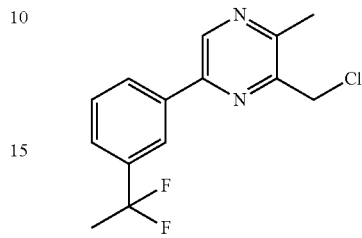

Step A: Methyl 3-methylpyrazine-2-carboxylate. To a solution of 3-methylpyrazine-2-carboxylic acid (6 g, 43.4 mmol, 1 equiv) in methanol (60 mL) at 0° C. was added $H_2SO_4$ (2.9 mL, 54.3 mmol, 1.25 equiv) dropwise, and the reaction mixture was stirred at 60° C. for 4 h. The solvent was evaporated, and the residue was dissolved in water (5 ml) and basified with a 10% aq. $Na_2CO_3$ solution to pH 12. The solution was extracted with AcOEt. The combined organic layers were dried over $MgSO_4$, filtered and the solvents evaporated under vacuum to give the title compound (5.75 g, 37.8 mmol, 87%), which was used in the next step without further purification. $^1H$ NMR (300 MHz, CDCl$_3$) δ 8.61 (s, 1H), 8.51 (s, 1H), 4.01 (s, 3H), 2.85 (s, 3H).

Step B: 2-(Methoxycarbonyl)-3-methylpyrazine 1-oxide. In a round bottom flask, hydrogen peroxide-urea adduct (5.3 g, 56.7 mmol, 1.5 equiv) was added to a solution of methyl 3-methylpyrazine-2-carboxylate (5.75 g, 37.8 mmol, 1 equiv) in DCM (100 mL) at 0° C. Then, trifluoroacetic anhydride (7.9 mL, 56.7 mmol 1.5 equiv) was added dropwise to the reaction at 0° C. The reaction mixture was stirred at 0° C. for 1 h, warmed to rt and stirred overnight. The crude reaction was dissolved with DCM and washed with a saturated aqueous solution of $Na_2SO_3$. The organic layer was separated, dried over $MgSO_4$, filtered, and the solvents evaporated under reduced pressure. The crude product was purified by flash column chromatography (silica; AcOEt in heptane 0/100 to 30/70) to give the title compound (350 mg, 1.977 mmol, 5%) as a pale yellow solid. $^1H$ NMR (300 MHz, CDCl$_3$) δ 8.37 (d, J=3.5 Hz, 1H), 7.99 (d, J=3.5 Hz, 1H), 4.03 (s, 3H), 2.52 (s, 3H).

Step C: Methyl 6-chloro-3-methylpyrazine-2-carboxylate. To a solution of 2-(methoxycarbonyl)-3-methylpyrazine 1-oxide (0.35 g 2.1 mmol, 1 equiv) in dry toluene (7 mL) at 0° C., was added phosphorus(V) oxychloride (0.39 mL, 4.2 mmol, 2 equiv) and DMF (0.016 mL, 0.2 mmol, 0.1 equiv). The reaction mixture was stirred at 70° C. for 24 h. Then, the reaction mixture was cooled down to room temperature and a saturated aqueous solution of NaHCO$_3$. AcOEt were added and the aqueous layer was extracted several times. The organic phases were combined, dried over $MgSO_4$, filtered, and the solvents removed under vacuum. The crude was purified by flash column chromatography (silica; AcOEt in heptane 0/100 to 50/50) to give the title compound (200 mg, 1.07 mmol, 52%) as a pale yellow solid. $^1H$ NMR (300 MHz, DMSO-d$_6$) δ 8.89 (s, 1H), 3.91 (s, 3H), 2.72 (s, 3H).

Step D: Methyl 6-(3-(1,1-difluoroethyl)phenyl)-3-methylpyrazine-2-carboxylate. Prepared analogous to Step A of the synthesis of Intermediate 7 using methyl 6-chloro-3-methylpyrazine-2-carboxylate and (3-(1,1-difluoroethyl)phenyl)boronic acid. $^1$H NMR (300 MHz, CDCl$_3$) δ 9.04 (s, 1H), 8.13 (s, 1H), 8.08 (s, 1H), 7.65-7.52 (m, 2H), 4.04 (s, 3H), 2.86 (s, 3H), 1.99 (t, J=18.2 Hz, 3H).

Step E: (6-(3-(1,1-Difluoroethyl)phenyl)-3-methylpyrazin-2-yl)methanol. Prepared analogous to Step B of the synthesis of Intermediate 7 using methyl 6-(3-(1,1-difluoroethyl)phenyl)-3-methylpyrazine-2-carboxylate. $^1$H NMR (300 MHz, CDCl$_3$) δ 8.87 (s, 1H), 8.15 (s, 1H), 8.11-8.02 (m, 1H), 7.65-7.53 (m, 2H), 4.84 (s, 2H), 2.54 (s, 3H), 2.14-1.84 (m, 3H).

Step F: 3-(Chloromethyl)-5-(3-(1,1-difluoroethyl)phenyl)-2-methylpyrazine. Prepared analogous to Step C of the synthesis of Intermediate 7 using (6-(3-(1,1-difluoroethyl)phenyl)-3-methylpyrazin-2-yl)methanol. $^1$H NMR (300 MHz, CDCl$_3$) δ 8.89 (s, 1H), 8.17 (s, 1H), 8.07 (d, J=6.6 Hz, 1H), 7.65-7.52 (m, 2H), 4.80 (s, 2H), 2.74 (s, 3H), 1.99 (t, J=18.1 Hz, 3H).

Intermediate 13: 3-(Chloromethyl)-5-(3-(difluoromethoxy)-4-fluorophenyl)-2-methylpyrazine

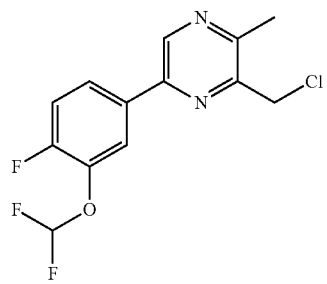 [SMILES: Cc1ncc(-c2ccc(F)c(OC(F)F)c2)nc1CCl]

Prepared analogous to 3-(Chloromethyl)-5-(3-(1,1-difluoroethyl)phenyl)-2-methylpyrazine (Intermediate 12), using 2-(3-(difluoromethoxy)-4-fluorophenyl)-4,4,5,5-tetramethyl-1,3,2-dioxaborolane (Intermediate 26) in Step D. $^1$H NMR (300 MHz, CDCl$_3$) δ 8.83 (s, 1H), 7.95 (dd, J=7.3, 2.0 Hz, 1H), 7.86 (ddd, J=8.6, 4.3, 2.2 Hz, 1H), 7.38-7.13 (m, 1H), 6.64 (t, J=73.3 Hz, 1H), 4.77 (s, 2H), 2.73 (s, 3H).

Intermediate 14: 3-(Chloromethyl)-5-(3-(difluoromethyl)-4-fluorophenyl)-2-methylpyrazine

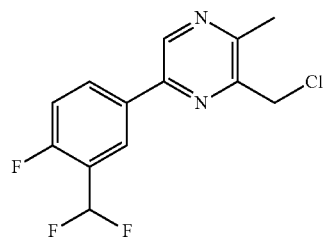 [SMILES: Cc1ncc(-c2ccc(F)c(C(F)F)c2)nc1CCl]

Prepared analogous to 3-(Chloromethyl)-5-(3-(1,1-difluoroethyl)phenyl)-2-methylpyrazine (Intermediate 12), using 2-(3-(difluoromethyl)-4-fluorophenyl)-4,4,5,5-tetramethyl-1,3,2-dioxaborolane (Intermediate 23) in Step D.

Intermediate 15: 5-(4-Chloro-3-(difluoromethoxy)phenyl)-3-(chloromethyl)-2-methylpyrazine

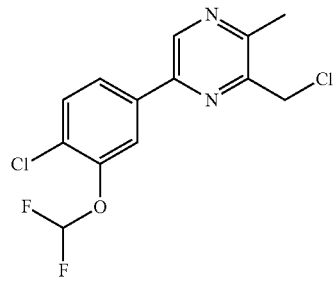 [SMILES: Cc1ncc(-c2ccc(Cl)c(OC(F)F)c2)nc1CCl]

Prepared analogous to 3-(Chloromethyl)-5-(3-(1,1-difluoroethyl)phenyl)-2-methylpyrazine (Intermediate 12), using 2-(4-chloro-3-(difluoromethoxy)phenyl)-4,4,5,5-tetramethyl-1,3,2-dioxaborolane (Intermediate 27) in Step D. MS (ESI): mass calcd. for $C_{13}H_{10}Cl_2F_2N_2O$, 318.0; m/z found, 319 [M+H]$^+$.

Intermediate 16: (6-(3-(1,1-Difluoroethyl)phenyl)pyrazin-2-yl)methanamine

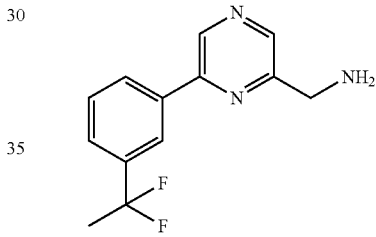

Step A: 2-(Azidomethyl)-6-(3-(1,1-difluoroethyl)phenyl)pyrazine. In a round bottom flask, sodium azide (0.135 g, 2.1 mmol, 2 equiv) was added to a solution of 2-(chloromethyl)-6-(3-(1,1-difluoroethyl)phenyl)pyrazine (Intermediate 10, 0.28 g, 1.04 mmol, 1 equiv) in DMF (6 mL), and the reaction mixture was stirred at rt for 18 h. Then, the reaction mixture was diluted with water and extracted with AcOEt. The organic phase was dried over MgSO$_4$, filtered, and concentrated to yield the title compound (280 mg, 1.01 mmol, 97%) as a brown oil, which was used without further purification. $^1$H NMR (300 MHz, DMSO-d$_6$) δ 9.34 (s, 1H), 8.69 (s, 1H), 8.35 (s, 1H), 8.34-8.26 (m, 1H), 7.76-7.63 (m, 2H), 4.69 (s, 2H), 2.03 (t, J=18.4 Hz, 3H).

Step B: (6-(3-(1,1-Difluoroethyl)phenyl)pyrazin-2-yl)methanamine. Triphenylphosphine (0.373 g, 1.4 mmol, 1.5 equiv) was added to a solution of 2-(azidomethyl)-6-(3-(1,1-difluoroethyl)phenyl)pyrazine (0.280 g, 1.01 mmol, 1 equiv) in dry THF (5 mL), and the reaction mixture was stirred at rt for 16 h. Then, water (2 mL) was added and the mixture was stirred at rt for 16 h. The solvents were evaporated under reduced pressure and the crude was purified by flash column chromatography (silica; gradient of DCM/MeOH/NH$_4$OH (9:1:0.25) in DCM from 0 to 60%) to give the title compound (200 mg, 0.8 mmol, 79%). $^1$H NMR (300 MHz, DMSO-d$_6$) δ 8.93 (s, 1H), 8.55 (s, 1H), 8.20 (s, 1H), 8.09 (d, J=6.6 Hz, 1H), 7.64-7.52 (m, 2H), 4.11 (s, 2H), 1.99 (t, J=18.2 Hz, 3H).

Intermediate 17: (6-(3-(Difluoromethoxy)-4-fluorophenyl)pyrazin-2-yl)methanamine

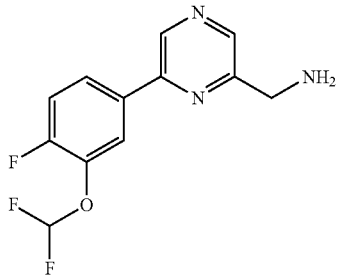 [SMILES: NCc1cncc(-c2ccc(F)c(OC(F)F)c2)n1]

Prepared analogous to (6-(3-(1,1-Difluoroethyl)phenyl)pyrazin-2-yl)methanamine (Intermediate 16), using 2-(Chloromethyl)-6-(3-(difluoromethoxy)-4-fluorophenyl)pyrazine (Intermediate 8) in Step A. MS (ESI): mass calcd. for $C_{12}H_{10}F_3N_3O$, 269.1; m/z found, 270 $[M+H]^+$.

Intermediate 18: (6-(4-Chloro-3-(difluoromethoxy)phenyl)pyrazin-2-yl)methanamine

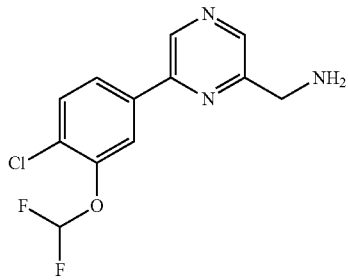 [SMILES: NCc1cncc(-c2ccc(Cl)c(OC(F)F)c2)n1]

Prepared analogous to (6-(3-(1,1-Difluoroethyl)phenyl)pyrazin-2-yl)methanamine (Intermediate 16), using 2-(4-Chloro-3-(difluoromethoxy)phenyl)-6-(chloromethyl)pyrazine (Intermediate 9) in Step A. MS (ESI): mass calcd. for $C_{12}H_{10}ClF_2N_3O$, 285.1; m/z found, 286 $[M+H]^+$.

Intermediate 19: (6-(4-Chloro-3-(difluoromethoxy)phenyl)-3-methylpyrazin-2-yl)methanamine

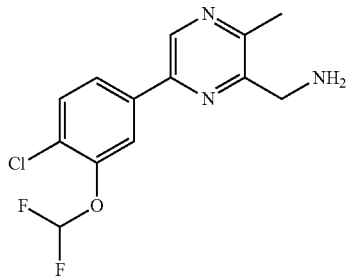 [SMILES: Cc1ncc(-c2ccc(Cl)c(OC(F)F)c2)nc1CN]

Prepared analogous to (6-(3-(1,1-Difluoroethyl)phenyl)pyrazin-2-yl)methanamine (Intermediate 16), using 5-(4-Chloro-3-(difluoromethoxy)phenyl)-3-(chloromethyl)-2-methylpyrazine (Intermediate 15) in Step A.

Intermediate 20: (6-(3-(Difluoromethyl)-4-fluorophenyl)pyrazin-2-yl)methanamine

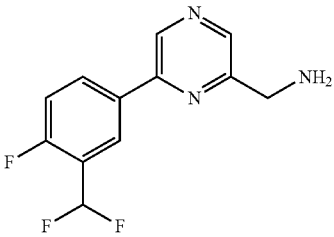 [SMILES: NCc1cncc(-c2ccc(F)c(C(F)F)c2)n1]

Prepared analogous to (6-(3-(1,1-Difluoroethyl)phenyl)pyrazin-2-yl)methanamine (Intermediate 16), using 2-(Chloromethyl)-6-(3-(difluoromethyl)-4-fluorophenyl)pyrazine (Intermediate 7) in Step A. MS (ESI): mass calcd. for $C_{12}H_{10}F_3N_3$, 253.1; m/z found, 254 $[M+H]^+$.

Intermediate 21: (6-(3-(Difluoromethyl)-4-fluorophenyl)-3-methylpyrazin-2-yl)methanamine

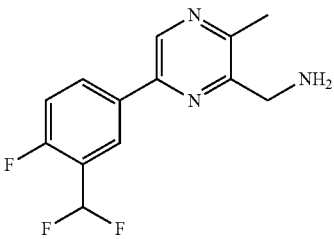 [SMILES: Cc1ncc(-c2ccc(F)c(C(F)F)c2)nc1CN]

Prepared analogous to (6-(3-(1,1-Difluoroethyl)phenyl)pyrazin-2-yl)methanamine (Intermediate 16), using 3-(Chloromethyl)-5-(3-(difluoromethyl)-4-fluorophenyl)-2-methylpyrazine (Intermediate 14) in Step A. MS (ESI): mass calcd. for $C_{13}H_{12}F_3N_3$, 267.1; m/z found, 268 $[M+H]^+$.

Intermediate 22: (6-(3-(Difluoromethoxy)-4-fluorophenyl)-3-methylpyrazin-2-yl)methanamine

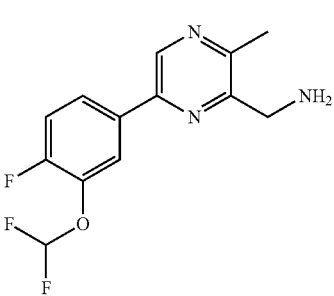 [SMILES: Cc1ncc(-c2ccc(F)c(OC(F)F)c2)nc1CN]

Prepared analogous to (6-(3-(1,1-Difluoroethyl)phenyl)pyrazin-2-yl)methanamine (Intermediate 16), using 3-(Chloromethyl)-5-(3-(difluoromethoxy)-4-fluorophenyl)-2-methylpyrazine (Intermediate 13) in Step A. MS (ESI): mass calcd. for $C_{13}H_{12}F_3N_3O$, 283.1; m/z found, 284 $[M+H]^+$.

Intermediate 23: 2-(3-(Difluoromethyl)-4-fluorophenyl)-4,4,5,5-tetramethyl-1,3,2-dioxaborolane

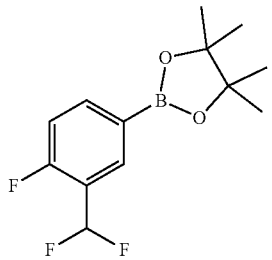 [SMILES: CC1(C)OB(c2ccc(F)c(C(F)F)c2)OC1(C)C]

A solution of 4-bromo-2-(difluoromethyl)-1-fluorobenzene (20 g, 88.9 mmol), bis(pinacolato)diboron (24.8 g, 97.8 mmol), potassium acetate (26.2 g, 267 mmol), and [1,1-bis(diphenylphosphino)ferrocene]-dichloropalladium(II) (3.12 g, 4.44 mmol) in 1,4-dioxane (400 mL) was purged with $N_2$, and the reaction mixture was stirred at 90° C. overnight. Upon completion, the reaction mixture was cooled to room temperature, filtered through Celite®, and rinsed with EtOAc. The filtrate was washed with water and brine. The combined organics were dried with $Na_2SO_4$, filtered and concentrated to yield a clear oil (22.1 g, 81.0 mmol, 91%), which solidified upon standing. $^1$H NMR (400 MHz, Chloroform-d) δ 8.12-8.00 (m, 1H), 7.96-7.85 (m, 1H), 7.17-7.06 (m, 1H), 6.88 (t, J=54.9 Hz, 1H), 1.35 (s, 12H). MS (ESI): mass calcd. for $C_{13}H_{16}BF_3O_2$, 272.1; m/z found, 273.0 [M+H]$^+$.

Intermediate 24: 2-(3-(1,1-Difluoroethyl)-4-fluorophenyl)-4,4,5,5-tetramethyl-1,3,2-dioxaborolane

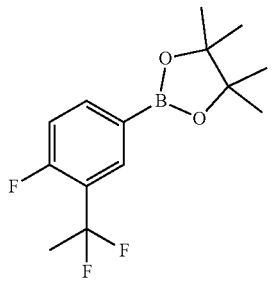 [SMILES: CC(F)(F)c1cc(B2OC(C)(C)C(C)(C)O2)ccc1F]

Step A: 4-Bromo-2-(1,1-difluoroethyl)-1-fluorobenzene. In a round bottom flask, a mixture of 1-(5-bromo-2-fluorophenyl)-1-ethanone (2.5 g, 11.5 mmol, 1 equiv) and DAST (1.9 mL, 14.4 mmol, 1.25 equiv) was heated at 60° C. for 16 h. Then a sat. aq. solution of $NaHCO_3$ was slowly added at 0° C. and extracted with DCM. The organic layers were combined, dried over $MgSO_4$, filtered, and partially concentrated (product is volatile). The crude product was purified by flash column chromatography (silica; 100% DCM) to give the title compound (3 g, 7.5 mmol, purity 60%, 65%) as a brown oil. $^1$H NMR (300 MHz, CDCl$_3$) δ 7.73-7.61 (m, 1H), 7.60-7.48 (m, 1H), 7.02 (t, J=9.4 Hz, 1H), 1.98 (t, J=18.6 Hz, 3H).

Step B: 2-(3-(1,1-Difluoroethyl)-4-fluorophenyl)-4,4,5,5-tetramethyl-1,3,2-dioxaborolane. In a round bottom flask, bis(pinacolato)diboron (2.87 g, 11.3 mmol, 1.5 equiv), potassium acetate (2.22 g, 22.6 mmol, 3 equiv), and [1,1'-bis(diphenylphosphino)ferrocene]-dichloropalladium(II) (615 mg, 0.75 mmol, 0.1 equiv) were added to a solution of 4-bromo-2-(1,1-difluoroethyl)-1-fluorobenzene (3 g, 7.5 mmol, 1 equiv) in dry 1,4-dioxane (40 mL). The mixture was purged with nitrogen and stirred at 90° C. for 16 h. Then, a sat. aq. solution of $NaHCO_3$ was added and the mixture was extracted with EtOAc. The combined organics were dried with $MgSO_4$, filtered and concentrated to yield a brown oil (2.15 g, 7.53 mmol), which was used in the next step without further purification. MS (ESI): mass calcd. for $C_{14}H_{18}BF_3O_2$, 286.1; m/z found, 287.1 [M+H]$^+$.

Intermediate 25: 2-(3-(1,1-Difluoroethyl)phenyl)-4,4,5,5-tetramethyl-1,3,2-dioxaborolane

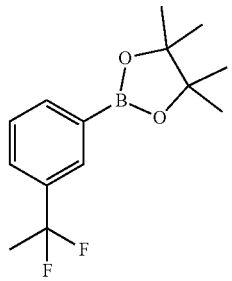 [SMILES: CC(F)(F)c1cccc(B2OC(C)(C)C(C)(C)O2)c1]

The title compound was prepared in a manner analogous to 2-(3-(Difluoromethyl)-4-fluorophenyl)-4,4,5,5-tetramethyl-1,3,2-dioxaborolane (Intermediate 23) using 1-bromo-3-(1,1-difluoroethyl)benzene instead of 4-bromo-2-(difluoromethyl)-1-fluorobenzene.

Intermediate 26: 2-(3-(Difluoromethoxy)-4-fluorophenyl)-4,4,5,5-tetramethyl-1,3,2-dioxaborolane

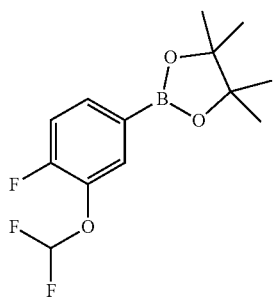 [SMILES: CC1(C)OB(c2ccc(F)c(OC(F)F)c2)OC1(C)C]

The title compound was prepared in a manner analogous to 2-(3-(Difluoromethyl)-4-fluorophenyl)-4,4,5,5-tetramethyl-1,3,2-dioxaborolane (Intermediate 23) using 4-bromo-2-(difluoromethoxy)-1-fluorobenzene instead of 4-bromo-2-(difluoromethyl)-1-fluorobenzene. MS (ESI): mass calcd. for $C_{13}H_{16}BF_3O_3$, 288.1; m/z found, 289.0 [M+H]$^+$.

Intermediate 27: 2-(4-Chloro-3-(difluoromethoxy)phenyl)-4,4,5,5-tetramethyl-1,3,2-dioxaborolane

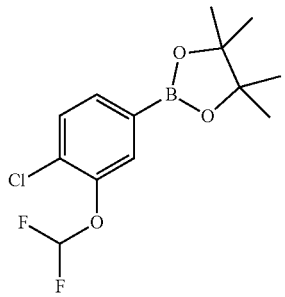 [SMILES: CC1(C)OB(c2ccc(Cl)c(OC(F)F)c2)OC1(C)C]

The title compound was prepared in a manner analogous to 2-(3-(Difluoromethyl)-4-fluorophenyl)-4,4,5,5-tetramethyl-1,3,2-dioxaborolane (Intermediate 23) using 4-bromo-1-chloro-2-(difluoromethoxy)benzene instead of 4-bromo-2-(difluoromethyl)-1-fluorobenzene. $^1$H NMR (500 MHz, CDCl$_3$) δ 7.62-7.56 (m, 2H), 7.44 (d, J=7.9 Hz, 1H), 6.56 (t, J=73.6 Hz, 1H), 1.34 (s, 12H).

5.2. Compounds of Formula (I): Examples 1-68

Example 1: 3-[[6-[3-(Difluoromethyl)-4-fluoro-phenyl]pyrazin-2-yl]methyl]oxazolidin-2-one

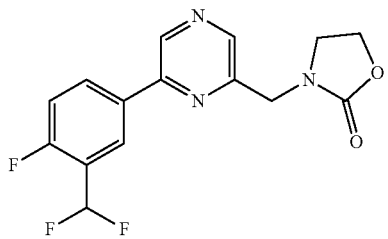 [SMILES: O=C1OCCN1Cc1cncc(-c2ccc(F)c(C(F)F)c2)n1]

Step A: 2-Chloro-6-(chloromethyl)pyrazine. To a solution of (6-chloropyrazin-2-yl)methanol (1 g, 6.9 mmol, 1 equiv) in DCM (12 mL) at 0° C. was added thionyl chloride (1 mL, 13.8 mmol, 2 equiv), and the reaction mixture was warmed to room temperature and stirred over the weekend. Upon addition of thionyl chloride the reaction becomes heterogeneous. Analysis by LCMS did not show complete conversion and additional thionyl chloride (0.5 equiv) was added and the reaction was stirred at room temperature for 1 h. The mixture was poured into a cold saturated aqueous solution of Na$_2$CO$_3$. Then, the crude reaction mixture was extracted with DCM (3×). the combined organics were dried over Na$_2$SO$_4$, filtered and concentrated to give the title compound (1 g, 6.2 mmol, 90%) as a light brown residue. The material was used without further purification.

Step B: 3-((6-Chloropyrazin-2-yl)methyl)oxazolidin-2-one. To a solution of 2-oxazolidone (80 mg, 0.92 mmol, 1.5 equiv) and 2-chloro-6-(chloromethyl)pyrazine (100 mg, 0.61 mmol, 1 equiv) in DMF (3 mL) was added NaH (39 mg, 0.98 mmol, 60% dispersion in mineral oil, 1.6 equiv), and the reaction mixture was stirred at room temperature for 1.5 h. Then, the reaction mixture was diluted with H$_2$O and extracted with EtOAc (3×). The organic layers were combined, dried (Na$_2$SO$_4$), concentrated, and subjected directly to purification. Purification via silica gel chromatography (0-70% EtOAc (with 10% MeOH) in hexanes) gave the title compound (36 mg, 0.17 mmol, 27%). MS (ESI) mass calcd. for C$_8$H$_8$ClN$_3$O$_2$, 213.0; m/z found 214.1 [M+H]$^+$.

Step C: 3-[[6-[3-(Difluoromethyl)-4-fluoro-phenyl]pyrazin-2-yl]methyl]oxazolidin-2-one. A mixture of 3-((6-chloropyrazin-2-yl)methyl)oxazolidin-2-one (17.5 mg, 0.082 mmol, 1 equiv), 2-[3-(difluoromethyl)-4-fluoro-phenyl]-4,4,5,5-tetramethyl-1,3,2-dioxaborolane (29 mg, 0.11 mmol, 1.3 equiv), [1,1'-bis(diphenylphosphino)ferrocene]dichloropalladium(II) (3 mg, 0.004 mmol, 0.05 equiv) and potassium carbonate (28 mg, 0.21 mmol, 2.5 equiv) in 1,4-dioxane (0.7 mL) and water (0.17 mL) was stirred at 90° C. for 2 h. The reaction mixture was cooled to room temperature, filtered through Celite® and concentrated. The crude product was purified by preparative HPLC (Method A) to yield the title compound (18 mg, 0.056 mmol, 68%). MS (ESI): mass calcd. for C$_{15}$H$_{12}$F$_3$N$_3$O$_2$, 323.1; m/z found, 324.1 [M+H]$^+$. $^1$H NMR (400 MHz, Methanol-d$_4$) δ 9.10 (s, 1H), 8.59 (s, 1H), 8.46-8.36 (m, 1H), 8.35-8.26 (m, 1H), 7.52-7.31 (m, 1H), 7.07 (t, J=54.6 Hz, 1H), 4.70 (s, 2H), 4.51-4.30 (m, 2H), 3.91-3.70 (m, 2H).

Example 2: 3-[[6-[3-(Difluoromethoxy)-4-fluoro-phenyl]pyrazin-2-yl]methyl]oxazolidin-2-one

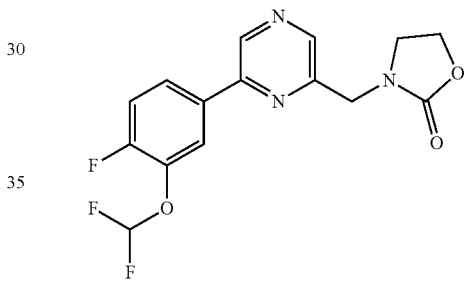

Prepared analogous to Example 1, using 2-(3-(difluoromethoxy)-4-fluorophenyl)-4,4,5,5-tetramethyl-1,3,2-dioxaborolane (Intermediate 26) in Step C. MS (ESI): mass calcd. for C$_{15}$H$_{12}$F$_3$N$_3$O$_3$, 339.1; m/z found, 340.0 [M+H]$^+$. $^1$H NMR (400 MHz, Methanol-d$_4$) δ 9.07 (s, 1H), 8.58 (s, 1H), 8.10 (dd, J=7.6, 2.2 Hz, 1H), 8.08-7.97 (m, 1H), 7.42 (dd, J=10.2, 8.7 Hz, 1H), 6.96 (t, J=73.2 Hz, 1H), 4.69 (s, 2H), 4.50-4.31 (m, 2H), 3.86-3.61 (m, 2H).

Example 3: 5-[[6-[3-(Difluoromethyl)-4-fluoro-phenyl]pyrazin-2-yl]methyl]-7-oxa-5-azaspiro[2.4]heptan-6-one

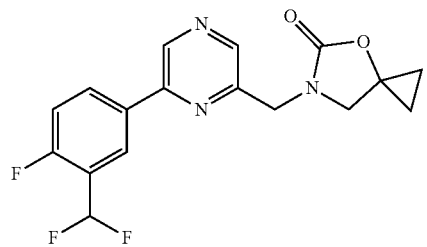 [SMILES: O=C1OC2(CC2)CN1Cc1cncc(-c2ccc(F)c(C(F)F)c2)n1]

Sodium hydride (12 mg, 0.3 mmol, 60% dispersion in mineral oil, 1.1 equiv) was added to a solution of 2-(Chloromethyl)-6-(3-(difluoromethyl)-4-fluorophenyl)pyrazine (Intermediate 7) (35.8 mg, 0.3 mmol, 1.1 equiv) in dry DMF (3 mL) at 0° C., and the mixture was stirred for 30 minutes, Then, a solution of 4-Oxa-6-azaspiro[2.4]heptan-5-one (Intermediate 1) (75 mg, 0.27 mmol, 1 equiv) in DMF (0.5 mL) was added dropwise to the reaction mixture at 0° C., and the reaction mixture was stirred at room temperature for 2 h. A saturated aqueous solution of NaHCO$_3$ was added dropwise and the reaction mixture was diluted with AcOEt. The organic layer was separated, and the aqueous layer was further extracted with AcOEt. The combined organics were dried over MgSO$_4$, filtered and the solvents removed under vacuum to afford a white solid. This crude was purified by flash column chromatography (silica, AcOEt in Heptane from 0/100 to 30/70) to give the title compound (43 mg, 0.12 mmol, 44%). MS (ESI): mass calcd. for $C_{17}H_{14}F_3N_3O_2$, 349.1; m/z found, 350 [M+H]$^+$. $^1$H NMR (300 MHz, CDCl$_3$) δ 8.99 (s, 1H), 8.62 (s, 1H), 8.31 (d, J=5.1 Hz, 1H), 8.16 (s, 1H), 7.35-7.28 (m, 1H), 6.97 (t, J=54.8 Hz, 1H), 4.73 (s, 2H), 3.77 (s, 2H), 1.27 (s, 2H), 0.73 (s, 2H).

Example 4: 3-[[6-[3-(Difluoromethyl)-4-fluoro-phenyl]pyrazin-2-yl]methyl]-5,5-dimethyl-oxazolidin-2-one

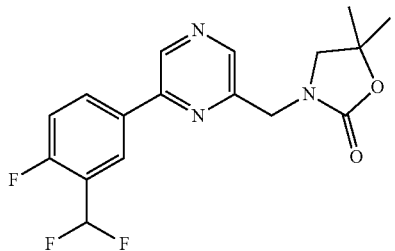 [SMILES: CC1(C)CN(Cc2cncc(-c3ccc(F)c(C(F)F)c3)n2)C(=O)O1]

Prepared analogous to Example 3, using 5,5-dimethyl-oxazolidin-2-one. MS (ESI): mass calcd. for $C_{17}H_{16}F_3N_3O_2$, 351.1; m/z found, 352 [M+H]$^+$. $^1$H NMR (300 MHz, CDCl$_3$) δ 9.00 (s, 1H), 8.59 (s, 1H), 8.32 (d, J=4.9 Hz, 1H), 8.17 (s, 1H), 7.29 (d, J=11.9 Hz, 1H), 6.95 (dd, J=64.1, 45.4 Hz, 1H), 4.72 (s, 2H), 3.47 (s, 2H), 2.22 (s, 6H).

Example 5: (5R)-3-[[6-[3-(Difluoromethyl)-4-fluoro-phenyl]pyrazin-2-yl]methyl]-5-methyl-oxazolidin-2-one

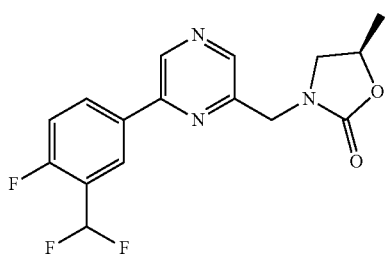 [SMILES: C[C@@H]1CN(Cc2cncc(-c3ccc(F)c(C(F)F)c3)n2)C(=O)O1]

Prepared analogous to Example 3, using (R)-5-Methyl-oxazolidin-2-one (Intermediate 2). MS (ESI): mass calcd. for $C_{16}H_{14}F_3N_3O_2$, 337.1; m/z found, 338 [M+H]$^+$. $^1$H NMR (300 MHz, CDCl$_3$) δ 8.88 (s, 1H), 8.49 (s, 1H), 8.20 (d, J=6.4 Hz, 1H), 8.07 (s, 1H), 7.22 (d, J=9.1 Hz, 1H), 6.88 (t, J=54.8 Hz, 1H), 4.63 (dd, J=13.9, 7.0 Hz, 1H), 4.58 (s, 2H), 3.69 (t, J=8.3 Hz, 1H), 3.21 (t, J=7.6 Hz, 1H), 1.37 (d, J=6.0 Hz, 3H).

Example 6: (5S)-3-[[6-[3-(Difluoromethyl)-4-fluoro-phenyl]pyrazin-2-yl]methyl]-5-methyl-oxazolidin-2-one

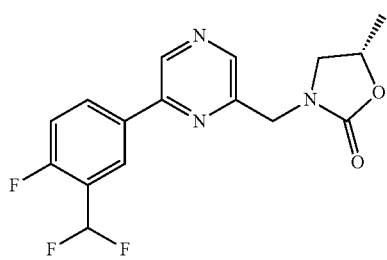 [SMILES: C[C@H]1CN(Cc2cncc(-c3ccc(F)c(C(F)F)c3)n2)C(=O)O1]

Prepared analogous to Example 3, using (S)-5-Methyl-oxazolidin-2-one (Intermediate 3). MS (ESI): mass calcd. for $C_{16}H_{14}F_3N_3O_2$, 337.1; m/z found, 338 [M+H]$^+$. $^1$H NMR (300 MHz, CDCl$_3$) δ 8.97 (s, 1H), 8.58 (s, 1H), 8.29 (d, J=6.2 Hz, 1H), 8.16 (s, 1H), 7.38-7.27 (t, 1H), 6.97 (t, J=54.8 Hz, 1H), 4.72 (m, J=13.8, 7.0 Hz, 1H), 4.67 (s, 2H), 3.78 (t, J=8.2 Hz, 1H), 3.30 (t, J=7.6 Hz, 1H), 1.46 (d, J=6.1 Hz, 3H).

Example 7: (4R)-3-[[6-[3-(Difluoromethyl)-4-fluoro-phenyl]pyrazin-2-yl]methyl]-4-methyl-oxazolidin-2-one

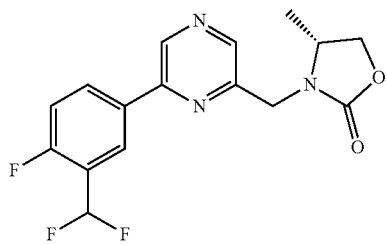 [SMILES: C[C@@H]1COC(=O)N1Cc1cncc(-c2ccc(F)c(C(F)F)c2)n1]

Prepared analogous to Example 3, using (R)-4-methyl-oxazolidin-2-one. MS (ESI): mass calcd. for $C_{16}H_{14}F_3N_3O_2$, 337.1; m/z found, 338 [M+H]$^+$. $^1$H NMR (300 MHz, CDCl$_3$) δ 8.97 (s, 1H), 8.62 (s, 1H), 8.28 (d, J=5.2 Hz, 1H), 8.15 (bs, 1H), 7.31 (d, J=9.1 Hz, 1H), 6.97 (t, J=54.8 Hz, 1H), 4.84 (d, J=16.1 Hz, 1H), 4.57-4.40 (m, 2H), 4.07-3.85 (m, 2H), 1.34 (d, J=5.5 Hz, 3H).

Example 8: (4S)-3-[[6-[3-(Difluoromethyl)-4-fluoro-phenyl]pyrazin-2-yl]methyl]-4-methyl-oxazolidin-2-one

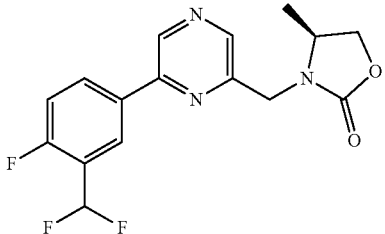

Prepared analogous to Example 3, using (S)-4-methyl-oxazolidin-2-one. MS (ESI): mass calcd. for $C_{16}H_{14}F_3N_3O_2$, 337.1; m/z found, 338 [M+H]$^+$. $^1$H NMR (300 MHz, CDCl$_3$) δ 8.97 (s, 1H), 8.62 (s, 1H), 8.28 (d, J=5.3 Hz, 1H), 8.21-8.09 (m, 1H), 7.35-7.22 (m, 1H), 6.97 (t, J=54.8 Hz, 1H), 4.84 (d, J=16.1 Hz, 1H), 4.59-4.38 (m, 2H), 4.07-3.88 (m, 2H), 1.34 (d, J=5.6 Hz, 3H).

Example 9: 3-[[6-[3-(Difluoromethyl)-4-fluoro-phenyl]pyrazin-2-yl]methyl]-1,3-oxazinan-2-one

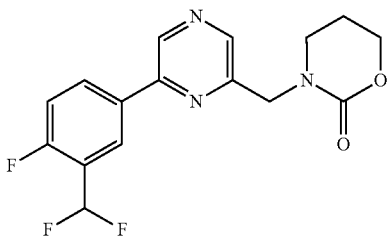 [SMILES: O=C1OCCCN1Cc1cncc(-c2ccc(F)c(C(F)F)c2)n1]

Prepared analogous to Example 3, using 1,3-oxazinan-2-one. MS (ESI): mass calcd. for $C_{16}H_{14}F_3N_3O_2$, 337.1; m/z found, 338 [M+H]$^+$. $^1$H NMR (300 MHz, CDCl$_3$) δ 8.95 (s, 1H), 8.62 (s, 1H), 8.30 (d, J=6.3 Hz, 1H), 8.14 (s, 1H), 7.29 (t, J=6.7 Hz, 1H), 6.95 (dd, J=63.9, 45.9 Hz, 1H), 4.74 (s, 2H), 4.41-4.29 (m, 2H), 3.56 (t, J=6.0 Hz, 2H), 2.20-2.05 (m, 2H).

Example 10: 5-[[6-[3-(Difluoromethyl)-4-fluorophenyl]-3-methyl-pyrazin-2-yl]methyl]-7-oxa-5-azaspiro[2.4]heptan-6-one

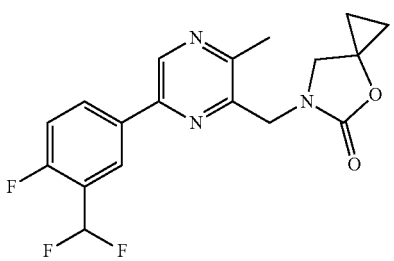 [SMILES: Cc1ncc(-c2ccc(F)c(C(F)F)c2)nc1CN1CC2(CC2)OC1=O]

Prepared analogous to Example 3, using 3-(Chloromethyl)-5-(3-(difluoromethyl)-4-fluorophenyl)-2-methylpyrazine (Intermediate 14). MS (ESI): mass calcd. for $C_{18}H_{16}F_3N_3O_2$, 363.1; m/z found, 364 [M+H]$^+$. $^1$H NMR (300 MHz, CDCl$_3$) δ 8.85 (s, 1H), 8.29 (d, J=6.4 Hz, 1H), 8.13 (dd, J=7.4, 4.0 Hz, 1H), 7.31-7.22 (m, 1H+CDCl$_3$), 6.96 (t, J=54.9 Hz, 1H), 4.71 (s, 2H), 3.78 (s, 2H), 2.66 (s, 3H), 1.28 (t, J=6.9 Hz, 2H), 0.78-0.68 (m, 2H).

Example 11: (4R)-3-[[6-[3-(Difluoromethyl)-4-fluoro-phenyl]-3-methyl-pyrazin-2-yl]methyl]-4-methyl-oxazolidin-2-one

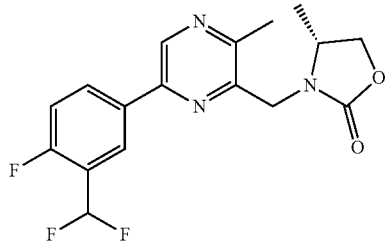 [SMILES: Cc1ncc(-c2ccc(F)c(C(F)F)c2)nc1CN1C(=O)OC[C@H]1C]

Prepared analogous to Example 3, using (R)-4-methyl-oxazolidin-2-one and 3-(Chloromethyl)-5-(3-(difluoromethyl)-4-fluorophenyl)-2-methylpyrazine (Intermediate 14). MS (ESI): mass calcd. for $C_{17}H_{16}F_3N_3O_2$, 351.1; m/z found, 352 [M+H]$^+$. $^1$H NMR (300 MHz, CDCl$_3$) δ 8.84 (s, 1H), 8.25 (d, J=5.9 Hz, 1H), 8.09 (d, J=5.2 Hz, 1H), 7.31-7.21 (m, 1H+CDCl$_3$), 6.96 (t, J=54.9 Hz, 1H), 4.93 (d, J=16.5 Hz, 1H), 4.52 (t, J=8.2 Hz, 1H), 4.38 (d, J=16.5 Hz, 1H), 4.07 (m, J=13.9, 7.3 Hz, 1H), 4.00-3.88 (t, 1H), 2.66 (s, 3H), 1.33 (d, J=6.1 Hz, 3H).

Example 12: (4S)-3-[[6-[3-(Difluoromethyl)-4-fluoro-phenyl]-3-methyl-pyrazin-2-yl]methyl]-4-methyl-oxazolidin-2-one

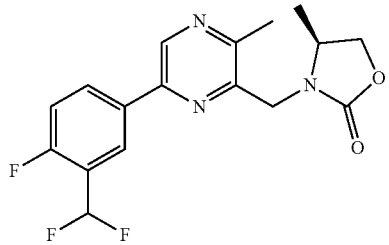 [SMILES: Cc1ncc(-c2ccc(F)c(C(F)F)c2)nc1CN1C(=O)OC[C@@H]1C]

Prepared analogous to Example 3, using (S)-4-methyl-oxazolidin-2-one and 3-(Chloromethyl)-5-(3-(difluoromethyl)-4-fluorophenyl)-2-methylpyrazine (Intermediate 14). MS (ESI): mass calcd. for $C_{17}H_{16}F_3N_3O_2$, 351.1; m/z found, 352 [M+H]$^+$. $^1$H NMR (300 MHz, CDCl$_3$) δ 8.84 (s, 1H), 8.25 (d, J=5.7 Hz, 1H), 8.15-8.05 (m, 1H), 7.28 (d, J=11.1 Hz, 1H+CDCl$_3$), 6.96 (t, J=54.9 Hz, 1H), 4.93 (d, J=16.5 Hz, 1H), 4.52 (t, J=8.2 Hz, 1H), 4.38 (d, J=16.5 Hz, 1H), 4.07 (m, J=13.9, 7.4 Hz, 1H), 3.99-3.88 (t, 1H), 2.66 (s, 3H), 1.33 (d, J=6.1 Hz, 3H).

Example 13: (5R)-3-[[6-[3-(Difluoromethyl)-4-fluoro-phenyl]-3-methyl-pyrazin-2-yl]methyl]-5-methyl-oxazolidin-2-one

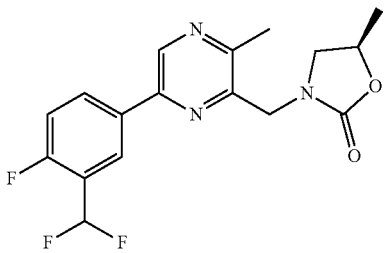 [SMILES: Cc1ncc(-c2ccc(F)c(C(F)F)c2)nc1CN1C[C@@H](C)OC1=O]

Prepared analogous to Example 3, using (R)-5-Methyl-oxazolidin-2-one (Intermediate 2) and 3-(Chloromethyl)-5-(3-(difluoromethyl)-4-fluorophenyl)-2-methylpyrazine (Intermediate 14). MS (ESI): mass calcd. for $C_{17}H_{16}F_3N_3O_2$, 351.1; m/z found, 352 [M+H]$^+$. $^1$H NMR (300 MHz, CDCl$_3$) δ 8.84 (s, 1H), 8.26 (d, J=5.8 Hz, 1H), 8.15-8.03 (m, 1H), 7.32-7.23 (m, 1H+CDCl$_3$), 6.96 (t, J=54.9 Hz, 1H), 4.65 (d, J=2.4 Hz, 2H), 3.77 (t, J=8.2 Hz, 1H), 3.49 (d, J=5.3 Hz, 1H), 3.35 (dd, J=8.0, 7.3 Hz, 1H), 2.64 (s, 3H), 1.48 (d, J=6.2 Hz, 3H).

Example 14: (5S)-3-[[6-[3-(Difluoromethyl)-4-fluoro-phenyl]-3-methyl-pyrazin-2-yl]methyl]-5-methyl-oxazolidin-2-one

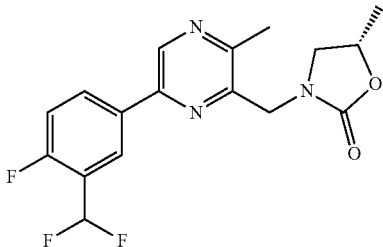 [SMILES: Cc1ncc(-c2ccc(F)c(C(F)F)c2)nc1CN1C[C@H](C)OC1=O]

Prepared analogous to Example 3, using (S)-5-Methyl-oxazolidin-2-one (Intermediate 3) and 3-(Chloromethyl)-5-(3-(difluoromethyl)-4-fluorophenyl)-2-methylpyrazine (Intermediate 14). MS (ESI): mass calcd. for $C_{17}H_{16}F_3N_3O_2$, 351.1; m/z found, 352 [M+H]$^+$. $^1$H NMR (300 MHz, CDCl$_3$) δ 8.84 (s, 1H), 8.26 (d, J=5.8 Hz, 1H), 8.14-8.06 (m, 1H), 7.34-7.20 (m, 1H), 6.96 (t, J=54.9 Hz, 1H), 4.83-4.67 (m, 1H), 4.65 (d, J=2.3 Hz, 2H), 3.77 (t, J=8.2 Hz, 1H), 3.35 (dd, J=8.1, 7.2 Hz, 1H), 2.64 (s, 3H), 1.48 (d, J=6.2 Hz, 3H).

Example 15: 3-[[6-[3-(Difluoromethyl)-4-fluoro-phenyl]-3-methyl-pyrazin-2-yl]methyl]-1,3-oxazinan-2-one

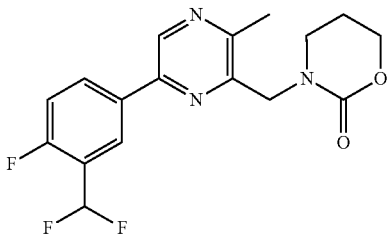 [SMILES: Cc1ncc(-c2ccc(F)c(C(F)F)c2)nc1CN1CCCOC1=O]

Prepared analogous to Example 3, using 1,3-oxazinan-2-one and 3-(Chloromethyl)-5-(3-(difluoromethyl)-4-fluoro-phenyl)-2-methylpyrazine (Intermediate 14). MS (ESI): mass calcd. for $C_{17}H_{16}F_3N_3O_2$, 351.1; m/z found, 352 [M+H]$^+$. $^1$H NMR (300 MHz, CDCl$_3$) δ 8.81 (s, 1H), 8.28 (d, J=5.9 Hz, 1H), 8.15-7.91 (m, 1H), 7.34-7.20 (m, 1H), 6.97 (t, J=54.9 Hz, 1H), 4.73 (s, 2H), 4.46-4.30 (m, 2H), 3.53 (t, J=6.2 Hz, 2H), 2.62 (s, 3H), 2.25-2.06 (m, 2H).

Example 16: 5-[[6-[3-(Difluoromethoxy)-4-fluoro-phenyl]pyrazin-2-yl]methyl]-7-oxa-5-azaspiro[2.4]heptan-6-one

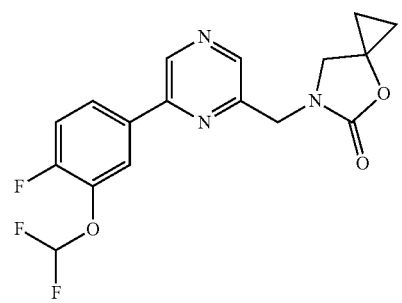 [SMILES: O=C1OC2(CC2)CN1Cc1cncc(-c2ccc(F)c(OC(F)F)c2)n1]

Prepared analogous to Example 3, using 2-(Chloromethyl)-6-(3-(difluoromethoxy)-4-fluorophenyl)pyrazine (Intermediate 8). MS (ESI): mass calcd. for $C_{17}H_{14}F_3N_3O_3$, 365.1; m/z found, 366 [M+H]$^+$. $^1$H NMR (300 MHz, CDCl$_3$) δ 8.97 (s, 1H), 8.63 (s, 1H), 8.01 (d, J=7.3 Hz, 1H), 7.95-7.82 (m, 1H), 7.34 (t, J=9.2 Hz, 1H), 6.67 (t, J=73.1 Hz, 1H), 4.74 (s, 2H), 3.79 (s, 2H), 1.29 (t, J=6.8 Hz, 2H), 0.75 (t, J=6.8 Hz, 2H).

Example 17: 3-[[6-[3-(Difluoromethoxy)-4-fluoro-phenyl]pyrazin-2-yl]methyl]-5,5-dimethyl-oxazolidin-2-one

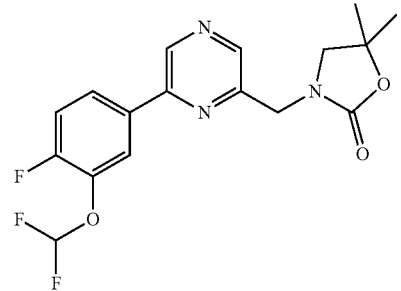 [SMILES: CC1(C)CN(Cc2cncc(-c3ccc(F)c(OC(F)F)c3)n2)C(=O)O1]

Prepared analogous to Example 3, using 5,5-dimethyl-oxazolidin-2-one and 2-(Chloromethyl)-6-(3-(difluoromethoxy)-4-fluorophenyl)pyrazine (Intermediate 8). MS (ESI): mass calcd. for $C_{17}H_{16}F_3N_3O_3$, 367.1; m/z found, 368 [M+H]$^+$. $^1$H NMR (300 MHz, CDCl$_3$) δ 8.93 (s, 1H), 8.56 (s, 1H), 7.97 (d, J=7.3 Hz, 1H), 7.87 (dd, J=5.3, 3.2 Hz, 1H), 7.31 (t, J=9.2 Hz, 1H), 6.64 (t, J=73.1 Hz, 1H), 4.66 (s, 2H), 3.44 (s, 2H), 1.48 (s, 6H).

Example 18: (4R)-3-[[6-[3-(Difluoromethoxy)-4-fluoro-phenyl]pyrazin-2-yl]methyl]-4-methyl-oxazolidin-2-one

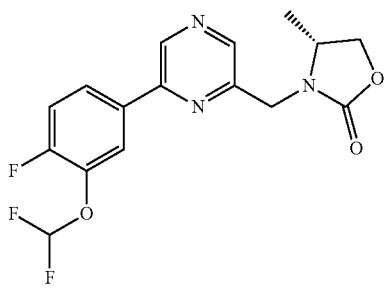 [SMILES: C[C@@H]1COC(=O)N1Cc1cncc(-c2ccc(F)c(OC(F)F)c2)n1]

Prepared analogous to Example 3, using (R)-4-methyl-oxazolidin-2-one and 2-(Chloromethyl)-6-(3-(difluoromethoxy)-4-fluorophenyl)pyrazine (Intermediate 8). MS (ESI): mass calcd. for $C_{16}H_{14}F_3N_3O_3$, 353.1; m/z found, 354 [M+H]$^+$. $^1$H NMR (300 MHz, CDCl$_3$) δ 8.93 (s, 1H), 8.60 (s, 1H), 7.97 (d, J=7.0 Hz, 1H), 7.92-7.78 (m, 1H), 7.31 (t, J=9.1 Hz, 1H), 6.64 (t, J=73.1 Hz, 1H), 4.84 (d, J=16.1 Hz, 1H), 4.53-4.40 (m, 2H), 4.08-3.97 (m, 1H), 3.97-3.87 (m, 1H), 1.34 (d, J=5.7 Hz, 3H).

Example 19: (4S)-3-[[6-[3-(Difluoromethoxy)-4-fluoro-phenyl]pyrazin-2-yl]methyl]-4-methyl-oxazolidin-2-one

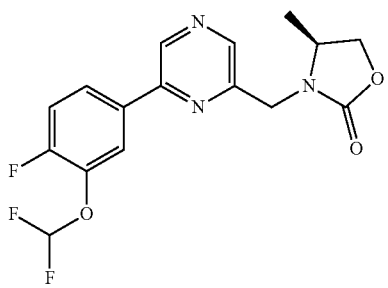 [SMILES: C[C@H]1COC(=O)N1Cc1cncc(-c2ccc(F)c(OC(F)F)c2)n1]

Prepared analogous to Example 3, using (S)-4-methyl-oxazolidin-2-one and 2-(Chloromethyl)-6-(3-(difluoromethoxy)-4-fluorophenyl)pyrazine (Intermediate 8). MS (ESI): mass calcd. for $C_{16}H_{14}F_3N_3O_3$, 353.1; m/z found, 354 [M+H]$^+$. $^1$H NMR (300 MHz, CDCl$_3$) δ 8.93 (s, 1H), 8.60 (s, 1H), 7.97 (d, J=6.9 Hz, 1H), 7.91-7.81 (m, 1H), 7.31 (t, J=9.2 Hz, 1H), 6.64 (t, J=73.1 Hz, 1H), 4.84 (d, J=16.1 Hz, 1H), 4.61-4.34 (m, 2H), 4.13-3.71 (m, 2H), 1.34 (d, J=5.6 Hz, 3H).

Example 20: (5R)-3-[[6-[3-(Difluoromethoxy)-4-fluoro-phenyl]pyrazin-2-yl]methyl]-5-methyl-oxazolidin-2-one

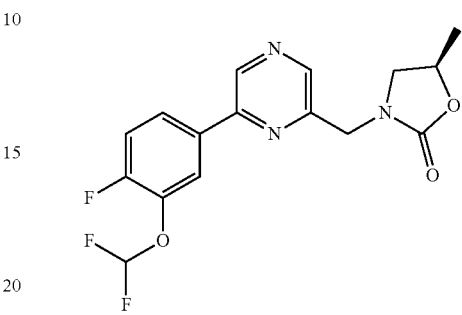

Prepared analogous to Example 3, using (R)-5-Methyl-oxazolidin-2-one (Intermediate 2) and 2-(Chloromethyl)-6-(3-(difluoromethoxy)-4-fluorophenyl)pyrazine (Intermediate 8). MS (ESI): mass calcd. for $C_{16}H_{14}F_3N_3O_3$, 353.1; m/z found, 354 [M+H]$^+$. $^1$H NMR (300 MHz, CDCl$_3$) δ 8.94 (s, 1H), 8.56 (s, 1H), 7.97 (d, J=6.9 Hz, 1H), 7.87 (bs, 1H), 7.30 (t, J=16.4, 7.4 Hz, 1H), 6.64 (t, J=73.1 Hz, 1H), 4.72 (m, J=13.2, 6.7 Hz, 1H), 4.66 (s, 2H), 3.79 (t, J=8.2 Hz, 1H), 3.29 (t, J=7.5 Hz, 1H), 1.46 (d, J=6.0 Hz, 3H).

Example 21: (5S)-3-[[6-[3-(Difluoromethoxy)-4-fluoro-phenyl]pyrazin-2-yl]methyl]-5-methyl-oxazolidin-2-one

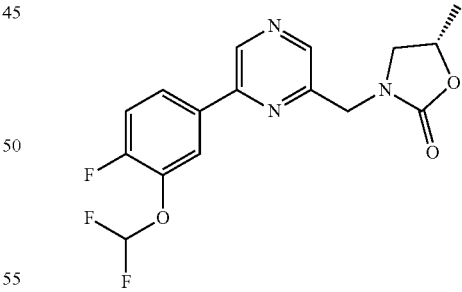

Prepared analogous to Example 3, using (S)-5-Methyl-oxazolidin-2-one (Intermediate 3) and 2-(Chloromethyl)-6-(3-(difluoromethoxy)-4-fluorophenyl)pyrazine (Intermediate 8). MS (ESI): mass calcd. for $C_{16}H_{14}F_3N_3O_3$, 353.1; m/z found, 354 [M+H]$^+$. $^1$H NMR (300 MHz, CDCl$_3$) δ 8.96 (s, 1H), 8.59 (s, 1H), 8.00 (d, J=7.2 Hz, 1H), 7.90 (d, J=2.0 Hz, 1H), 7.34 (t, J=9.4 Hz, 1H), 6.67 (t, J=73.2 Hz, 1H), 4.75 (dd, J=13.3, 6.7 Hz, 1H), 4.68 (s, 2H), 3.81 (t, J=8.2 Hz, 1H), 3.31 (t, J=7.5 Hz, 1H), 1.49 (d, J=6.1 Hz, 3H).

Example 22: 3-[[6-[3-(Difluoromethoxy)-4-fluoro-phenyl]pyrazin-2-yl]methyl]-1,3-oxazinan-2-one

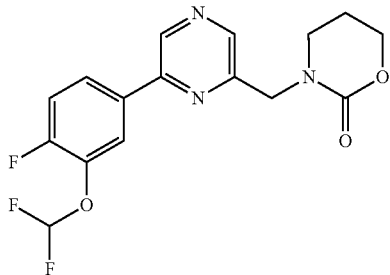 [SMILES: O=C1OCCCN1Cc1cncc(-c2ccc(F)c(OC(F)F)c2)n1]

Prepared analogous to Example 3, using 1,3-oxazinan-2-one and 2-(Chloromethyl)-6-(3-(difluoromethoxy)-4-fluorophenyl)pyrazine (Intermediate 8). MS (ESI): mass calcd. for $C_{16}H_{14}F_3N_3O_3$, 353.1; m/z found, 354 [M+H]$^+$. $^1$H NMR (300 MHz, CDCl$_3$) δ 8.91 (s, 1H), 8.60 (s, 1H), 7.98 (d, J=6.8 Hz, 1H), 7.85 (bs, 1H), 7.33 (t, J=9.3 Hz, 1H), 6.64 (t, J=73.1 Hz, 1H), 4.73 (s, 2H), 4.34 (t, 2H), 3.55 (t, J=5.6 Hz, 2H), 2.12 (m, 2H).

Example 23: 5-[[6-[3-(Difluoromethoxy)-4-fluoro-phenyl]-3-methyl-pyrazin-2-yl]methyl]-7-oxa-5-azaspiro[2.4]heptan-6-one

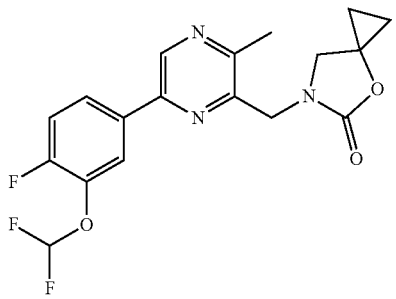 [SMILES: Cc1ncc(-c2ccc(F)c(OC(F)F)c2)nc1CN1CC2(CC2)OC1=O]

Prepared analogous to Example 3, using 3-(Chloromethyl)-5-(3-(difluoromethoxy)-4-fluorophenyl)-2-methylpyrazine (Intermediate 13). MS (ESI): mass calcd. for $C18H_{16}F_3N_3O_3$, 379.1; m/z found, [M+H]$^+$. $^1$H NMR (300 MHz, CDCl$_3$) δ 8.81 (s, 1H), 7.97 (d, J=7.3 Hz, 1H), 7.84 (ddd, J=8.4, 4.2, 2.1 Hz, 1H), 7.44-7.11 (m, 1H), 6.64 (t, J=73.3 Hz, 1H), 4.70 (s, 2H), 3.77 (s, 2H), 2.65 (s, 3H), 1.28 (t, J=7.0 Hz, 2H), 0.78-0.62 (m, 2H).

Example 24: (4R)-3-[[6-[3-(Difluoromethoxy)-4-fluoro-phenyl]-3-methyl-pyrazin-2-yl]methyl]-4-methyl-oxazolidin-2-one

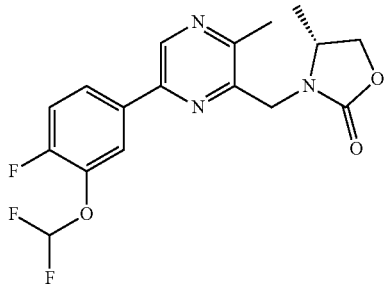 [SMILES: Cc1ncc(-c2ccc(F)c(OC(F)F)c2)nc1CN1C(=O)OC[C@H]1C]

Prepared analogous to Example 3, using (R)-4-methyl-oxazolidin-2-one and 3-(Chloromethyl)-5-(3-(difluoromethoxy)-4-fluorophenyl)-2-methylpyrazine (Intermediate 13). MS (ESI): mass calcd. for $C_{17}H_{16}F_3N_3O_3$, 367.1; m/z found, 368 [M+H]$^+$. $^1$H NMR (300 MHz, CDCl$_3$) δ 8.81 (s, 1H), 7.94 (d, J=7.5 Hz, 1H), 7.81 (ddd, J=8.6, 4.3, 2.2 Hz, 1H), 7.29 (t, J=7.1 Hz, 1H), 6.65 (t, J=73.1 Hz, 1H), 4.92 (d, J=16.6 Hz, 1H), 4.51 (t, J=8.2 Hz, 1H), 4.36 (d, J=16.6 Hz, 1H), 4.14-4.01 (m, 1H), 3.94 (t, 1H), 2.65 (s, 3H), 1.32 (d, J=6.1 Hz, 3H).

Example 25: (4S)-3-[[6-[3-(Difluoromethoxy)-4-fluoro-phenyl]-3-methyl-pyrazin-2-yl]methyl]-4-methyl-oxazolidin-2-one

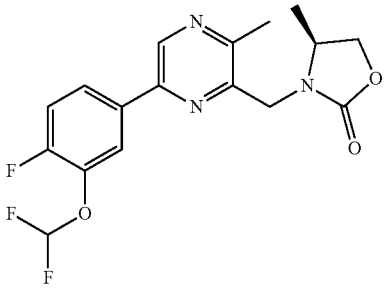 [SMILES: Cc1ncc(-c2ccc(F)c(OC(F)F)c2)nc1CN1C(=O)OC[C@@H]1C]

Prepared analogous to Example 3, using (S)-4-methyl-oxazolidin-2-one and 3-(Chloromethyl)-5-(3-(difluoromethoxy)-4-fluorophenyl)-2-methylpyrazine (Intermediate 13). MS (ESI): mass calcd. for $C_{17}H_{16}F_3N_3O_3$, 367.1; m/z found, 368 [M+H]$^+$. $^1$H NMR (300 MHz, CDCl$_3$) δ 8.73 (s, 1H), 7.88 (d, J=7.3 Hz, 1H), 7.79-7.67 (m, 1H), 7.22 (d, 1H), 6.57 (t, J=73.1 Hz, 1H), 4.85 (d, J=16.6 Hz, 1H), 4.44 (t, J=8.2 Hz, 1H), 4.29 (d, J=16.6 Hz, 1H), 4.08-3.94 (m, J=13.7, 6.7 Hz, 1H), 3.87 (t, J=7.9 Hz, 1H), 2.58 (s, 3H), 1.25 (d, J=6.1 Hz, 3H).

Example 26: (5R)-3-[[6-[3-(Difluoromethoxy)-4-fluoro-phenyl]-3-methyl-pyrazin-2-yl]methyl]-5-methyl-oxazolidin-2-one Prepared analogous to Example 3, using (R)-5-Methyl-oxazolidin-2-one (Intermediate 2) and 3-(Chloromethyl)-5-(3-(difluoromethoxy)-4-fluorophenyl)-2-methylpyrazine (Intermediate 13). MS (ESI): mass calcd. for $C_{17}H_{16}F_3N_3O_3$, 367.1; m/z found, 368 [M+H]$^+$. $^1$H NMR (300 MHz, CDCl$_3$) δ 8.83 (s, 1H), 7.94 (d, J=7.3 Hz, 1H), 7.89-7.77 (m, 1H), 7.30 (t, 1H), 6.65 (t, J=73.1 Hz, 1H), 4.82-4.69 (m, 1H), 4.66 (s, 2H), 3.80 (t, J=8.3 Hz, 1H), 3.33 (t, J=7.7 Hz, 1H), 2.65 (s, 3H), 1.48 (d, J=6.2 Hz, 3H).

Example 27: (5S)-3-[[6-[3-(Difluoromethoxy)-4-fluoro-phenyl]-3-methyl-pyrazin-2-yl]methyl]-5-methyl-oxazolidin-2-one

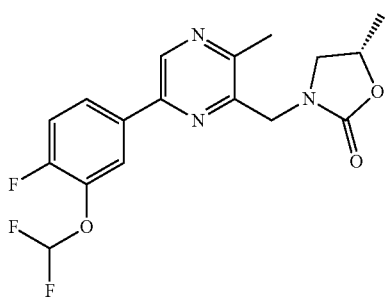 [SMILES: Cc1ncc(-c2ccc(F)c(OC(F)F)c2)nc1CN1C[C@H](C)OC1=O]

Prepared analogous to Example 3, using (S)-5-Methyl-oxazolidin-2-one (Intermediate 3) and 3-(Chloromethyl)-5-(3-(difluoromethoxy)-4-fluorophenyl)-2-methylpyrazine (Intermediate 13). MS (ESI): mass calcd. for $C_{17}H_{16}F_3N_3O_3$, 367.1; m/z found, 368 [M+H]$^+$. $^1$H NMR (400 MHz, CDCl$_3$) δ 8.80 (s, 1H), 7.94 (d, J=7.4 Hz, 1H), 7.87-7.79 (m, 1H), 7.33-7.27 (m, 1H), 6.64 (t, J=73.2 Hz, 1H), 4.74 (dd, J=13.9, 7.0 Hz, 1H), 4.70-4.58 (m, 2H), 3.78 (t, J=8.2 Hz, 1H), 3.32 (t, J=7.7 Hz, 1H), 2.63 (s, 3H), 1.47 (d, J=6.2 Hz, 3H).

Example 28: 3-[[6-[3-(Difluoromethoxy)-4-fluoro-phenyl]-3-methyl-pyrazin-2-yl]methyl]-1,3-oxazinan-2-one

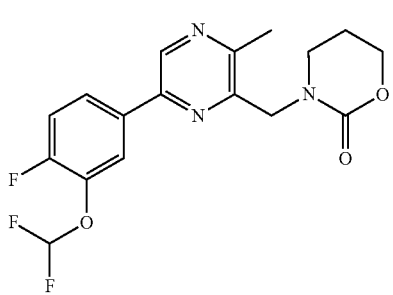 [SMILES: Cc1ncc(-c2ccc(F)c(OC(F)F)c2)nc1CN1CCCOC1=O]

Prepared analogous to Example 3, using 1,3-oxazinan-2-one and 3-(Chloromethyl)-5-(3-(difluoromethoxy)-4-fluorophenyl)-2-methylpyrazine (Intermediate 13). MS (ESI): mass calcd. for $C_{17}H_{16}F_3N_3O_3$, 367.1; m/z found, [M+H]$^+$. $^1$H NMR (300 MHz, CDCl$_3$) δ 8.77 (s, 1H), 7.95 (d, J=7.5 Hz, 1H), 7.80 (ddd, J=8.6, 4.3, 2.2 Hz, 1H), 7.40-7.25 (m, 1H), 6.63 (t, J=73.2 Hz, 1H), 4.72 (s, 2H), 4.48-4.27 (m, 2H), 3.53 (t, J=6.2 Hz, 2H), 2.62 (s, 3H), 2.29-2.02 (m, 2H).

Example 29: 5-[[6-[4-Chloro-3-(difluoromethoxy)phenyl]pyrazin-2-yl]methyl]-7-oxa-5-azaspiro[2.4]heptan-6-one

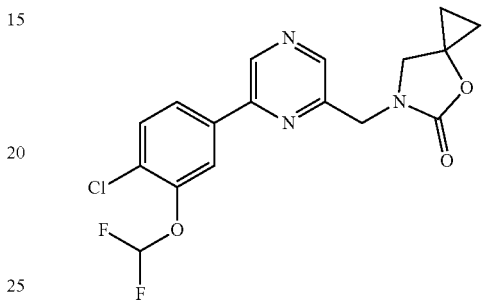

Prepared analogous to Example 3, using 2-(4-Chloro-3-(difluoromethoxy)phenyl)-6-(chloromethyl)pyrazine (Intermediate 9). MS (ESI): mass calcd. for $C_{17}H_{14}ClF_2N_3O_3$, 381.1; m/z found, 382 [M+H]$^+$. $^1$H NMR (300 MHz, CDCl$_3$) δ 8.97 (s, 1H), 8.62 (s, 1H), 7.98 (s, 1H), 7.84 (d, J=8.4 Hz, 1H), 7.59 (d, J=8.4 Hz, 1H), 6.64 (t, J=73.1 Hz, 1H), 4.72 (s, 2H), 3.75 (s, 2H), 1.31-1.17 (m, 2H), 0.73 (t, J=6.9 Hz, 2H).

Example 30: 3-[[6-[4-Chloro-3-(difluoromethoxy)phenyl]pyrazin-2-yl]methyl]-5,5-dimethyl-oxazolidin-2-one

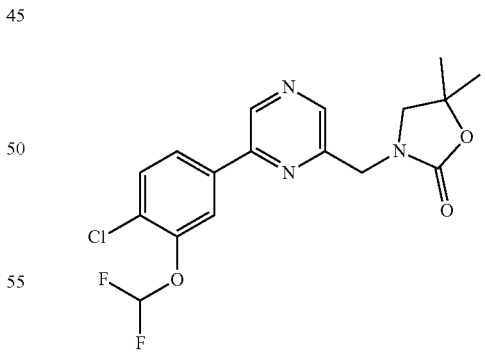

Prepared analogous to Example 3, using 5,5-dimethyl-oxazolidin-2-one and 2-(4-Chloro-3-(difluoromethoxy)phenyl)-6-(chloromethyl) pyrazine (Intermediate 9). MS (ESI): mass calcd. for $C_{17}H_{16}ClF_2N_3O_3$, 383.1; m/z found, 384 [M+H]$^+$. $^1$H NMR (300 MHz, CDCl$_3$) δ 8.95 (s, 1H), 8.57 (s, 1H), 7.96 (s, 1H), 7.83 (d, J=8.4 Hz, 1H), 7.59 (d, J=8.4 Hz, 1H), 6.63 (t, J=73.1 Hz, 1H), 4.67 (s, 2H), 3.44 (s, 2H), 1.48 (s, 6H).

Example 31: (5R)-3-[[6-[4-Chloro-3-(difluoromethoxy)phenyl]pyrazin-2-yl]methyl]-5-methyl-oxazolidin-2-one

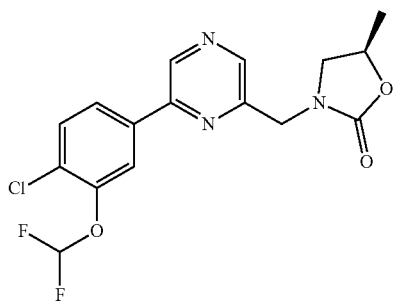 [SMILES: C[C@@H]1CN(Cc2cncc(-c3ccc(Cl)c(OC(F)F)c3)n2)C(=O)O1]

Prepared analogous to Example 3, using (R)-5-Methyl-oxazolidin-2-one (Intermediate 2) and 2-(4-Chloro-3-(difluoromethoxy)phenyl)-6-(chloromethyl)pyrazine (Intermediate 9). MS (ESI): mass calcd. for $C_{16}H_{14}ClF_2N_3O_3$, 369.1; m/z found, 370 [M+H]$^+$. $^1$H NMR (300 MHz, CDCl$_3$) δ 8.96 (s, 1H), 8.58 (s, 1H), 7.97 (s, 1H), 7.83 (d, J=8.3 Hz, 1H), 7.59 (d, J=8.3 Hz, 1H), 6.64 (t, J=73.1 Hz, 1H), 4.83-4.70 (m, 1H), 4.68 (s, J=8.4 Hz, 2H), 3.79 (t, J=8.2 Hz, 1H), 3.29 (t, J=7.6 Hz, 1H), 1.46 (d, J=6.1 Hz, 3H).

Example 32: (5S)-3-[[6-[4-Chloro-3-(difluoromethoxy)phenyl]pyrazin-2-yl]methyl]-5-methyl-oxazolidin-2-one

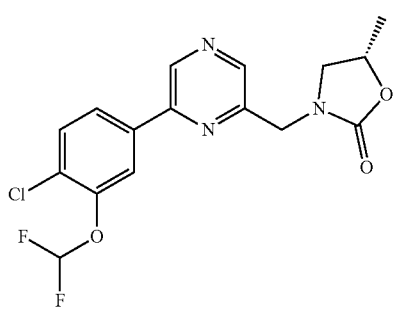 [SMILES: C[C@H]1CN(Cc2cncc(-c3ccc(Cl)c(OC(F)F)c3)n2)C(=O)O1]

Prepared analogous to Example 3, using (S)-5-Methyl-oxazolidin-2-one (Intermediate 3) and 2-(4-Chloro-3-(difluoromethoxy)phenyl)-6-(chloromethyl)pyrazine (Intermediate 9). MS (ESI): mass calcd. for $C_{16}H_{14}ClF_2N_3O_3$, 369.1; m/z found, 370 [M+H]$^+$. $^1$H NMR (300 MHz, CDCl$_3$) δ 8.96 (s, 1H), 8.58 (s, 1H), 7.97 (s, 1H), 7.83 (d, J=8.3 Hz, 1H), 7.59 (d, J=8.4 Hz, 1H), 6.64 (t, J=73.1 Hz, 1H), 4.72 (dd, J=13.9, 7.0 Hz, 1H), 4.66 (s, 2H), 3.79 (t, J=8.3 Hz, 1H), 3.29 (t, J=7.6 Hz, 1H), 1.46 (d, J=6.2 Hz, 3H).

Example 33: (4R)-3-[[6-[4-Chloro-3-(difluoromethoxy)phenyl]pyrazin-2-yl]methyl]-4-methyl-oxazolidin-2-one

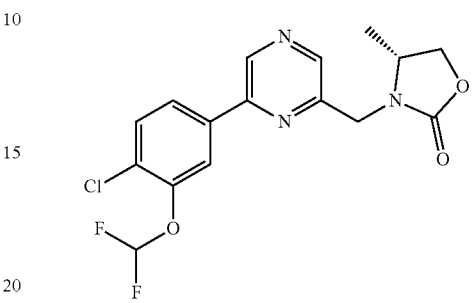

Prepared analogous to Example 3, using (R)-4-methyl-oxazolidin-2-one and 2-(4-Chloro-3-(difluoromethoxy)phenyl)-6-(chloromethyl)pyrazine (Intermediate 9). MS (ESI): mass calcd. for $C_{16}H_{14}ClF_2N_3O_3$, 369.1; m/z found, 370 [M+H]$^+$. $^1$H NMR (300 MHz, CDCl$_3$) δ 8.96 (s, 1H), 8.62 (s, 1H), 7.98 (s, 1H), 7.82 (d, J=8.1 Hz, 1H), 7.59 (d, J=8.2 Hz, 1H), 6.64 (t, J=73.1 Hz, 1H), 4.84 (d, J=16.1 Hz, 1H), 4.57-4.39 (m, 2H), 4.11-3.97 (m, 1H), 3.97-3.86 (m, 1H), 1.34 (d, J=5.7 Hz, 3H).

Example 34: (4S)-3-[[6-[4-Chloro-3-(difluoromethoxy)phenyl]pyrazin-2-yl]methyl]-4-methyl-oxazolidin-2-one

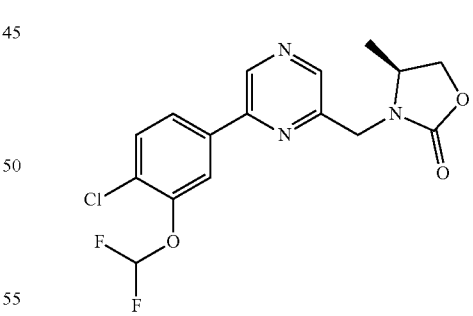

Prepared analogous to Example 3, using (S)-4-methyl-oxazolidin-2-one and 2-(4-Chloro-3-(difluoromethoxy)phenyl)-6-(chloromethyl)pyrazine (Intermediate 9). MS (ESI): mass calcd. for $C_{16}H_{14}ClF_2N_3O_3$, 369.1; m/z found, 370 [M+H]$^+$. $^1$H NMR (300 MHz, CDCl$_3$) δ 8.96 (s, 1H), 8.62 (s, 1H), 7.98 (s, 1H), 7.82 (d, J=8.2 Hz, 1H), 7.59 (d, J=8.3 Hz, 1H), 6.64 (t, J=73.1 Hz, 1H), 4.84 (d, J=16.2 Hz, 1H), 4.55-4.32 (m, 2H), 4.10-3.97 (m, 1H), 3.96-3.83 (m, 1H), 1.34 (d, J=5.8 Hz, 3H).

Example 35: 3-[[6-[4-Chloro-3-(difluoromethoxy)phenyl]pyrazin-2-yl]methyl]-1,3-oxazinan-2-one

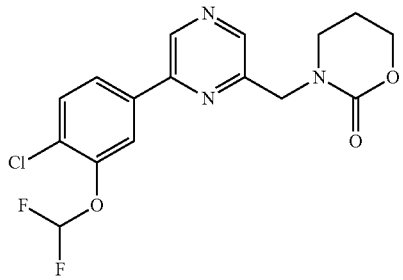 [SMILES: O=C1OCCCN1Cc1cncc(-c2ccc(Cl)c(OC(F)F)c2)n1]

Prepared analogous to Example 3, using 1,3-oxazinan-2-one and 2-(4-Chloro-3-(difluoromethoxy)phenyl)-6-(chloromethyl)pyrazine (Intermediate 9). MS (ESI): mass calcd. for $C_{16}H_{14}ClF_2N_3O_3$, 369.1; m/z found, 370 [M+H]$^+$. $^1$H NMR (300 MHz, CDCl$_3$) δ 8.93 (s, 1H), 8.62 (s, 1H), 7.98 (s, 1H), 7.86-7.77 (m, 1H), 7.59 (d, J=8.4 Hz, 1H), 6.63 (t, J=73.1 Hz, 1H), 4.74 (s, 2H), 4.42-4.28 (m, 2H), 3.57 (t, J=6.1 Hz, 2H), 2.21-2.04 (m, 2H).

Example 36: 5-[[6-[4-Chloro-3-(difluoromethoxy)phenyl]-3-methyl-pyrazin-2-yl]methyl]-7-oxa-5-azaspiro[2.4]heptan-6-one

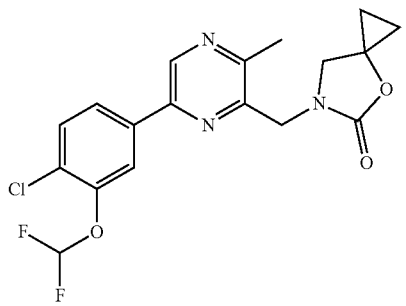 [SMILES: Cc1ncc(-c2ccc(Cl)c(OC(F)F)c2)nc1CN1CC2(CC2)OC1=O]

Prepared analogous to Example 3, using 5-(4-Chloro-3-(difluoromethoxy)phenyl)-3-(chloromethyl)-2-methylpyrazine (Intermediate 15). MS (ESI): mass calcd. for $C_{18}H_{16}ClF_2N_3O_3$, 395.1; m/z found, 396 [M+H]$^+$. $^1$H NMR (400 MHz, CDCl$_3$) δ 8.84 (s, 1H), 7.96 (s, 1H), 7.81 (dd, J=8.4, 2.0 Hz, 1H), 7.56 (d, J=8.4 Hz, 1H), 6.63 (t, J=733 Hz, 1H), 4.70 (s, 2H), 3.78 (s, 2H), 2.66 (s, 3H), 1.28 (t, J=7.1 Hz, 2H), 0.75-0.69 (t, 2H).

Example 37: 3-[[6-[4-Chloro-3-(difluoromethoxy)phenyl]-3-methyl-pyrazin-2-yl]methyl]-1,3-oxazinan-2-one

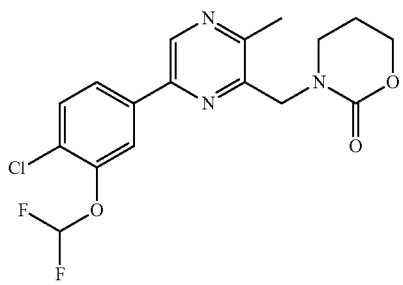 [SMILES: Cc1ncc(-c2ccc(Cl)c(OC(F)F)c2)nc1CN1CCCOC1=O]

Prepared analogous to Example 3, using 1,3-oxazinan-2-one and 5-(4-Chloro-3-(difluoromethoxy)phenyl)-3-(chloromethyl)-2-methylpyrazine (Intermediate 15). MS (ESI): mass calcd. for $C_{17}H_{16}ClF_2N_3O_3$, 383.1; m/z found, 0-2064-1 [M+H]$^+$.

Example 38: 5-[[6-[3-(1,1-Difluoroethyl)phenyl]pyrazin-2-yl]methyl]-7-oxa-5-azaspiro[2.4]heptan-6-one

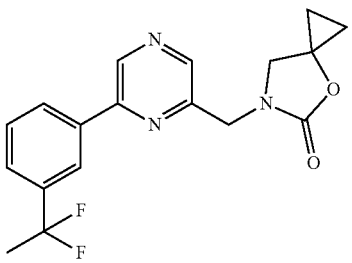 [SMILES: CC(F)(F)c1cccc(-c2cncc(CN3CC4(CC4)OC3=O)n2)c1]

Prepared analogous to Example 3, using 2-(Chloromethyl)-6-(3-(1,1-difluoroethyl)phenyl)pyrazine (Intermediate 10). MS (ESI): mass calcd. for $C_{18}H_{17}F_2N_3O_2$, 345.1; m/z found, 346 [M+H]$^+$. $^1$H NMR (300 MHz, CDCl$_3$) δ 9.01 (s, 1H), 8.61 (s, 1H), 8.21 (s, 1H), 8.08 (d, J=7.2 Hz, 1H), 7.67-7.53 (m, 2H), 4.74 (s, 2H), 3.78 (s, 2H), 1.99 (t, J=18.2 Hz, 3H), 1.26 (t, J=6.9 Hz, 2H), 0.77-0.69 (m, 2H).

Example 39: 3-[[6-[3-(1,1-Difluoroethyl)phenyl]pyrazin-2-yl]methyl]-5,5-dimethyl-oxazolidin-2-one

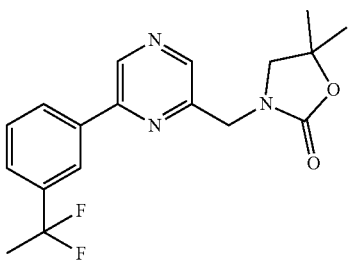 [SMILES: CC1(C)CN(Cc2cncc(-c3cccc(C(C)(F)F)c3)n2)C(=O)O1]

Prepared analogous to Example 3, using 5,5-dimethyl-oxazolidin-2-one and 2-(Chloromethyl)-6-(3-(1,1-difluoroethyl)phenyl)pyrazine (Intermediate 10). MS (ESI): mass calcd. for $C_{18}H_{19}F_2N_3O_2$, 347.1; m/z found, 348 [M+H]$^+$. $^1$H NMR (300 MHz, CDCl$_3$) δ 8.99 (s, 1H), 8.56 (s, 1H), 8.20 (s, 1H), 8.07 (d, J=6.9 Hz, 1H), 7.59 (d, J=10.9 Hz, 2H), 4.68 (s, 2H), 3.46 (s, 2H), 1.99 (t, J=18.2 Hz, 3H), 1.49 (s, 6H).

Example 40: (5R)-3-[[6-[3-(1,1-Difluoroethyl)phenyl]pyrazin-2-yl]methyl]-5-methyl-oxazolidin-2-one

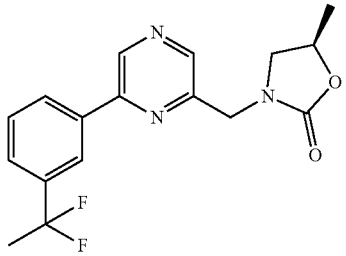 [SMILES: C[C@@H]1CN(Cc2cncc(-c3cccc(C(C)(F)F)c3)n2)C(=O)O1]

Prepared analogous to Example 3, using (R)-5-Methyl-oxazolidin-2-one (Intermediate 2) and 2-(Chloromethyl)-6-(3-(1,1-difluoroethyl)phenyl)pyrazine (Intermediate 10). MS (ESI): mass calcd. for $C_{17}H_{17}F_2N_3O_2$, 333.1; m/z found, 334 [M+H]$^+$. $^1$H NMR (300 MHz, CDCl$_3$) δ 9.00 (s, 1H), 8.57 (s, 1H), 8.19 (s, 1H), 8.08 (d, J=7.1 Hz, 1H), 7.67-7.53 (m, 2H), 4.79-4.69 (m, 1H), 4.68 (s, 2H), 3.79 (t, J=8.3 Hz, 1H), 3.31 (t, J=7.6 Hz, 1H), 1.99 (t, J=18.2 Hz, 3H), 1.47 (d, J=6.2 Hz, 3H).

Example 41: (5S)-3-[[6-[3-(1,1-Difluoroethyl)phenyl]pyrazin-2-yl]methyl]-5-methyl-oxazolidin-2-one

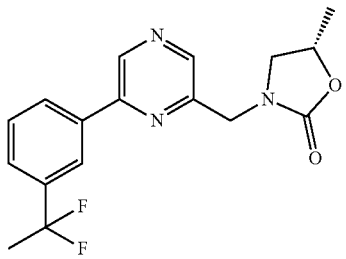 [SMILES: C[C@H]1CN(Cc2cncc(-c3cccc(C(C)(F)F)c3)n2)C(=O)O1]

Prepared analogous to Example 3, using (S)-5-Methyl-oxazolidin-2-one (Intermediate 3) and 2-(Chloromethyl)-6-(3-(1,1-difluoroethyl)phenyl)pyrazine (Intermediate 10). MS (ESI): mass calcd. for $C_{17}H_{17}F_2N_3O_2$, 333.1; m/z found, 334 [M+H]$^+$. $^1$H NMR (300 MHz, CDCl$_3$) δ 9.00 (s, 1H), 8.57 (s, 1H), 8.20 (s, 1H), 8.08 (d, J=6.7 Hz, 1H), 7.67-7.51 (m, 2H), 4.73 (dd, J=12.8, 5.9 Hz, 1H), 4.68 (s, 2H), 3.79 (t, J=8.2 Hz, 1H), 3.31 (t, J=7.5 Hz, 1H), 1.99 (t, J=18.1 Hz, 3H), 1.47 (d, J=6.1 Hz, 3H).

Example 42: 3-[[6-[3-(1,1-Difluoroethyl)phenyl]pyrazin-2-yl]methyl]-1,3-oxazinan-2-one

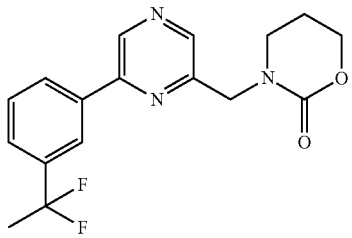 [SMILES: CC(F)(F)c1cccc(-c2cncc(CN3CCCOC3=O)n2)c1]

Prepared analogous to Example 3, using 1,3-oxazinan-2-one and 2-(Chloromethyl)-6-(3-(1,1-difluoroethyl)phenyl)pyrazine (Intermediate 10). MS (ESI): mass calcd. for $C_{17}H_{17}F_2N_3O_2$, 333.1; m/z found, 334 [M+H]$^+$. $^1$H NMR (300 MHz, CDCl$_3$) δ 9.00 (s, 1H), 8.64 (s, 1H), 8.22 (s, 1H), 8.09 (d, J=7.1 Hz, 1H), 7.61 (d, J=8.0 Hz, 2H), 4.78 (s, 2H), 4.43-4.32 (m, 2H), 3.59 (t, J=6.1 Hz, 2H), 2.21-2.09 (m, 2H), 2.01 (t, J=18.2 Hz, 3H).

Example 43: 5-[[6-[3-(1,1-Difluoroethyl)phenyl]-3-methyl-pyrazin-2-yl]methyl]-7-oxa-5-azaspiro[2.4]heptan-6-one

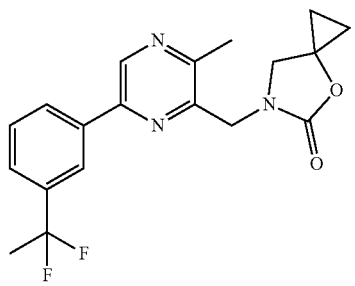 [SMILES: Cc1ncc(-c2cccc(C(C)(F)F)c2)nc1CN1CC2(CC2)OC1=O]

Prepared analogous to Example 3, using 3-(Chloromethyl)-5-(3-(1,1-difluoroethyl)phenyl)-2-methylpyrazine (Intermediate 12). MS (ESI): mass calcd. for $C_{19}H_{19}F_2N_3O_2$, 359.1; m/z found, 360 [M+H]$^+$. $^1$H NMR (300 MHz, CDCl$_3$) δ 8.89 (s, 1H), 8.21 (s, 1H), 8.06 (d, J=6.1 Hz, 1H), 7.72-7.41 (m, 2H), 4.72 (s, 2H), 3.80 (s, 2H), 2.67 (s, 3H), 1.99 (t, J=18.1 Hz, 3H), 1.41-1.21 (m, 2H), 0.79-0.70 (m, 2H).

Example 44: 3-[[6-[3-(1,1-Difluoroethyl)phenyl]-3-methyl-pyrazin-2-yl]methyl]-5,5-dimethyl-oxazolidin-2-one

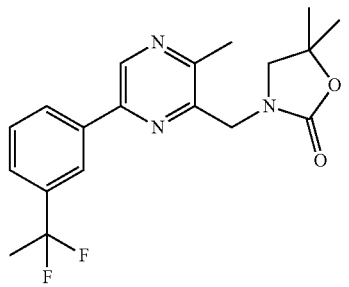 [SMILES: Cc1ncc(-c2cccc(C(C)(F)F)c2)nc1CN1CC(C)(C)OC1=O]

Prepared analogous to Example 3, using 5,5-dimethyl-oxazolidin-2-one and 3-(Chloromethyl)-5-(3-(1,1-difluoroethyl)phenyl)-2-methylpyrazine (Intermediate 12). MS (ESI): mass calcd. for $C_{19}H_{21}F_2N_3O_2$, 361.2; m/z found, 362[M+H]$^+$. $^1$H NMR (300 MHz, CDCl$_3$) δ 8.86 (s, 1H), 8.17 (s, 1H), 8.03 (d, J=6.2 Hz, 1H), 7.68-7.41 (m, 2H), 4.67 (s, 2H), 3.48 (s, 2H), 2.65 (s, 3H), 1.98 (t, J=18.1 Hz, 3H), 1.50 (s, 6H).

Example 45: 3-[[6-[3-(1,1-Difluoroethyl)phenyl]-3-methyl-pyrazin-2-yl]methyl]-1,3-oxazinan-2-one

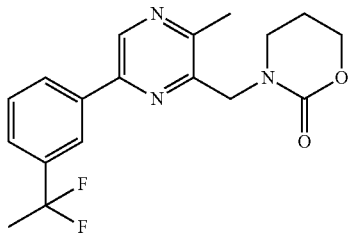 [SMILES: Cc1ncc(-c2cccc(C(C)(F)F)c2)nc1CN1CCCOC1=O]

Prepared analogous to Example 3, using 1,3-oxazinan-2-one and 3-(Chloromethyl)-5-(3-(1,1-difluoroethyl)phenyl)-2-methylpyrazine (Intermediate 12). MS (ESI): mass calcd. for $C_{18}H_{19}F_2N_3O_2$, 347.1; m/z found, 348 [M+H]$^+$. $^1$H NMR (300 MHz, CDCl$_3$) δ 8.84 (s, 1H), 8.20 (s, 1H), 8.02 (d, J=5.6 Hz, 1H), 7.62-7.50 (m, 2H), 4.74 (s, 2H), 4.45-4.35 (m, 2H), 3.59-3.47 (m, 2H), 2.62 (s, 3H), 2.23-2.10 (m, 2H), 1.98 (t, J=18.2 Hz, 3H).

Example 46: (4R)-3-[[6-[3-(1,1-Difluoroethyl)-4-fluoro-phenyl]pyrazin-2-yl]methyl]-4-methyl-oxazolidin-2-one

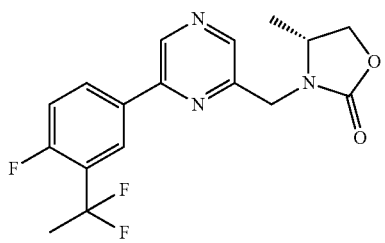 [SMILES: C[C@@H]1COC(=O)N1Cc1cncc(-c2ccc(F)c(C(C)(F)F)c2)n1]

Prepared analogous to Example 3, using (R)-4-methyl-oxazolidin-2-one and 2-(Chloromethyl)-6-(3-(1,1-difluoroethyl)-4-fluorophenyl)pyrazine (Intermediate 11). MS (ESI): mass calcd. for $C_{17}H_{16}F_3N_3O_2$, 351.1; m/z found, 352 [M+H]$^+$. $^1$H NMR (300 MHz, CDCl$_3$) δ 8.89 (s, 1H), 8.53 (s, 1H), 8.17 (dd, J=7.1, 2.1 Hz, 1H), 8.06-7.97 (m, 1H), 7.26-7.17 (t, 1H+CDCl$_3$), 4.78 (d, J=16.1 Hz, 1H), 4.46-4.34 (m, 2H), 3.91 (ddd, J=27.8, 14.4, 7.4 Hz, 2H), 2.07-1.90 (m, 3H), 1.27 (d, J=6.0 Hz, 3H).

Example 47: (4S)-3-[[6-[3-(1,1-Difluoroethyl)-4-fluoro-phenyl]pyrazin-2-yl]methyl]-4-methyl-oxazolidin-2-one

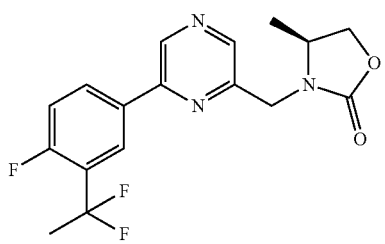 [SMILES: C[C@H]1COC(=O)N1Cc1cncc(-c2ccc(F)c(C(C)(F)F)c2)n1]

Prepared analogous to Example 3, using (S)-4-methyl-oxazolidin-2-one and 2-(Chloromethyl)-6-(3-(1,1-difluoroethyl)-4-fluorophenyl)pyrazine (Intermediate 11). MS (ESI): mass calcd. for $C_{17}H_{16}F_3N_3O_2$, 351.1; m/z found, 352 [M+H]$^+$. $^1$H NMR (300 MHz, CDCl$_3$) δ 8.89 (s, 1H), 8.53 (s, 1H), 8.17 (dd, J=7.1, 2.1 Hz, 1H), 8.06-7.97 (m, 1H), 7.25-7.15 (t, 1H+CDCl$_3$), 4.78 (d, J=16.1 Hz, 1H), 4.47-4.35 (m, 2H), 3.91 (ddd, J=27.8, 14.4, 7.4 Hz, 2H), 2.07-1.90 (m, 3H), 1.27 (d, J=6.0 Hz, 3H).

Example 48: 6-[[6-[3-(1,1-Difluoroethyl)phenyl]pyrazin-2-yl]methyl]-8-oxa-6-azaspiro[2.5]octan-7-one

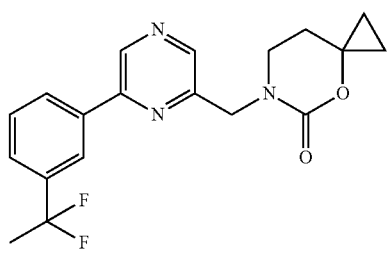 [SMILES: CC(F)(F)c1cccc(-c2cncc(CN3CCC4(CC4)OC3=O)n2)c1]

Step A: 1-(2-(((6-(3-(1,1-Difluoroethyl)phenyl)pyrazin-2-yl)methyl)amino)ethyl) cyclopropan-1-ol. In a sealed tube, a mixture of (6-(3-(1,1-Difluoroethyl)phenyl)pyrazin-2-yl)methanamine (Intermediate 16) (0.2 g, 0.8 mmol, 1 equiv), 1-(2-Chloroethyl)cyclopropan-1-ol (Intermediate 4) (0.101 mg, 0.75 mmol, 1 equiv) (freshly prepared), KI (0.131 g, 0.79 mmol, 1.05 equiv), K$_2$CO$_3$ (0.209 g, 1.51 mmol, 2 equiv), and acetonitrile (2 mL) was heated at 85° C. for 16 h. Upon completion, the reaction mixture was diluted with water and ethyl acetate. The organic layer was washed with brine, dried over MgSO$_4$, filtered, and concentrated under vacuum to give the title compound (268 mg, 0.72 mmol, 96%) as an orange oil. MS (ESI): mass calcd. for $C_{18}H_{21}F_2N_3O$, 333.2; m/z found, 334 [M+H]$^+$.

Step B: 6-[[6-[3-(1,1-Difluoroethyl)phenyl]pyrazin-2-yl]methyl]-8-oxa-6-azaspiro[2.5]octan-7-one. In a round bottom flask, a mixture of 1-(2-(((6-(3-(1,1-difluoroethyl)phenyl)pyrazin-2-yl)methyl)amino)ethyl)cyclopropan-1-ol (1 equiv), CDI (1 equiv) and THF (5 mL) was stirred at room temperature for 16 h. The reaction mixture was concentrated under reduced pressure, and the crude was purified by flash column chromatography (silica, AcOEt in Heptane from 0/100 to 30/70) to give the title compound as a colorless oil. This oil was dissolved in dioxane and 0.025 ml of HCl (4 min dioxane) was added. The solid was collected by filtration and washed with diethyl ether and dried under vacuum to give the title compound (14%) as the HCl salt. MS (ESI): mass calcd. for $C_{19}H_{19}F_2N_3O_2$, 359.1; m/z found, 360 [M+H]$^+$. $^1$H NMR of free base (300 MHz, CDCl$_3$) δ 9.00 (s, 1H), 8.63 (s, 1H), 8.23 (s, 1H), 8.10 (d, J=6.6 Hz, 1H), 7.68-7.54 (m, 2H), 4.83 (s, 2H), 3.67 (t, J=5.8 Hz, 2H), 2.09 (m, 2H), 2.01 (t, J=18.2 Hz, 3H), 1.16 (s, 2H), 0.70 (s, 2H).

Example 49: 6-[[6-[3-(Difluoromethoxy)-4-fluorophenyl]pyrazin-2-yl]methyl]-8-oxa-6-azaspiro[2.5]octan-7-one

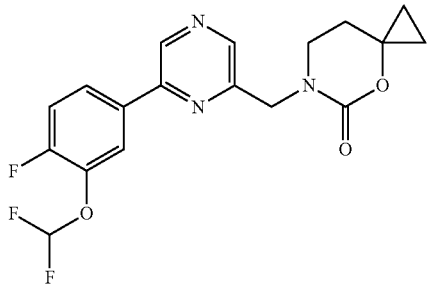 [SMILES: O=C1OC2(CCN1Cc1cncc(-c3ccc(F)c(OC(F)F)c3)n1)CC2]

Prepared analogous to Example 48, using (6-(3-(Difluoromethoxy)-4-fluorophenyl)pyrazin-2-yl)methanamine (Intermediate 17). MS (ESI): mass calcd. for C18H$_{16}$F$_3$N$_3$O$_3$, 379.1; 380 m/z found, [M+H]$^+$. $^1$H NMR of free base (300 MHz, CDCl$_3$) δ 8.92 (s, 1H), 8.60 (s, 1H), 7.99 (d, J=7.0 Hz, 1H), 7.87 (d, J=2.1 Hz, 1H), 7.31 (t, J=9.3 Hz, 1H), 6.64 (t, J=73.2 Hz, 1H), 4.78 (s, 2H), 3.64 (t, J=5.9 Hz, 2H), 2.06 (t, J=5.7 Hz, 2H), 1.13 (s, 2H), 0.67 (s, 2H).

Example 50: 6-[[6-[4-Chloro-3-(difluoromethoxy)phenyl]pyrazin-2-yl]methyl]-8-oxa-6-azaspiro[2.5]octan-7-one

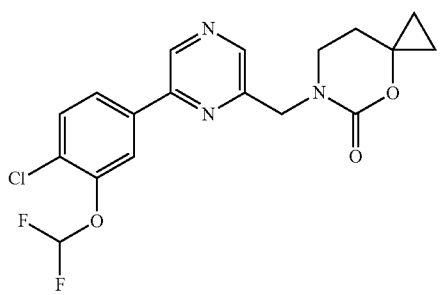 [SMILES: O=C1OC2(CCN1Cc1cncc(-c3ccc(Cl)c(OC(F)F)c3)n1)CC2]

Prepared analogous to Example 48, using (6-(4-Chloro-3-(difluoromethoxy)phenyl)pyrazin-2-yl)methanamine (Intermediate 18). MS (ESI): mass calcd. for C$_{18}$H$_{16}$ClF$_2$N$_3$O$_3$, 395.1; m/z found, 396 [M+H]$^+$. $^1$H NMR (300 MHz, CDCl$_3$) δ 8.96 (s, 1H), 8.64 (s, 1H), 8.01 (s, 1H), 7.86 (d, J=8.2 Hz, 1H), 7.61 (d, J=8.3 Hz, 1H), 6.66 (t, J=73.2 Hz, 1H), 4.81 (s, 2H), 3.68 (t, J=5.8 Hz, 2H), 2.09 (t, J=5.7 Hz, 2H), 1.16 (s, 2H), 0.70 (s, 2H).

Example 51: 6-[[6-[4-Chloro-3-(difluoromethoxy)phenyl]-3-methyl-pyrazin-2-yl]methyl]-8-oxa-6-azaspiro[2.5]octan-7-one

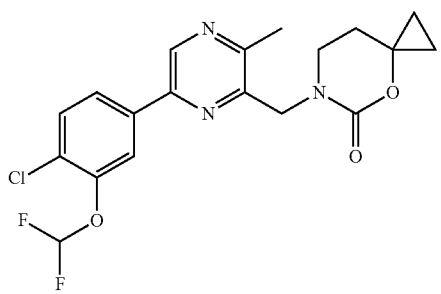 [SMILES: Cc1ncc(-c2ccc(Cl)c(OC(F)F)c2)nc1CN1CCC2(CC2)OC1=O]

Prepared analogous to Example 48, using (6-(4-Chloro-3-(difluoromethoxy)phenyl)-3-methylpyrazin-2-yl)methanamine (Intermediate 19). MS (ESI): mass calcd. for C$_{19}$H$_{18}$ClF$_2$N$_3$O$_3$, 409.1; m/z found, 0-2069-1 [M+H]$^+$.

Example 52: 6-[[6-[3-(Difluoromethyl)-4-fluorophenyl]pyrazin-2-yl]methyl]-8-oxa-6-azaspiro[2.5]octan-7-one

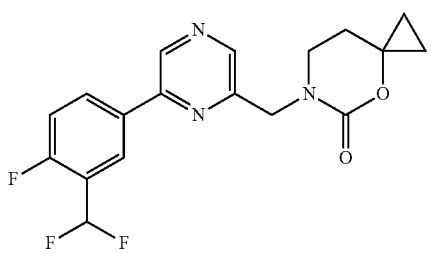 [SMILES: O=C1OC2(CCN1Cc1cncc(-c3ccc(F)c(C(F)F)c3)n1)CC2]

Prepared analogous to Example 48, using (6-(3-(Difluoromethyl)-4-fluorophenyl)pyrazin-2-yl)methanamine (Intermediate 20). MS (ESI): mass calcd. for C18H$_{16}$F$_3$N$_3$O$_2$, 363.1; m/z found, 364 [M+H]$^+$. $^1$H NMR (300 MHz, CDCl$_3$) δ 8.88 (s, 1H), 8.54 (s, 1H), 8.24 (d, J=5.2 Hz, 1H), 8.08 (s, 1H), 7.32-7.27 (m, 1H), 6.90 (t, J=54.8 Hz, 1H), 4.72 (s, 2H), 3.58 (t, J=5.7 Hz, 2H), 2.00 (t, J=5.6 Hz, 2H), 1.07 (s, 2H), 0.61 (s, 2H).

Example 53: 6-[[6-[3-(Difluoromethyl)-4-fluorophenyl]-3-methyl-pyrazin-2-yl]methyl]-8-oxa-6-azaspiro[2.5]octan-7-one

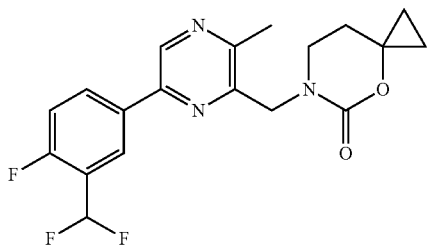 [SMILES: Cc1ncc(-c2ccc(F)c(C(F)F)c2)nc1CN1CCC2(CC2)OC1=O]

Prepared analogous to Example 48, using (6-(3-(Difluoromethyl)-4-fluorophenyl)-3-methylpyrazin-2-yl)methanamine (Intermediate 21). MS (ESI): mass calcd. for C$_{19}$H$_{18}$F$_3$N$_3$O$_2$, 377.1; m/z found, 378 [M+H]$^+$. $^1$H NMR (300 MHz, CDCl$_3$) δ 8.81 (s, 1H), 8.27 (d, J=5.8 Hz, 1H), 8.16-8.05 (m, 1H), 7.32-7.21 (m, 1H+CDCl$_3$), 6.97 (t, J=54.9 Hz, 1H), 4.78 (s, 2H), 3.62 (t, J=6.1 Hz, 2H), 2.63 (s, 3H), 2.10 (t, J=6.1 Hz, 2H), 1.15 (t, J=6.5 Hz, 2H), 0.69 (q, J=6.2 Hz, 2H).

Example 54: 6-[[6-[3-(Difluoromethoxy)-4-fluorophenyl]-3-methyl-pyrazin-2-yl]methyl]-8-oxa-6-azaspiro[2.5]octan-7-one

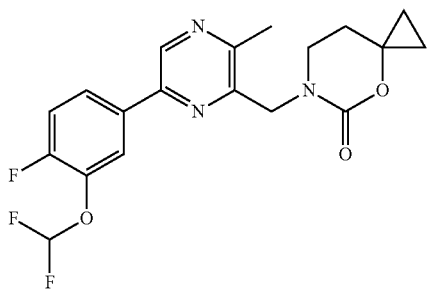 [SMILES: Cc1ncc(-c2ccc(F)c(OC(F)F)c2)nc1CN1CCC2(CC2)OC1=O]

Prepared analogous to Example 48, using (6-(3-(Difluoromethoxy)-4-fluorophenyl)-3-methylpyrazin-2-yl)methanamine (Intermediate 22). MS (ESI): mass calcd. for $C_{19}H_{18}F_3N_3O_3$, 393.1; m/z found, 394 [M+H]$^+$. $^1$H NMR (400 MHz, CDCl$_3$) δ 8.78 (s, 1H), 7.96 (dd, J=7.5, 2.0 Hz, 1H), 7.84 (ddd, J=8.6, 4.4, 2.2 Hz, 1H), 7.32-7.26 (m, 1H), 6.63 (t, J=73.3 Hz, 1H), 4.77 (s, 2H), 3.61 (t, J=6.1 Hz, 2H), 2.62 (s, 3H), 2.09 (t, J=6.1 Hz, 2H), 1.15 (t, J=6.5 Hz, 2H), 0.69 (q, J=6.1 Hz, 2H).

Example 55: (R/S)-3-[[6-[4-Chloro-3-(difluoromethoxy)phenyl]pyrazin-2-yl]methyl]-N,N-dimethyl-2-oxo-oxazolidine-5-carboxamide

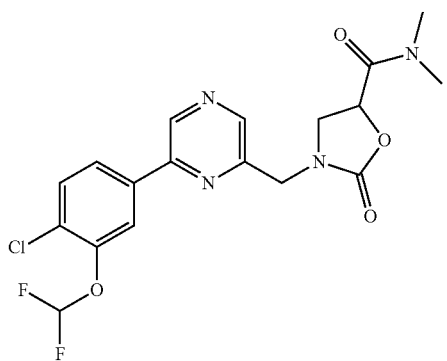 [SMILES: CN(C)C(=O)C1CN(Cc2cncc(-c3ccc(Cl)c(OC(F)F)c3)n2)C(=O)O1]

Step A: Benzyl 3-((6-(4-chloro-3-(difluoromethoxy)phenyl)pyrazin-2-yl)methyl)-2-oxooxazolidine-5-carboxylate. Prepared analogous to Example 3, using (R/S)-Benzyl 2-oxooxazolidine-5-carboxylate (Intermediate 5) and 2-(4-Chloro-3-(difluoromethoxy)phenyl)-6-(chloromethyl)pyrazine (Intermediate 9).

Step B: 3-((6-(4-Chloro-3-(difluoromethoxy)phenyl)pyrazin-2-yl)methyl)-2-oxooxazolidine-5-carboxylic acid. In a round bottom flask equipped with a condenser, a solution of LiOH (0.154 g 3.7 mmol, 2 equiv) in water (15 mL) was added to a solution of benzyl 3-((6-(4-chloro-3-(difluoromethoxy)phenyl)pyrazin-2-yl)methyl)-2-oxooxazolidine-5-carboxylate (0.9 g, 1.8 mmol, 1 equiv) in MeOH (30 mL). The reaction mixture was stirred at rt for 1 h. The crude reaction mixture was washed with water and AcOEt. The organic layer was discarded, and the aqueous layer was acidified with a few drops of 10% HCl solution to pH around 2. Then, it was extracted with AcOEt and the organic layer separated, dried over MgSO$_4$, filtered, and concentrated under reduced pressure to obtain the title compound (500 mg, 1.25 mmol, 68%), which was used without further purification. MS (ESI): mass calcd. for $C_{16}H_{12}ClF_2N_3O_5$, 399.0; m/z found, 400 [M+H]$^+$.

Step C: (R/S)-3-[[6-[4-Chloro-3-(difluoromethoxy)phenyl]pyrazin-2-yl]methyl]-N,N-dimethyl-2-oxo-oxazolidine-5-carboxamide. In a round bottom flask, oxalyl chloride (44.03 µL, 0.52 mmol, 2 equiv) was added dropwise to a mixture of 3-((6-(4-chloro-3-(difluoromethoxy)phenyl)pyrazin-2-yl)methyl)-2-oxooxazolidine-5-carboxylic acid (104 mg, 0.26 mmol, 1 equiv), DMF (0.437 µL, 0.006 mmol, 0.02 equiv) and DCM (1.5 mL) at room temperature, and the mixture was stirred at room temperature for 2 h. Then, dimethylamine (1.3 mL, 2.6 mmol, 2.0 M in THF, 10 equiv) was added dropwise, and the reaction mixture was stirred for an additional 2 hours at room temperature. Upon completion, the reaction mixture was concentrated, and the residue was purified by flash column chromatography (silica; gradient of DCM/MeOH (9:1) in DCM 0/100 to 10/90) to give the title compound (40 mg, 0.09 mmol, 35%). MS (ESI): mass calcd. for C18H$_{17}$ClF$_2$N$_4$O$_4$, 426.1; m/z found, 427 [M+H]$^+$. $^1$H NMR (300 MHz, CDCl$_3$) δ 8.96 (s, 1H), 8.58 (s, 1H), 8.00 (s, 1H), 7.82 (d, J=8.2 Hz, 1H), 7.58 (d, J=8.2 Hz, 1H), 6.74 (t, J=73.2 Hz, 1H), 5.27-5.10 (m, 1H), 4.69 (s, 2H), 4.50-4.36 (m, 1H), 3.76 (t, J=8.7 Hz, 1H), 3.18 (s, 3H), 3.01 (s, 3H).

Example 56: (R/S)-3-[[6-[4-Chloro-3-(difluoromethoxy)phenyl]pyrazin-2-yl]methyl]-N-methyl-2-oxo-oxazolidine-5-carboxamide

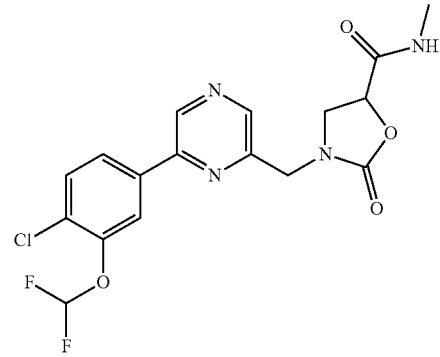 [SMILES: CNC(=O)C1CN(Cc2cncc(-c3ccc(Cl)c(OC(F)F)c3)n2)C(=O)O1]

Prepared analogous to Example 55, using methylamine in Step C. MS (ESI): mass calcd. for C17H15ClF2N4O4, 412.1; m/z found, 413 [M+H]$^+$. 1H NMR (300 MHz, CDCl3) δ 8.97 (s, 1H), 8.55 (s, 1H), 7.93 (s, 1H), 7.80 (s, 1H), 7.60 (d, J=6.8 Hz, 1H), 6.68 (t, J=73.0 Hz, 1H), 6.58 (s, 1H), 4.90 (s, 1H), 4.66 (s, 2H), 4.01 (s, 1H), 3.91 (s, 1H), 2.85 (s, 3H).

Example 57: 5-(Azetidine-1-carbonyl)-3-[[6-[4-chloro-3-(difluoromethoxy)phenyl]pyrazin-2-yl]methyl]oxazolidin-2-one

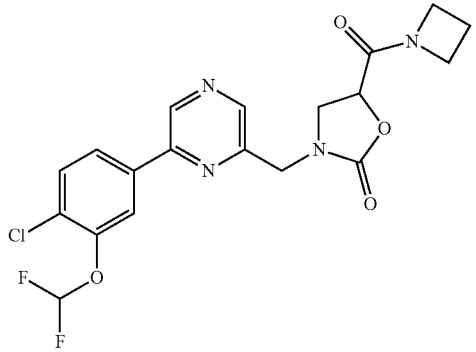 [SMILES: O=C1OC(C(=O)N2CCC2)CN1Cc1cncc(-c2ccc(Cl)c(OC(F)F)c2)n1]

Prepared analogous to Example 55, using azetidine in Step C. MS (ESI): mass calcd. for C$_{19}$H$_{17}$ClF$_2$N$_4$O$_4$, 438.1; m/z found, 439 [M+H]$^+$. $^1$H NMR (300 MHz, CDCl$_3$) δ 8.96 (s, 1H), 8.56 (s, 1H), 7.96 (s, 1H), 7.82 (d, J=8.0 Hz, 1H), 7.59 (d, J=8.1 Hz, 1H), 6.72 (t, J=73.2 Hz, 1H), 4.95 (s, 1H), 4.67 (s, 2H), 4.65-4.35 (m, 2H), 4.10 (s, 3H), 3.85 (s, 1H), 2.33 (s, 2H).

Example 58: (R/S)-5-(Azetidine-1-carbonyl)-3-[[6-[3-(difluoromethyl)-4-fluoro-phenyl]pyrazin-2-yl]methyl]oxazolidin-2-one

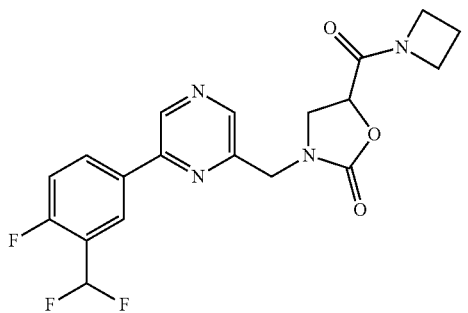 [SMILES: O=C1OC(C(=O)N2CCC2)CN1Cc1cncc(-c2ccc(F)c(C(F)F)c2)n1]

Prepared analogous to Example 55, using 2-(Chloromethyl)-6-(3-(difluoromethyl)-4-fluorophenyl)pyrazine (Intermediate 7) in Step A and azetidine in Step C. MS (ESI): mass calcd. for C$_{19}$H$_{17}$F$_3$N$_4$O$_3$, 406.1; m/z found, 407 [M+H]$^+$. $^1$H NMR (300 MHz, CDCl$_3$) δ 8.98 (s, 1H), 8.57 (s, 1H), 8.27 (d, J=5.9 Hz, 1H), 8.15 (m, 1H), 7.31 (t, J=9.2 Hz, 1H), 6.98 (t, J=54.8 Hz, 1H), 4.96 (dd, J=9.4, 5.6 Hz, 1H), 4.67 (s, 2H), 4.58-4.35 (m, 2H), 4.22-3.97 (m, 3H), 3.85 (t, J=9.2 Hz, 1H), 2.44-2.25 (m, 2H).

Example 59: (R/S)-3-[[6-[3-(Difluoromethyl)-4-fluoro-phenyl]pyrazin-2-yl]methyl]-N-methyl-2-oxo-oxazolidine-5-carboxamide

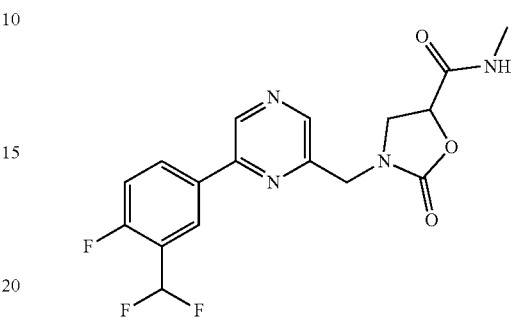

Prepared analogous to Example 55, using 2-(Chloromethyl)-6-(3-(difluoromethyl)-4-fluorophenyl)pyrazine (Intermediate 7) in Step A and methylamine in Step C. MS (ESI): mass calcd. for C$_{17}$H$_{15}$F$_3$N$_4$O$_3$, 380.1; m/z found, 380 [M+H]$^+$. $^1$H NMR (300 MHz, CDCl$_3$) δ 8.98 (s, 1H), 8.54 (s, 1H), 8.25 (d, J=5.9 Hz, 1H), 8.14 (dd, J=7.4, 4.0 Hz, 1H), 7.31 (t, J=9.3 Hz, 1H), 6.98 (t, J=54.8 Hz, 1H), 6.63 (s, 1H), 4.91 (dd, J=9.7, 5.5 Hz, 1H), 4.66 (s, 2H), 4.00 (t, J=9.4 Hz, 1H), 3.89 (dd, J=9.1, 5.6 Hz, 1H), 2.85 (d, J=4.9 Hz, 3H).

Example 60: (R/S)-3-[[6-[3-(Difluoromethoxy)-4-fluoro-phenyl]pyrazin-2-yl]methyl]-N-methyl-2-oxo-oxazolidine-5-carboxamide

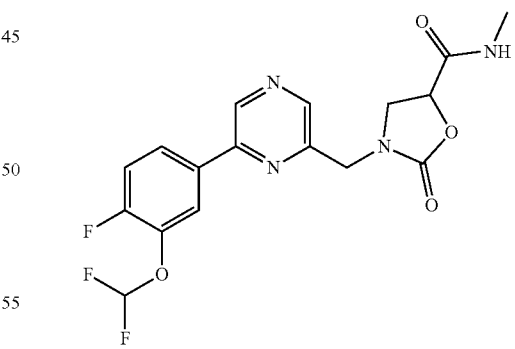

Prepared analogous to Example 55, using 2-(Chloromethyl)-6-(3-(difluoromethoxy)-4-fluorophenyl)pyrazine (Intermediate 8) in Step A and methylamine in Step C. MS (ESI): mass calcd. for C$_{17}$H$_{15}$F$_3$N$_4$O$_4$, 396.1; m/z found, 397 [M+H]$^+$. $^1$H NMR (300 MHz, CDCl$_3$) δ 8.97 (s, 1H), 8.55 (s, 1H), 7.96 (d, J=6.9 Hz, 1H), 7.87 (s, 1H), 7.35 (t, J=9.2 Hz, 1H), 6.69 (t, J=72, 6.70 Hz, 1H), 6.63 (s, 1H), 4.93 (dd, J=9.2, 5.3 Hz, 1H), 4.68 (s, 2H), 4.03 (t, J=9.3 Hz, 1H), 3.92 (dd, J=8.5, 5.6 Hz, 1H), 2.87 (d, J=4.5 Hz, 3H).

Example 61: ((R/S)-5-(Azetidine-1-carbonyl)-3-[[6-[3-(difluoromethoxy)-4-fluoro-phenyl]pyrazin-2-yl]methyl]oxazolidin-2-one

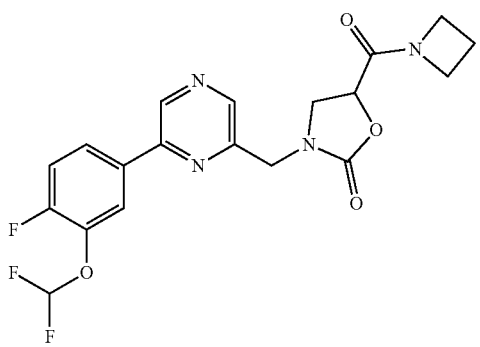 [SMILES: O=C1OC(C(=O)N2CCC2)CN1Cc1cncc(-c2ccc(F)c(OC(F)F)c2)n1]

Prepared analogous to Example 55, using 2-(Chloromethyl)-6-(3-(difluoromethoxy)-4-fluorophenyl)pyrazine (Intermediate 8) in Step A and azetidine in Step C. MS (ESI): mass calcd. for $C_{19}H_{17}F_3N_4O_4$, 422.1; m/z found, 423 [M+H]$^+$. $^1$H NMR (300 MHz, CDCl$_3$) δ 8.94 (s, 1H), 8.55 (s, 1H), 7.97 (d, J=6.6 Hz, 1H), 7.85 (bs, 1H), 7.33 (t, J=9.3 Hz, 1H), 6.70 (t, J=73.2 Hz, 1H), 4.94 (m, J=5.2 Hz, 1H), 4.66 (s, 2H), 4.58-4.35 (m, 2H), 4.09 (m, J=7.7 Hz, 3H), 3.85 (t, J=8.9 Hz, 1H), 2.34 (m, J=7.1 Hz, 2H).

Example 62: (R/S)-3-[[6-[3-(1,1-Difluoroethyl)-4-fluoro-phenyl]pyrazin-2-yl]methyl]-N,N-dimethyl-2-oxo-oxazolidine-5-carboxamide

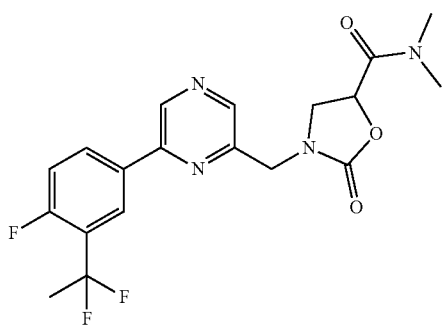 [SMILES: CN(C)C(=O)C1CN(Cc2cncc(-c3ccc(F)c(C(C)(F)F)c3)n2)C(=O)O1]

Prepared analogous to Example 55, using 2-(Chloromethyl)-6-(3-(1,1-difluoroethyl)-4-fluorophenyl)pyrazine (Intermediate 11) in Step A. MS (ESI): mass calcd. for $C_{19}H_{19}F_3N_4O_3$, 408.1; m/z found, 409 [M+H]$^+$. $^1$H NMR (300 MHz, CDCl$_3$) δ 8.97 (s, 1H), 8.58 (s, 1H), 8.23 (dd, J=7.1, 2.0 Hz, 1H), 8.15-8.07 (m, 1H), 7.32-7.23 (m, 1H+CDCl$_3$), 5.17 (dd, J=8.9, 6.1 Hz, 1H), 4.69 (q, J=16.2 Hz, 2H), 4.36 (dd, J=8.7, 6.1 Hz, 1H), 3.77 (t, J=8.8 Hz, 1H), 3.17 (s, 3H), 3.00 (s, J=4.4 Hz, 3H), 2.06 (dd, J=18.9, 18.3 Hz, 3H).

Example 63: (R/S)-3-[[6-[3-(1,1-Difluoroethyl)-4-fluoro-phenyl]pyrazin-2-yl]methyl]-N-methyl-2-oxo-oxazolidine-5-carboxamide Prepared analogous to Example 55, using 2-(Chloromethyl)-6-(3-(1,1-difluoroethyl)-4-fluorophenyl)pyrazine (Intermediate 11) in Step A and methylamine in Step C. MS (ESI): mass calcd. for $C18H_{17}F_3N_4O_3$, 394.1; m/z found, 395 [M+H]$^+$. $^1$H NMR (300 MHz, CDCl$_3$) δ 9.00 (s, 1H), 8.55 (s, 1H), 8.23 (dd, J=7.0, 2.0 Hz, 1H), 8.15-8.04 (m, 1H), 7.36-7.26 (t, 1H+CDCl$_3$), 6.64 (s, 1H), 4.93 (dd, J=9.7, 5.6 Hz, 1H), 4.68 (s, 2H), 4.03 (t, J=9.4 Hz, 1H), 3.88 (dd, J=9.1, 5.6 Hz, 1H), 2.87 (d, J=4.9 Hz, 3H), 2.08 (t, J=18.7 Hz, 3H).

Example 64: (R/S)-5-(Azetidine-1-carbonyl)-3-[[6-[3-(1,1-difluoroethyl)-4-fluoro-phenyl]pyrazin-2-yl]methyl]oxazolidin-2-one Prepared analogous to Example 55, using 2-(Chloromethyl)-6-(3-(1,1-difluoroethyl)-4-fluorophenyl)pyrazine (Intermediate 11) in Step A and azetidine in Step C. MS (ESI): mass calcd. for $C_{20}H_{19}F_3N_4O_3$, 420.1; m/z found, 421 [M+H]$^+$. $^1$H NMR (300 MHz, CDCl$_3$) δ 8.97 (s, 1H), 8.55 (s, 1H), 8.21 (dd, J=7.1, 2.0 Hz, 1H), 8.15-8.06 (m, 1H), 7.33-7.24 (m, 1H+CDCl$_3$), 4.95 (dd, J=9.4, 5.6 Hz, 1H), 4.73-4.60 (m, 2H), 4.57-4.37 (m, 2H), 4.07 (dt, J=8.9, 6.5 Hz, 3H), 3.86 (t, J=9.2 Hz, 1H), 2.40-2.26 (m, 2H), 2.06 (t, J=18.6 Hz, 3H).

Example 65: (R/S)-3-[[6-[3-(Difluoromethyl)-4-fluoro-phenyl]pyrazin-2-yl]methyl]-N,N-dimethyl-2-oxo-oxazolidine-5-carboxamide

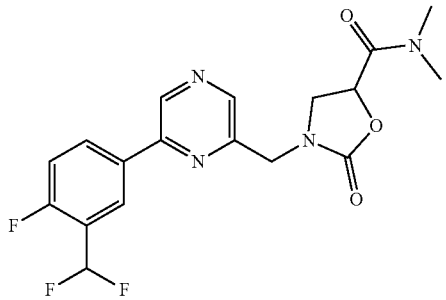 [SMILES: CN(C)C(=O)C1CN(Cc2cncc(-c3ccc(F)c(C(F)F)c3)n2)C(=O)O1]

Step A: 3-((6-(3-(Difluoromethyl)-4-fluorophenyl)pyrazin-2-yl)methyl)-2-oxooxazolidine-5-carboxylic acid. Prepared analogous to Example 55 (Steps A-B), using (R/S)-Benzyl 2-oxooxazolidine-5-carboxylate (Intermediate 5) and 2-(Chloromethyl)-6-(3-(difluoromethyl)-4-fluorophenyl)pyrazine (Intermediate 7). MS (ESI): mass calcd. for $C_{16}H_{12}F_3N_3O_4$, 367.1; m/z found, 368 [M+H]$^+$.

Step B: (R/S)-3-[[6-[3-(Difluoromethyl)-4-fluoro-phenyl]pyrazin-2-yl]methyl]-N,N-dimethyl-2-oxo-oxazolidine-5-carboxamide. To a solution of 3-((6-(3-(difluoromethyl)-4-fluorophenyl)pyrazin-2-yl)methyl)-2-oxooxazolidine-5-carboxylic acid (80 mg, 0.2 mmol, 1 equiv) in DMF (1 mL) was added HATU (124 mg, 0.3 mmol, 1.5 equiv), DIPEA (151 µL, 0.87 mmol, 4 equiv) and dimethylamine (218 µL, 0.43 mmol, 2.0 M in THF, 2 equiv), and the reaction mixture was stirred at rt for 16 h. The mixture was partitioned between a saturated aqueous solution of NaHCO$_3$ and AcOEt. The organic layer was separated and washed with brine, dried over MgSO$_4$, filtered, and concentrated under vacuum. The residue was purified by flash column chromatography (silica, gradient of DCM/MeOH (9:1) in DCM (0 to 19%). The material was further purified by reverse phase chromatography, Method E, to give the title compound (27 mg, 0.07 mmol, 31%). MS (ESI): mass calcd. for $C_{18}H_{17}F_3N_4O_3$, 394.1; m/z found, 395 [M+H]$^+$. $^1$H NMR (300 MHz, CDCl$_3$) δ 8.98 (s, 1H), 8.59 (s, 1H), 8.29 (s, 1H), 8.17 (s, 1H), 7.36-7.20 (m, 1H), 6.98 (t, J=54.8 Hz, 1H), 5.24-5.10 (m, 1H), 4.69 (s, 2H), 4.46-4.32 (m, 1H), 3.76 (t, J=8.7 Hz, 1H), 3.18 (s, 3H), 3.01 (s, 3H).

Example 66: (R/S)-3-[[6-[3-(Difluoromethoxy)-4-fluoro-phenyl]pyrazin-2-yl]methyl]-N,N-dimethyl-2-oxo-oxazolidine-5-carboxamide

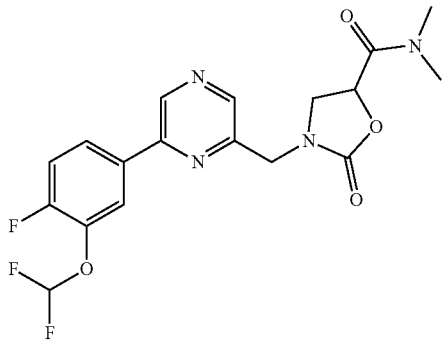 [SMILES: CN(C)C(=O)C1CN(Cc2cncc(-c3ccc(F)c(OC(F)F)c3)n2)C(=O)O1]

Prepared analogous to Example 65, using 2-(Chloromethyl)-6-(3-(difluoromethoxy)-4-fluorophenyl)pyrazine (Intermediate 8) in Step A. MS (ESI): mass calcd. for $C18H_{17}F_3N_4O_4$, 410.1; m/z found, 411 [M+H]$^+$. $^1$H NMR (300 MHz, CDCl$_3$) δ 8.94 (s, 1H), 8.57 (s, 1H), 8.00 (d, J=6.8 Hz, 1H), 7.86 (s, 1H), 7.32 (d, J=9.3 Hz, 1H), 6.72 (t, J=73.4 Hz, 1H), 5.21-5.11 (m, 1H), 4.68 (s, 2H), 4.47-4.35 (m, 1H), 3.76 (t, J=8.7 Hz, 1H), 3.17 (s, 3H), 3.01 (s, 3H).

Example 67: 6-[[6-[4-Chloro-3-(difluoromethoxy)phenyl]pyrazin-2-yl]methyl]-8-oxa-2,6-diazaspiro[3.4]octan-7-one

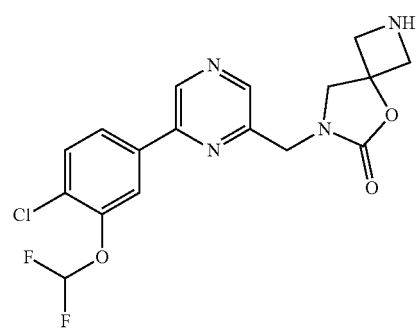 [SMILES: O=C1OC2(CNC2)CN1Cc1cncc(-c2ccc(Cl)c(OC(F)F)c2)n1]

Step A: Tert-butyl 7-((6-(4-chloro-3-(difluoromethoxy)phenyl)pyrazin-2-yl)methyl)-6-oxo-5-oxa-2,7-diazaspiro[3.4]octane-2-carboxylate. Prepared analogous to Example 3, using tert-Butyl 6-oxo-5-oxa-2,7-diazaspiro[3.4]octane-2-carboxylate (Intermediate 6) and 2-(4-Chloro-3-(difluoromethoxy)phenyl)-6-(chloromethyl)pyrazine (Intermediate 9). MS (ESI): mass calcd. for $C_{22}H_{23}ClF_2N_4O_5$, 496.1; m/z found, 497 [M+H]$^+$.

Step B: 6-[[6-[4-Chloro-3-(difluoromethoxy)phenyl]pyrazin-2-yl]methyl]-8-oxa-2,6-diazaspiro[3.4]octan-7-one. Trifluoroacetic acid (0.296 mL, 3.8 mmol, 20 equiv) was added portion-wise to a solution of tert-butyl 7-((6-(4-chloro-3-(difluoromethoxy)phenyl)pyrazin-2-yl)methyl)-6-oxo-5-oxa-2,7-diazaspiro[3.4]octane-2-carboxylate (120 mg, 0.19 mmol, 1 equiv) in DCM (1 mL) at 0° C., and the reaction mixture was stirred at rt for 2 h. Then, DCM and a saturated aqueous solution of Na$_2$CO$_3$ were added to the reaction mixture and the biphasic mixture was stirred. The organic layer was separated, dried with Na$_2$SO$_4$, filtered, and concentrated. The crude material was purified by flash column chromatography (silica; gradient of DCM/MeOH (10:1) in DCM 0/100 to 30/70) to yield the title compound (19 mg, 0.04 mmol, 23%). MS (ESI): mass calcd. for $C_{17}H_{15}ClF_2N_4O_3$, 396.1; m/z found, 397 [M+H]$^+$. $^1$H NMR (300 MHz, CDCl$_3$) δ 8.87 (s, 1H), 8.46 (s, 1H), 7.85 (s, 1H), 7.72 (d, J=8.1 Hz, 1H), 7.50 (d, J=8.3 Hz, 1H), 6.55 (t, J=73.1 Hz, 1H), 4.57 (s, 2H), 4.04 (d, J=8.9 Hz, 2H), 3.85 (s, 2H), 3.51 (d, J=8.9 Hz, 2H), 3.39 (s, 2H).

Example 68: 6-[[6-[4-Chloro-3-(difluoromethoxy)phenyl]pyrazin-2-yl]methyl]-2-methyl-8-oxa-2,6-diazaspiro[3.4]octan-7-one

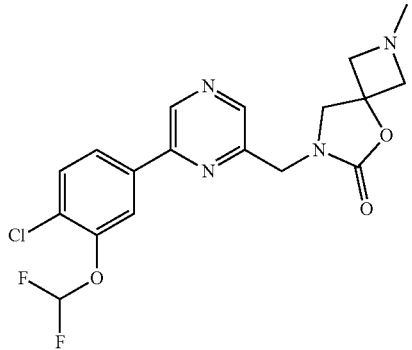 [SMILES: CN1CC2(C1)CN(Cc1cncc(-c3ccc(Cl)c(OC(F)F)c3)n1)C(=O)O2]

To a solution of 6-[[6-[4-Chloro-3-(difluoromethoxy)phenyl]pyrazin-2-yl]methyl]-8-oxa-2,6-diazaspiro[3.4]octan-7-one (Example 67) (145 mg, 0.37 mmol, 1 equiv) in DMF (3 mL) at 0° C. was added sodium hydride (15 mg, 0.4 mmol, 60% dispersion in mineral oil, 1.1 equiv), and the reaction mixture was stirred for 30 min. Then, methyl iodide (0.02 mL, 0.4 mmol, 1.1 equiv) was added dropwise at 0° C., and the reaction mixture was stirred at rt for 2 h. A saturated aqueous solution of NaHCO$_3$ was added dropwise and the reaction was diluted with AcOEt. The aqueous layer was further extracted with AcOEt. The combined organic layers were dried over MgSO$_4$, filtered and the solvents removed under vacuum to afford a white solid. This crude was purified by flash column chromatography (silica, DCM in MeOH (9:1)) to give the title compound (27 mg, 0.062 mmol, 17%). MS (ESI): mass calcd. for $C_{18}H_{17}ClF_2N_4O_3$, 410.1; m/z found, 411 [M+H]$^+$. $^1$H NMR (300 MHz, CDCl$_3$) δ 8.96 (s, 1H), 8.55 (s, 1H), 7.94 (s, 1H), 7.82 (dd, J=8.4, 2.0 Hz, 1H), 7.59 (d, J=8.4 Hz, 1H), 6.64 (t, J=73.1 Hz, 1H), 4.66 (s, 2H), 3.91 (s, 2H), 3.51 (dd, J=8.3, 6.4 Hz, 2H), 3.39 (dd, J=7.1, 2.0 Hz, 2H), 2.38 (s, 3H).

5.3. Biological Assays: Effect of Compounds of Formula (I) on Cloned Human GluN1/GluN2B Ion Channels Expressed in Mammalian Cells NMDA receptors are ion channels that are highly permeable to Ca$^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular Ca$^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM CaCl$_2$, 0.5 mM MgCl$_2$ (standard assay) or 1.5 mM MgCl$_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM CaCl$_2$, 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~EC$_{40}$ (standard assay) or EC$_{40}$ (HTS assay) is used to maximize the assay's signal window and ability to detect NMDA receptor antagonists and negative allosteric modulators. A saturating concentration (10 μM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

Results of the assay performed on the compounds of Examples 1 to 68 are shown in Table 4.

TABLE 4

| Example # | Compound Name | GluN2B IC$_{50}$ (nM) standard assay |
|---|---|---|
| 1 | 3-[[6-[3-(Difluoromethyl)-4-fluoro-phenyl]pyrazin-2-yl]methyl]oxazolidin-2-one; | 195 |
| 2 | 3-[[6-[3-(Difluoromethoxy)-4-fluoro-phenyl]pyrazin-2-yl]methyl]oxazolidin-2-one; | 73 |
| 3 | 5-[[6-[3-(Difluoromethyl)-4-fluoro-phenyl]pyrazin-2-yl]methyl]-7-oxa-5-azaspiro[2.4]heptan-6-one; | 13 |
| 4 | 3-[[6-[3-(Difluoromethyl)-4-fluoro-phenyl]pyrazin-2-yl]methyl]-5,5-dimethyl-oxazolidin-2-one; | 1360 |
| 5 | (5R)-3-[[6-[3-(Difluoromethyl)-4-fluoro-phenyl]pyrazin-2-yl]methyl]-5-methyl-oxazolidin-2-one; | 29 |
| 6 | (5S)-3-[[6-[3-(Difluoromethyl)-4-fluoro-phenyl]pyrazin-2-yl]methyl]-5-methyl-oxazolidin-2-one; | 60 |
| 7 | (4R)-3-[[6-[3-(Difluoromethyl)-4-fluoro-phenyl]pyrazin-2-yl]methyl]-4-methyl-oxazolidin-2-one; | 288 |
| 8 | (4S)-3-[[6-[3-(Difluoromethyl)-4-fluoro-phenyl]pyrazin-2-yl]methyl]-4-methyl-oxazolidin-2-one; | 872 |
| 9 | 3-[[6-[3-(Difluoromethyl)-4-fluoro-phenyl]pyrazin-2-yl]methyl]-1,3-oxazinan-2-one; | 65 |
| 10 | 5-[[6-[3-(Difluoromethyl)-4-fluoro-phenyl]-3-methyl-pyrazin-2-yl]methyl]-7-oxa-5-azaspiro[2.4]heptan-6-one; | 37 |
| 11 | (4R)-3-[[6-[3-(Difluoromethyl)-4-fluoro-phenyl]-3-methyl-pyrazin-2-yl]methyl]-4-methyl-oxazolidin-2-one; | 192 |

TABLE 4-continued

| Example # | Compound Name | GluN2B IC$_{50}$ (nM) standard assay |
|---|---|---|
| 12 | (4S)-3-[[6-[3-(Difluoromethyl)-4-fluoro-phenyl]-3-methyl-pyrazin-2-yl]methyl]-4-methyl-oxazolidin-2-one; | 605 |
| 13 | (5R)-3-[[6-[3-(Difluoromethyl)-4-fluoro-phenyl]-3-methyl-pyrazin-2-yl]methyl]-5-methyl-oxazolidin-2-one; | 45 |
| 14 | (5S)-3-[[6-[3-(Difluoromethyl)-4-fluoro-phenyl]-3-methyl-pyrazin-2-yl]methyl]-5-methyl-oxazolidin-2-one; | 50 |
| 15 | 3-[[6-[3-(Difluoromethyl)-4-fluoro-phenyl]-3-methyl-pyrazin-2-yl]methyl]-1,3-oxazinan-2-one; | 65 |
| 16 | 5-[[6-[3-(Difluoromethoxy)-4-fluoro-phenyl]pyrazin-2-yl]methyl]-7-oxa-5-azaspiro[2.4]heptan-6-one; | 19 |
| 17 | 3-[[6-[3-(Difluoromethoxy)-4-fluoro-phenyl]pyrazin-2-yl]methyl]-5,5-dimethyl-oxazolidin-2-one; | 1140 |
| 18 | (4R)-3-[[6-[3-(Difluoromethoxy)-4-fluoro-phenyl]pyrazin-2-yl]methyl]-4-methyl-oxazolidin-2-one; | 44 |
| 19 | (4S)-3-[[6-[3-(Difluoromethoxy)-4-fluoro-phenyl]pyrazin-2-yl]methyl]-4-methyl-oxazolidin-2-one; | 291 |
| 20 | (5R)-3-[[6-[3-(Difluoromethoxy)-4-fluoro-phenyl]pyrazin-2-yl]methyl]-5-methyl-oxazolidin-2-one; | 29 |
| 21 | (5S)-3-[[6-[3-(Difluoromethoxy)-4-fluoro-phenyl]pyrazin-2-yl]methyl]-5-methyl-oxazolidin-2-one; | 20 |
| 22 | 3-[[6-[3-(Difluoromethoxy)-4-fluoro-phenyl]pyrazin-2-yl]methyl]-1,3-oxazinan-2-one; | 17 |
| 23 | 5-[[6-[3-(Difluoromethoxy)-4-fluoro-phenyl]-3-methyl-pyrazin-2-yl]methyl]-7-oxa-5-azaspiro[2.4]heptan-6-one; | 66 |
| 24 | (4R)-3-[[6-[3-(Difluoromethoxy)-4-fluoro-phenyl]-3-methyl-pyrazin-2-yl]methyl]-4-methyl-oxazolidin-2-one; | 78 |
| 25 | (4S)-3-[[6-[3-(Difluoromethoxy)-4-fluoro-phenyl]-3-methyl-pyrazin-2-yl]methyl]-4-methyl-oxazolidin-2-one; | 388 |
| 26 | (5R)-3-[[6-[3-(Difluoromethoxy)-4-fluoro-phenyl]-3-methyl-pyrazin-2-yl]methyl]-5-methyl-oxazolidin-2-one; | 52 |
| 27 | (5S)-3-[[6-[3-(Difluoromethoxy)-4-fluoro-phenyl]-3-methyl-pyrazin-2-yl]methyl]-5-methyl-oxazolidin-2-one; | 48 |
| 28 | 3-[[6-[3-(Difluoromethoxy)-4-fluoro-phenyl]-3-methyl-pyrazin-2-yl]methyl]-1,3-oxazinan-2-one; | 39 |
| 29 | 5-[[6-[4-Chloro-3-(difluoromethoxy)phenyl]pyrazin-2-yl]methyl]-7-oxa-5-azaspiro[2.4]heptan-6-one; | 19 |
| 30 | 3-[[6-[4-Chloro-3-(difluoromethoxy)phenyl]pyrazin-2-yl]methyl]-5,5-dimethyl-oxazolidin-2-one; | 669 |
| 31 | (5R)-3-[[6-[4-Chloro-3-(difluoromethoxy)phenyl]pyrazin-2-yl]methyl]-5-methyl-oxazolidin-2-one; | 20 |
| 32 | (5S)-3-[[6-[4-Chloro-3-(difluoromethoxy)phenyl]pyrazin-2-yl]methyl]-5-methyl-oxazolidin-2-one; | 20 |
| 33 | (4R)-3-[[6-[4-Chloro-3-(difluoromethoxy)phenyl]pyrazin-2-yl]methyl]-4-methyl-oxazolidin-2-one; | 21 |
| 34 | (4S)-3-[[6-[4-Chloro-3-(difluoromethoxy)phenyl]pyrazin-2-yl]methyl]-4-methyl-oxazolidin-2-one; | 86 |
| 35 | 3-[[6-[4-Chloro-3-(difluoromethoxy)phenyl]pyrazin-2-yl]methyl]-1,3-oxazinan-2-one; | 13 |
| 36 | 5-[[6-[4-Chloro-3-(difluoromethoxy)phenyl]-3-methyl-pyrazin-2-yl]methyl]-7-oxa-5-azaspiro[2.4]heptan-6-one; | 113 |
| 37 | 3-[[6-[4-Chloro-3-(difluoromethoxy)phenyl]-3-methyl-pyrazin-2-yl]methyl]-1,3-oxazinan-2-one; | 18 |
| 38 | 5-[[6-[3-(1,1-Difluoroethyl)phenyl]pyrazin-2-yl]methyl]-7-oxa-5-azaspiro[2.4]heptan-6-one; | 17 |
| 39 | 3-[[6-[3-(1,1-Difluoroethyl)phenyl]pyrazin-2-yl]methyl]-5,5-dimethyl-oxazolidin-2-one; | 4510 |
| 40 | (5R)-3-[[6-[3-(1,1-Difluoroethyl)phenyl]pyrazin-2-yl]methyl]-5-methyl-oxazolidin-2-one; | 39 |
| 41 | (5S)-3-[[6-[3-(1,1-Difluoroethyl)phenyl]pyrazin-2-yl]methyl]-5-methyl-oxazolidin-2-one; | 167 |
| 42 | 3-[[6-[3-(1,1-Difluoroethyl)phenyl]pyrazin-2-yl]methyl]-1,3-oxazinan-2-one; | 105 |
| 43 | 5-[[6-[3-(1,1-Difluoroethyl)phenyl]-3-methyl-pyrazin-2-yl]methyl]-7-oxa-5-azaspiro[2.4]heptan-6-one; | 203 |
| 44 | 3-[[6-[3-(1,1-Difluoroethyl)phenyl]-3-methyl-pyrazin-2-yl]methyl]-5,5-dimethyl-oxazolidin-2-one; | >3000 |
| 45 | 3-[[6-[3-(1,1-Difluoroethyl)phenyl]-3-methyl-pyrazin-2-yl]methyl]-1,3-oxazinan-2-one; | 127 |
| 46 | (4R)-3-[[6-[3-(1,1-Difluoroethyl)-4-fluoro-phenyl]pyrazin-2-yl]methyl]-4-methyl-oxazolidin-2-one; | 166 |
| 47 | (4S)-3-[[6-[3-(1,1-Difluoroethyl)-4-fluoro-phenyl]pyrazin-2-yl]methyl]-4-methyl-oxazolidin-2-one; | 624 |

TABLE 4-continued

| Example # | Compound Name | GluN2B IC$_{50}$ (nM) standard assay |
|---|---|---|
| 48 | 6-[[6-[3-(1,1-Difluoroethyl)phenyl]pyrazin-2-yl]methyl]-8-oxa-6-azaspiro[2.5]octan-7-one; | 124 |
| 49 | 6-[[6-[3-(Difluoromethoxy)-4-fluoro-phenyl]pyrazin-2-yl]methyl]-8-oxa-6-azaspiro[2.5]octan-7-one; | 48 |
| 50 | 6-[[6-[4-Chloro-3-(difluoromethoxy)phenyl]pyrazin-2-yl]methyl]-8-oxa-6-azaspiro[2.5]octan-7-one; | 49 |
| 51 | 6-[[6-[4-Chloro-3-(difluoromethoxy)phenyl]-3-methyl-pyrazin-2-yl]methyl]-8-oxa-6-azaspiro[2.5]octan-7-one; | not tested |
| 52 | 6-[[6-[3-(Difluoromethyl)-4-fluoro-phenyl]pyrazin-2-yl]methyl]-8-oxa-6-azaspiro[2.5]octan-7-one; | 61 |
| 53 | 6-[[6-[3-(Difluoromethyl)-4-fluoro-phenyl]-3-methyl-pyrazin-2-yl]methyl]-8-oxa-6-azaspiro[2.5]octan-7-one; | 102 |
| 54 | 6-[[6-[3-(Difluoromethoxy)-4-fluoro-phenyl]-3-methyl-pyrazin-2-yl]methyl]-8-oxa-6-azaspiro[2.5]octan-7-one; | 74 |
| 55 | (R/S)-3-[[6-[4-Chloro-3-(difluoromethoxy)phenyl]pyrazin-2-yl]methyl]-N,N-dimethyl-2-oxo-oxazolidine-5-carboxamide; | 1392 |
| 56 | (R/S)-3-[[6-[4-Chloro-3-(difluoromethoxy)phenyl]pyrazin-2-yl]methyl]-N-methyl-2-oxo-oxazolidine-5-carboxamide; | 2050 |
| 57 | 5-(Azetidine-1-carbonyl)-3-[[6-[4-chloro-3-(difluoromethoxy)phenyl]pyrazin-2-yl]methyl]oxazolidin-2-one; | 2000 |
| 58 | (R/S)-5-(Azetidine-1-carbonyl)-3-[[6-[3-(difluoromethyl)-4-fluoro-phenyl]pyrazin-2-yl]methyl]oxazolidin-2-one; | >3000 |
| 59 | (R/S)-3-[[6-[3-(Difluoromethyl)-4-fluoro-phenyl]pyrazin-2-yl]methyl]-N-methyl-2-oxo-oxazolidine-5-carboxamide; | >3000 |
| 60 | (R/S)-3-[[6-[3-(Difluoromethoxy)-4-fluoro-phenyl]pyrazin-2-yl]methyl]-N-methyl-2-oxo-oxazolidine-5-carboxamide; | 5390 |
| 61 | (R/S)-5-(Azetidine-1-carbonyl)-3-[[6-[3-(difluoromethoxy)-4-fluoro-phenyl]pyrazin-2-yl]methyl]oxazolidin-2-one; | 5740 |
| 62 | (R/S)-3-[[6-[3-(1,1-Difluoroethyl)-4-fluoro-phenyl]pyrazin-2-yl]methyl]-N,N-dimethyl-2-oxo-oxazolidine-5-carboxamide; | 3680 |
| 63 | (R/S)-3-[[6-[3-(1,1-Difluoroethyl)-4-fluoro-phenyl]pyrazin-2-yl]methyl]-N-methyl-2-oxo-oxazolidine-5-carboxamide; | >3000 |
| 64 | (R/S)-5-(Azetidine-1-carbonyl)-3-[[6-[3-(1,1-difluoroethyl)-4-fluoro-phenyl]pyrazin-2-yl]methyl]oxazolidin-2-one; | >3000 |
| 65 | (R/S)-3-[[6-[3-(Difluoromethyl)-4-fluoro-phenyl]pyrazin-2-yl]methyl]-N,N-dimethyl-2-oxo-oxazolidine-5-carboxamide; | >3000 |
| 66 | (R/S)-3-[[6-[3-(Difluoromethoxy)-4-fluoro-phenyl]pyrazin-2-yl]methyl]-N,N-dimethyl-2-oxo-oxazolidine-5-carboxamide; | 141 |
| 67 | 64[6-[4-Chloro-3-(difluoromethoxy)phenyl]pyrazin-2-yl]methyl]-8-oxa-2,6-diazaspiro[3.4]octan-7-one; and | 530 |
| 68 | 64[6-[4-Chloro-3-(difluoromethoxy)phenyl]pyrazin-2-yl]methyl]-2-methyl-8-oxa-2,6-diazaspiro[3.4]octan-7-one. | 599 |

5.4. Liver Microsomal Stability Assay (Extraction Ratio)

Microsomal stability studies (see, Chrovian et al, "1H-Pyrrolo[3,2-b]pyridine GluN2B-Selective Negative Allosteric Modulators". ACS Med Chem Lett. 2019 Jan. 10; 10(3):261-266) were conducted on a Biomek® FX Robotic Liquid Handling Workstation (Beckman Coulter, Brea, Calif.), which consists of a 96-channel pipette head, a 12-position workstation deck, and a plate incubator. Test compounds (1 μM) were spiked in a reaction mix consisting of 100 mM potassium phosphate buffer (pH 7.4), 3 mM $MgCl_2$, and 0.5 mg/mL liver microsomes from mouse, rat, and human (BD Gentest). The reaction was brought to 37° C. and initiated by adding NADPH to a final concentration of 1 mM. After mixing on the platedeck, 50 μL aliquots were excised from the reaction plate at 0, 5, 10, 20, 40, and 60 min and quenched with four volumes of acetonitrile spiked with 500 μg/nL of the internal standard phenytoin. Quenched plates were centrifuged at 5700 rpm for 10 min at 4° C., and supernatant was diluted 1:3 in water before LC/MS/MS analysis. The compound half-lives were derived from plots of the ln of percent remaining compound over time to determine the intrinsic clearance. The predicted hepatic clearance was derived from the intrinsic clearance value using equations from the well-stirred model (Current Drug Metabolism, 2008, 9, 940-951), where no correction was made plasma protein binding and the blood to plasma concentration ratio was assumed to be one. The extraction ratio (ER) was calculated by dividing the predicted hepatic clearance by species blood flow (Q), where Q is 90, 55, and 21.7 mL/min/kg for mouse, rat and human, respectively.

Results of the assay performed on several compounds of the Examples are shown in Table 5.

TABLE 5

| Example # | Extraction Ratio @ 1 μM |
|---|---|
| 3 | 0.05 |
| 8 | 0.06 |
| 11 | 0.18 |
| 15 | 0.06 |
| 59 | 0.18 |

6. SPECIFIC EMBODIMENTS

The present disclosure is exemplified by the specific embodiments below.

1. A compound of Formula (I):

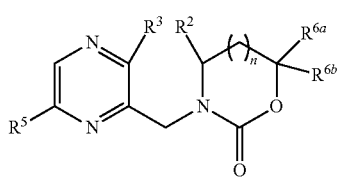
(I)

or a pharmaceutically acceptable salt, solvate, isotopic variant, or N-oxide thereof, wherein:

n is 0 or 1;
$R^2$ is H or alkyl;
$R^3$ is H or alkyl;
$R^5$ is aryl which is optionally substituted with one or two substituents each of which is independently halogen, haloalkyl, or O-haloalkyl; and
$R^{6a}$ and $R^{6b}$ are, each independent from the other, H or alkyl which is optionally substituted with (=O) and a heterocycloalkyl, —NHCH$_3$, or —N(CH$_3$)$_2$; or $R^{6a}$ and $R^{6b}$ together with the carbon atom to which they are attached form (i) a cycloalkyl ring or (ii) a heterocycloalkyl ring which is optionally substituted with alkyl.

2. The compound of embodiment 1, or a pharmaceutically acceptable salt, solvate, isotopic variant, or N-oxide thereof, having the structure of Formula (Ia):

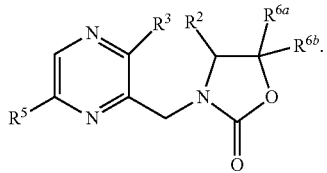
(Ia)

3. The compound of embodiment 1, or a pharmaceutically acceptable salt, solvate, isotopic variant, or N-oxide thereof, having the structure of Formula (Ib):

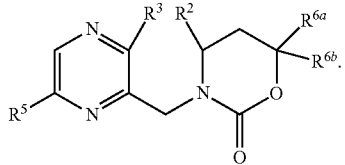
(Ib)

4. The compound of any one of embodiments 1 to 3, or a pharmaceutically acceptable salt, solvate, isotopic variant, or N-oxide thereof, wherein $R^2$ is H.

5. The compound of any one of embodiments 1 to 3, or a pharmaceutically acceptable salt, solvate, isotopic variant, or N-oxide thereof, wherein $R^2$ is alkyl.

6. The compound of any one of embodiments 1 to 3, or a pharmaceutically acceptable salt, solvate, isotopic variant, or N-oxide thereof, wherein $R^2$ is $C_1$-$C_6$alkyl.

7. The compound of any one of embodiments 1 to 3, or a pharmaceutically acceptable salt, solvate, isotopic variant, or N-oxide thereof, wherein $R^2$ is $C_1$-$C_3$alkyl.

8. The compound of any one of embodiments 1 to 3, or a pharmaceutically acceptable salt, solvate, isotopic variant, or N-oxide thereof, wherein $R^2$ is —CH$_3$.

9. The compound of any one of embodiments 5 to 8, or a pharmaceutically acceptable salt, solvate, isotopic variant, or N-oxide thereof, wherein the stereochemistry at the carbon to which $R^2$ is attached is (R).

10. The compound of any one of embodiments 5 to 8, or a pharmaceutically acceptable salt, solvate, isotopic variant, or N-oxide thereof, wherein the stereochemistry at the carbon to which $R^2$ is attached is (S).

11. The compound of any one of embodiments 1 to 10, or a pharmaceutically acceptable salt, solvate, isotopic variant, or N-oxide thereof, wherein $R^3$ is H or $C_1$-$C_6$alkyl.

12. The compound of any one of embodiments 1 to 10, or a pharmaceutically acceptable salt, solvate, isotopic variant, or N-oxide thereof, wherein $R^3$ is H or $C_1$-$C_3$alkyl.

13. The compound of any one of embodiments 1 to 10, or a pharmaceutically acceptable salt, solvate, isotopic variant, or N-oxide thereof, wherein $R^3$ is H.

14. The compound of any one of embodiments 1 to 10, or a pharmaceutically acceptable salt, solvate, isotopic variant, or N-oxide thereof, wherein $R^3$ is alkyl.

15. The compound of embodiment 14, or a pharmaceutically acceptable salt, solvate, isotopic variant, or N-oxide thereof, wherein $R^3$ is $C_1$-$C_6$alkyl.

16. The compound of embodiment 15, or a pharmaceutically acceptable salt, solvate, isotopic variant, or N-oxide thereof, wherein $R^3$ is $C_1$-$C_3$alkyl.

17. The compound of embodiment 16, or a pharmaceutically acceptable salt, solvate, isotopic variant, or N-oxide thereof, wherein $R^3$ is 01-$C_2$alkyl.

18. The compound of embodiment 17, or a pharmaceutically acceptable salt, solvate, isotopic variant, or N-oxide thereof, wherein $R^3$ is —CH$_3$.

19. The compound of any one of embodiments 1 to 18, or a pharmaceutically acceptable salt, solvate, isotopic variant, or N-oxide thereof, wherein $R^5$ is

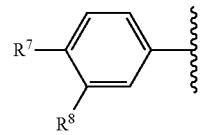

wherein $R^7$ is H or halogen, and $R^8$ is haloalkyl or O-haloalkyl.

20. The compound of embodiment 2, or a pharmaceutically acceptable salt, solvate, isotopic variant, or N-oxide thereof, having the structure of Formula (Ic):

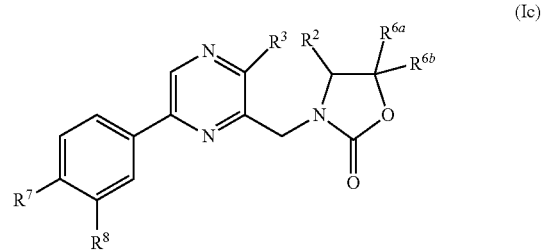
(Ic)

wherein $R^7$ is H or halogen, and $R^8$ is haloalkyl or O-haloalkyl.

21. The compound of embodiment 3, or a pharmaceutically acceptable salt, solvate, isotopic variant, or N-oxide thereof, having the structure of Formula (Id):

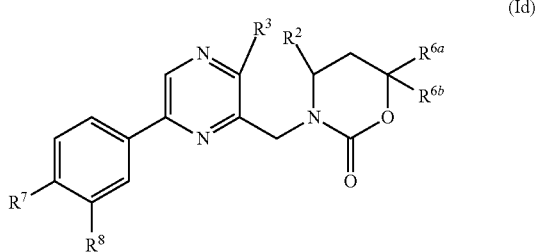

wherein $R^7$ is H or halogen, and $R^8$ is haloalkyl or O-haloalkyl.

22. The compound of any one of embodiments 19 to 21, or a pharmaceutically acceptable salt, solvate, isotopic variant, or N-oxide thereof, wherein $R^7$ is H or halogen, and $R^8$ is $C_1$-$C_6$haloalkyl or O— $C_1$-$C_6$haloalkyl.

23. The compound of any one of embodiments 19 to 21, or a pharmaceutically acceptable salt, solvate, isotopic variant, or N-oxide thereof, wherein $R^7$ is H or halogen, and $R^8$ is $C_1$-$C_3$haloalkyl or O— $C_1$-$C_3$haloalkyl.

24. The compound of any one of embodiments 19 to 23, or a pharmaceutically acceptable salt, solvate, isotopic variant, or N-oxide thereof, wherein $R^7$ is H.

25. The compound of any one of embodiments 19 to 23, or a pharmaceutically acceptable salt, solvate, isotopic variant, or N-oxide thereof, wherein $R^7$ is halogen.

26. The compound of embodiment 25, or a pharmaceutically acceptable salt, solvate, isotopic variant, or N-oxide thereof, wherein $R^7$ is F or Cl.

27. The compound of embodiment 26, or a pharmaceutically acceptable salt, solvate, isotopic variant, or N-oxide thereof, wherein $R^7$ is F.

28. The compound of embodiment 26, or a pharmaceutically acceptable salt, solvate, isotopic variant, or N-oxide thereof, wherein $R^7$ is Cl.

29. The compound of any one of embodiments 19 to 28, or a pharmaceutically acceptable salt, solvate, isotopic variant, or N-oxide thereof, wherein $R^8$ is haloalkyl.

30. The compound of embodiment 29, or a pharmaceutically acceptable salt, solvate, isotopic variant, or N-oxide thereof, wherein $R^8$ is $C_1$-$C_6$haloalkyl.

31. The compound of embodiment 30, or a pharmaceutically acceptable salt, solvate, isotopic variant, or N-oxide thereof, wherein $R^8$ is $C_1$-$C_3$haloalkyl.

32. The compound of embodiment 31, or a pharmaceutically acceptable salt, solvate, isotopic variant, or N-oxide thereof, wherein $R^8$ is $C_1$-$C_2$haloalkyl.

33. The compound of embodiment 32, or a pharmaceutically acceptable salt, solvate, isotopic variant, or N-oxide thereof, wherein $R^8$ is —$CHF_2$.

34. The compound of embodiment 32, or a pharmaceutically acceptable salt, solvate, isotopic variant, or N-oxide thereof, wherein $R^8$ is —$CF_2CH_3$.

35. The compound of any one of embodiments 19 to 28, or a pharmaceutically acceptable salt, solvate, isotopic variant, or N-oxide thereof, wherein $R^8$ is O-haloalkyl.

36. The compound of embodiment 35, or a pharmaceutically acceptable salt, solvate, isotopic variant, or N-oxide thereof, wherein $R^8$ is O—$C_1$-$C_6$haloalkyl.

37. The compound of embodiment 36, or a pharmaceutically acceptable salt, solvate, isotopic variant, or N-oxide thereof, wherein $R^8$ is O—$C_1$-$C_3$haloalkyl.

38. The compound of embodiment 37, or a pharmaceutically acceptable salt, solvate, isotopic variant, or N-oxide thereof, wherein $R^7$ is O—$C_1$-$C_2$haloalkyl.

39. The compound of embodiment 38, or a pharmaceutically acceptable salt, solvate, isotopic variant, or N-oxide thereof, wherein $R^7$ is —$OCHF_2$.

40. The compound of any one of embodiments 1 to 19, or a pharmaceutically acceptable salt, solvate, isotopic variant, or N-oxide thereof, wherein $R^5$ is:

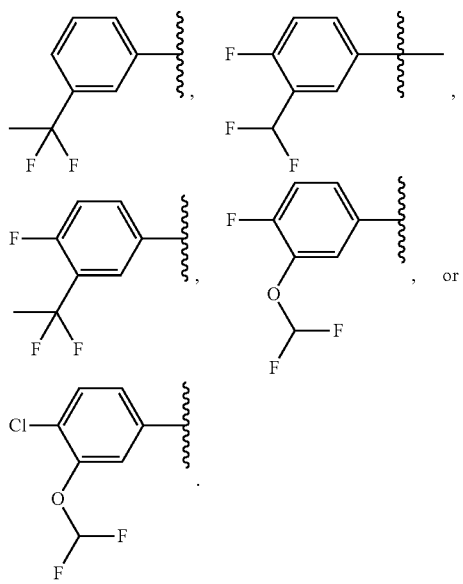

41. The compound of embodiment 40, or a pharmaceutically acceptable salt, solvate, isotopic variant, or N-oxide thereof, wherein $R^5$ is

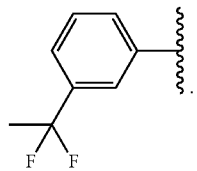

42. The compound of embodiment 40, or a pharmaceutically acceptable salt, solvate, isotopic variant, or N-oxide thereof, wherein $R^5$ is

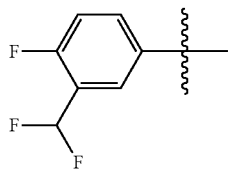

43. The compound of embodiment 40, or a pharmaceutically acceptable salt, solvate, isotopic variant, or N-oxide thereof, wherein $R^5$ is

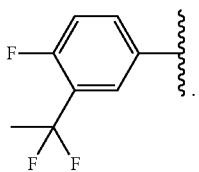

44. The compound of embodiment 40, or a pharmaceutically acceptable salt, solvate, isotopic variant, or N-oxide thereof, wherein $R^5$ is

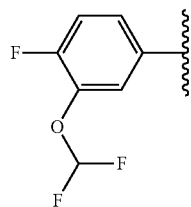

45. The compound of embodiment 40, or a pharmaceutically acceptable salt, solvate, isotopic variant, or N-oxide thereof, wherein $R^5$ is

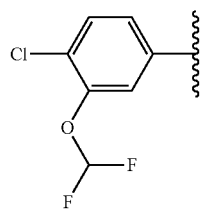

46. The compound of any one of embodiments 1 to 45, or a pharmaceutically acceptable salt, solvate, isotopic variant, or N-oxide thereof, wherein $R^{6a}$ and $R^{6b}$ are, each independent from the other, H or $C_1$-$C_6$alkyl which is optionally substituted with (=O) and a 4 to 6 membered heterocycloalkyl, —$NHCH_3$, or —$N(CH_3)_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_6$alkyl.

47. The compound of any one of embodiments 1 to 45, or a pharmaceutically acceptable salt, solvate, isotopic variant, or N-oxide thereof, wherein $R^{6a}$ and $R^{6b}$ are, each independent from the other, H or $C_1$-$C_3$alkyl which is optionally substituted with (=O) and a 4 to 6 membered heterocycloalkyl, —$NHCH_3$, or —$N(CH_3)_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_3$alkyl.

48. The compound of any one of embodiments 1 to 45, or a pharmaceutically acceptable salt, solvate, isotopic variant, or N-oxide thereof, wherein $R^{6a}$ and $R^{6b}$ are both H.

49. The compound of any one of embodiments 1 to 45, or a pharmaceutically acceptable salt, solvate, isotopic variant, or N-oxide thereof, wherein one of $R^{6a}$ and $R^{6b}$ is H and the other is alkyl which is optionally substituted with (=O) and a heterocycloalkyl, —$NHCH_3$, or —$N(CH_3)_2$; or $R^{6a}$ and $R^{6b}$ together with the carbon atom to which they are attached form (i) a cycloalkyl ring or (ii) a heterocycloalkyl ring which is optionally substituted with alkyl.

50. The compound of embodiment 49, or a pharmaceutically acceptable salt, solvate, isotopic variant, or N-oxide thereof, wherein one of $R^{6a}$ and $R^{6b}$ is H and the other is $C_1$-$C_6$alkyl which is optionally substituted with (=O) and a 4 to 6 membered heterocycloalkyl, —$NHCH_3$, or —$N(CH_3)_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_6$alkyl.

51. The compound of embodiment 49, or a pharmaceutically acceptable salt, solvate, isotopic variant, or N-oxide thereof, wherein one of $R^{6a}$ and $R^{6b}$ is H and the other is $C_1$-$C_3$alkyl which is optionally substituted with (=O) and a 4 to 6 membered heterocycloalkyl, —$NHCH_3$, or —$N(CH_3)_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_3$alkyl.

52. The compound of embodiment 51, or a pharmaceutically acceptable salt, solvate, isotopic variant, or N-oxide thereof, wherein one of $R^{6a}$ and $R^{6b}$ is H and the other is $C_1$-$C_3$alkyl which is optionally substituted with (=O) and a 4 to 6 membered heterocycloalkyl, —$NHCH_3$, or —$N(CH_3)_2$.

53. The compound of embodiment 52, or a pharmaceutically acceptable salt, solvate, isotopic variant, or N-oxide thereof, wherein one of $R^{6a}$ and $R^{6b}$ is H and the other is $C_1$-$C_3$alkyl.

54. The compound of embodiment 53, or a pharmaceutically acceptable salt, solvate, isotopic variant, or N-oxide thereof, wherein one of $R^{6a}$ and $R^{6b}$ is H and the other is —$CH_3$.

55. The compound of embodiment 51, or a pharmaceutically acceptable salt, solvate, isotopic variant, or N-oxide thereof, wherein one of $R^{6a}$ and $R^{6b}$ is H and the other is $C_1$-$C_3$alkyl which is substituted with (=O) and a 4 to 6 membered heterocycloalkyl, —$NHCH_3$, or —$N(CH_3)_2$.

56. The compound of embodiment 55, or a pharmaceutically acceptable salt, solvate, isotopic variant, or N-oxide thereof, wherein one of $R^{6a}$ and $R^{6b}$ is H and the other is

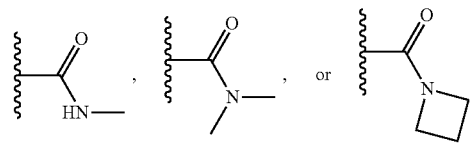

57. The compound of embodiment 56, or a pharmaceutically acceptable salt, solvate, isotopic variant, or N-oxide thereof, wherein one of $R^{6a}$ and $R^{6b}$ is H and the other is

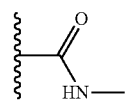

58. The compound of embodiment 56, or a pharmaceutically acceptable salt, solvate, isotopic variant, or N-oxide thereof, wherein one of $R^{6a}$ and $R^{6b}$ is

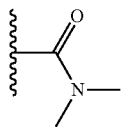

59. The compound of embodiment 56, or a pharmaceutically acceptable salt, solvate, isotopic variant, or N-oxide thereof, wherein one of $R^{6a}$ and $R^{6b}$ is H and the other is

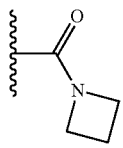

60. The compound of any one of embodiments 49 to 59, or a pharmaceutically acceptable salt, solvate, isotopic variant, or N-oxide thereof, wherein the stereochemistry at the carbon to which $R^{6a}$ and $R^{6b}$ are attached is (R).

61. The compound of any one of embodiments 49 to 59, or a pharmaceutically acceptable salt, solvate, isotopic variant, or N-oxide thereof, wherein the stereochemistry at the carbon to which $R^{6a}$ and $R^{6b}$ are attached is (S).

62. The compound of any one of embodiments 1 to 45, or a pharmaceutically acceptable salt, solvate, isotopic variant, or N-oxide thereof, wherein $R^{6a}$ and $R^{6b}$ are both alkyl.

63. The compound of embodiment 62, or a pharmaceutically acceptable salt, solvate, isotopic variant, or N-oxide thereof, wherein $R^{6a}$ and $R^{6b}$ are both $C_1$-$C_6$alkyl.

64. The compound of embodiment 63, or a pharmaceutically acceptable salt, solvate, isotopic variant, or N-oxide thereof, wherein $R^{6a}$ and $R^{6b}$ are both $C_1$-$C_2$alkyl.

65. The compound of embodiment 64, or a pharmaceutically acceptable salt, solvate, isotopic variant, or N-oxide thereof, wherein $R^{6a}$ and $R^{6b}$ are both —$CH_3$.

66. The compound of any one of embodiments 1 to 45, or a pharmaceutically acceptable salt, solvate, isotopic variant, or N-oxide thereof, wherein $R^{6a}$ and $R^{6b}$ together with the carbon atom to which they are attached form a cycloalkyl ring or a heterocycloalkyl ring which is optionally substituted with alkyl.

67. The compound of embodiment 66, or a pharmaceutically acceptable salt, solvate, isotopic variant, or N-oxide thereof, wherein $R^{6a}$ and $R^{6b}$ together with the carbon atom to which they are attached form a $C_3$-$C_6$cycloalkyl ring or a 4 to 6 membered heterocycloalkyl ring which is optionally substituted with $C_1$-$C_6$alkyl.

68. The compound of embodiment 66, or a pharmaceutically acceptable salt, solvate, isotopic variant, or N-oxide thereof, wherein $R^{6a}$ and $R^{6b}$ together with the carbon atom to which they are attached form a cycloalkyl ring 69. The compound of embodiment 68, or a pharmaceutically acceptable salt, solvate, isotopic variant, or N-oxide thereof, wherein $R^{6a}$ and $R^{6b}$ together with the carbon atom to which they are attached form a $C_3$-$C_6$cycloalkyl ring.

70. The compound of embodiment 69, or a pharmaceutically acceptable salt, solvate, isotopic variant, or N-oxide thereof, wherein $R^{6a}$ and $R^{6b}$ together with the carbon atom to which they are attached form a cyclopropyl ring.

71. The compound of embodiment 66, or a pharmaceutically acceptable salt, solvate, isotopic variant, or N-oxide thereof, wherein $R^{6a}$ and $R^{6b}$ together with the carbon atom to which they are attached form a heterocycloalkyl ring which is optionally substituted with alkyl.

72. The compound of embodiment 71, or a pharmaceutically acceptable salt, solvate, isotopic variant, or N-oxide thereof, wherein $R^{6a}$ and $R^{6b}$ together with the carbon atom to which they are attached form a 4 to 6 membered heterocycloalkyl ring which is optionally substituted with $C_1$-$C_6$alkyl.

73. The compound of embodiment 72, or a pharmaceutically acceptable salt, solvate, isotopic variant, or N-oxide thereof, wherein $R^{6a}$ and $R^{6b}$ together with the carbon atom to which they are attached form a 4 to 6 membered heterocycloalkyl ring which is optionally substituted with $C_1$-$C_3$alkyl.

74. The compound of embodiment 73, or a pharmaceutically acceptable salt, solvate, isotopic variant, or N-oxide thereof, wherein $R^{6a}$ and $R^{6b}$ together with the carbon atom to which they are attached form a azetidinyl ring which is optionally substituted with $C_1$-$C_3$alkyl.

75. The compound of embodiment 74, or a pharmaceutically acceptable salt, solvate, isotopic variant, or N-oxide thereof, wherein $R^{6a}$ and $R^{6b}$ together with the carbon atom to which they are attached is:

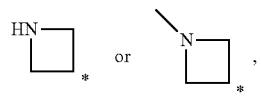

wherein * denotes the point of attachment of the ring to the remainder of the molecule.

76. The compound of embodiment 75, or a pharmaceutically acceptable salt, solvate, isotopic variant, or N-oxide thereof, wherein $R^{6a}$ and $R^{6b}$ together with the carbon atom to which they are attached is

77. The compound of embodiment 75, or a pharmaceutically acceptable salt, solvate, isotopic variant, or N-oxide thereof, wherein $R^{6a}$ and $R^{6b}$ together with the carbon atom to which they are attached is

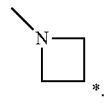

78. A compound, or a pharmaceutically acceptable salt, solvate, isotopic variant, or N-oxide thereof, wherein the compound is 3-[[6-[3-(Difluoromethyl)-4-fluoro-phenyl]pyrazin-2-yl]methyl]oxazolidin-2-one;

3-[[6-[3-(Difluoromethoxy)-4-fluoro-phenyl]pyrazin-2-yl]methyl]oxazolidin-2-one;

5-[[6-[3-(Difluoromethyl)-4-fluoro-phenyl]pyrazin-2-yl]methyl]-7-oxa-5-azaspiro[2.4]heptan-6-one;

3-[[6-[3-(Difluoromethyl)-4-fluoro-phenyl]pyrazin-2-yl]methyl]-5,5-dimethyl-oxazolidin-2-one;

(5R)-3-[[6-[3-(Difluoromethyl)-4-fluoro-phenyl]pyrazin-2-yl]methyl]-5-methyl-oxazolidin-2-one;

(5S)-3-[[6-[3-(Difluoromethyl)-4-fluoro-phenyl]pyrazin-2-yl]methyl]-5-methyl-oxazolidin-2-one;
(4R)-3-[[6-[3-(Difluoromethyl)-4-fluoro-phenyl]pyrazin-2-yl]methyl]-4-methyl-oxazolidin-2-one;
(4S)-3-[[6-[3-(Difluoromethyl)-4-fluoro-phenyl]pyrazin-2-yl]methyl]-4-methyl-oxazolidin-2-one;
3-[[6-[3-(Difluoromethyl)-4-fluoro-phenyl]pyrazin-2-yl]methyl]-1,3-oxazinan-2-one;
5-[[6-[3-(Difluoromethyl)-4-fluoro-phenyl]-3-methyl-pyrazin-2-yl]methyl]-7-oxa-5-azaspiro[2.4]heptan-6-one;
(4R)-3-[[6-[3-(Difluoromethyl)-4-fluoro-phenyl]-3-methyl-pyrazin-2-yl]methyl]-4-methyl-oxazolidin-2-one;
(4S)-3-[[6-[3-(Difluoromethyl)-4-fluoro-phenyl]-3-methyl-pyrazin-2-yl]methyl]-4-methyl-oxazolidin-2-one;
(5R)-3-[[6-[3-(Difluoromethyl)-4-fluoro-phenyl]-3-methyl-pyrazin-2-yl]methyl]-5-methyl-oxazolidin-2-one;
(5S)-3-[[6-[3-(Difluoromethyl)-4-fluoro-phenyl]-3-methyl-pyrazin-2-yl]methyl]-5-methyl-oxazolidin-2-one;
3-[[6-[3-(Difluoromethyl)-4-fluoro-phenyl]-3-methyl-pyrazin-2-yl]methyl]-1,3-oxazinan-2-one;
5-[[6-[3-(Difluoromethoxy)-4-fluoro-phenyl]pyrazin-2-yl]methyl]-7-oxa-5-azaspiro[2.4]heptan-6-one;
3-[[6-[3-(Difluoromethoxy)-4-fluoro-phenyl]pyrazin-2-yl]methyl]-5,5-dimethyl-oxazolidin-2-one;
(4R)-3-[[6-[3-(Difluoromethoxy)-4-fluoro-phenyl]pyrazin-2-yl]methyl]-4-methyl-oxazolidin-2-one;
(4S)-3-[[6-[3-(Difluoromethoxy)-4-fluoro-phenyl]pyrazin-2-yl]methyl]-4-methyl-oxazolidin-2-one;
(5R)-3-[[6-[3-(Difluoromethoxy)-4-fluoro-phenyl]pyrazin-2-yl]methyl]-5-methyl-oxazolidin-2-one;
(5S)-3-[[6-[3-(Difluoromethoxy)-4-fluoro-phenyl]pyrazin-2-yl]methyl]-5-methyl-oxazolidin-2-one;
3-[[6-[3-(Difluoromethoxy)-4-fluoro-phenyl]pyrazin-2-yl]methyl]-1,3-oxazinan-2-one;
5-[[6-[3-(Difluoromethoxy)-4-fluoro-phenyl]-3-methyl-pyrazin-2-yl]methyl]-7-oxa-5-azaspiro[2.4]heptan-6-one;
(4R)-3-[[6-[3-(Difluoromethoxy)-4-fluoro-phenyl]-3-methyl-pyrazin-2-yl]methyl]-4-methyl-oxazolidin-2-one;
(4S)-3-[[6-[3-(Difluoromethoxy)-4-fluoro-phenyl]-3-methyl-pyrazin-2-yl]methyl]-4-methyl-oxazolidin-2-one;
(5R)-3-[[6-[3-(Difluoromethoxy)-4-fluoro-phenyl]-3-methyl-pyrazin-2-yl]methyl]-5-methyl-oxazolidin-2-one;
(5S)-3-[[6-[3-(Difluoromethoxy)-4-fluoro-phenyl]-3-methyl-pyrazin-2-yl]methyl]-5-methyl-oxazolidin-2-one;
3-[[6-[3-(Difluoromethoxy)-4-fluoro-phenyl]-3-methyl-pyrazin-2-yl]methyl]-1,3-oxazinan-2-one;
5-[[6-[4-Chloro-3-(difluoromethoxy)phenyl]pyrazin-2-yl]methyl]-7-oxa-5-azaspiro[2.4]heptan-6-one;
3-[[6-[4-Chloro-3-(difluoromethoxy)phenyl]pyrazin-2-yl]methyl]-5,5-dimethyl-oxazolidin-2-one;
(5R)-3-[[6-[4-Chloro-3-(difluoromethoxy)phenyl]pyrazin-2-yl]methyl]-5-methyl-oxazolidin-2-one;
(5S)-3-[[6-[4-Chloro-3-(difluoromethoxy)phenyl]pyrazin-2-yl]methyl]-5-methyl-oxazolidin-2-one;
(4R)-3-[[6-[4-Chloro-3-(difluoromethoxy)phenyl]pyrazin-2-yl]methyl]-4-methyl-oxazolidin-2-one;
(4S)-3-[[6-[4-Chloro-3-(difluoromethoxy)phenyl]pyrazin-2-yl]methyl]-4-methyl-oxazolidin-2-one;
3-[[6-[4-Chloro-3-(difluoromethoxy)phenyl]pyrazin-2-yl]methyl]-1,3-oxazinan-2-one;
5-[[6-[4-Chloro-3-(difluoromethoxy)phenyl]-3-methyl-pyrazin-2-yl]methyl]-7-oxa-5-azaspiro[2.4]heptan-6-one;
3-[[6-[4-Chloro-3-(difluoromethoxy)phenyl]-3-methyl-pyrazin-2-yl]methyl]-1,3-oxazinan-2-one;
5-[[6-[3-(1,1-Difluoroethyl)phenyl]pyrazin-2-yl]methyl]-7-oxa-5-azaspiro[2.4]heptan-6-one;
3-[[6-[3-(1,1-Difluoroethyl)phenyl]pyrazin-2-yl]methyl]-5,5-dimethyl-oxazolidin-2-one;
(5R)-3-[[6-[3-(1,1-Difluoroethyl)phenyl]pyrazin-2-yl]methyl]-5-methyl-oxazolidin-2-one;
(5S)-3-[[6-[3-(1,1-Difluoroethyl)phenyl]pyrazin-2-yl]methyl]-5-methyl-oxazolidin-2-one;
3-[[6-[3-(1,1-Difluoroethyl)phenyl]pyrazin-2-yl]methyl]-1,3-oxazinan-2-one;
5-[[6-[3-(1,1-Difluoroethyl)phenyl]-3-methyl-pyrazin-2-yl]methyl]-7-oxa-5-azaspiro[2.4]heptan-6-one;
3-[[6-[3-(1,1-Difluoroethyl)phenyl]-3-methyl-pyrazin-2-yl]methyl]-5,5-dimethyl-oxazolidin-2-one;
3-[[6-[3-(1,1-Difluoroethyl)phenyl]-3-methyl-pyrazin-2-yl]methyl]-1,3-oxazinan-2-one;
(4R)-3-[[6-[3-(1,1-Difluoroethyl)-4-fluoro-phenyl]pyrazin-2-yl]methyl]-4-methyl-oxazolidin-2-one;
(4S)-3-[[6-[3-(1,1-Difluoroethyl)-4-fluoro-phenyl]pyrazin-2-yl]methyl]-4-methyl-oxazolidin-2-one;
6-[[6-[3-(1,1-Difluoroethyl)phenyl]pyrazin-2-yl]methyl]-8-oxa-6-azaspiro[2.5]octan-7-one;
6-[[6-[3-(Difluoromethoxy)-4-fluoro-phenyl]pyrazin-2-yl]methyl]-8-oxa-6-azaspiro[2.5]octan-7-one;
6-[[6-[4-Chloro-3-(difluoromethoxy)phenyl]pyrazin-2-yl]methyl]-8-oxa-6-azaspiro[2.5]octan-7-one;
6-[[6-[4-Chloro-3-(difluoromethoxy)phenyl]-3-methyl-pyrazin-2-yl]methyl]-8-oxa-6-azaspiro[2.5]octan-7-one;
6-[[6-[3-(Difluoromethyl)-4-fluoro-phenyl]pyrazin-2-yl]methyl]-8-oxa-6-azaspiro[2.5]octan-7-one;
6-[[6-[3-(Difluoromethyl)-4-fluoro-phenyl]-3-methyl-pyrazin-2-yl]methyl]-8-oxa-6-azaspiro[2.5]octan-7-one;
6-[[6-[3-(Difluoromethoxy)-4-fluoro-phenyl]-3-methyl-pyrazin-2-yl]methyl]-8-oxa-6-azaspiro[2.5]octan-7-one;
(R/S)-3-[[6-[4-Chloro-3-(difluoromethoxy)phenyl]pyrazin-2-yl]methyl]-N,N-dimethyl-2-oxo-oxazolidine-5-carboxamide;
(R/S)-3-[[6-[4-Chloro-3-(difluoromethoxy)phenyl]pyrazin-2-yl]methyl]-N-methyl-2-oxo-oxazolidine-5-carboxamide;
5-(Azetidine-1-carbonyl)-3-[[6-[4-chloro-3-(difluoromethoxy)phenyl]pyrazin-2-yl]methyl]oxazolidin-2-one;
(R/S)-5-(Azetidine-1-carbonyl)-3-[[6-[3-(difluoromethyl)-4-fluoro-phenyl]pyrazin-2-yl]methyl]oxazolidin-2-one;
(R/S)-3-[[6-[3-(Difluoromethyl)-4-fluoro-phenyl]pyrazin-2-yl]methyl]-N-methyl-2-oxo-oxazolidine-5-carboxamide;
(R/S)-3-[[6-[3-(Difluoromethoxy)-4-fluoro-phenyl]pyrazin-2-yl]methyl]-N-methyl-2-oxo-oxazolidine-5-carboxamide;
(R/S)-5-(Azetidine-1-carbonyl)-3-[[6-[3-(difluoromethoxy)-4-fluoro-phenyl]pyrazin-2-yl]methyl]oxazolidin-2-one;
(R/S)-3-[[6-[3-(1,1-Difluoroethyl)-4-fluoro-phenyl]pyrazin-2-yl]methyl]-N,N-dimethyl-2-oxo-oxazolidine-5-carboxamide;
(R/S)-3-[[6-[3-(1,1-Difluoroethyl)-4-fluoro-phenyl]pyrazin-2-yl]methyl]-N-methyl-2-oxo-oxazolidine-5-carboxamide;
(R/S)-5-(Azetidine-1-carbonyl)-3-[[6-[3-(1,1-difluoroethyl)-4-fluoro-phenyl]pyrazin-2-yl]methyl]oxazolidin-2-one;
(R/S)-3-[[6-[3-(Difluoromethyl)-4-fluoro-phenyl]pyrazin-2-yl]methyl]-N,N-dimethyl-2-oxo-oxazolidine-5-carboxamide;
(R/S)-3-[[6-[3-(Difluoromethoxy)-4-fluoro-phenyl]pyrazin-2-yl]methyl]-N,N-dimethyl-2-oxo-oxazolidine-5-carboxamide;

6-[[6-[4-Chloro-3-(difluoromethoxy)phenyl]pyrazin-2-yl]methyl]-8-oxa-2,6-diazaspiro[3.4]octan-7-one; or 6-[[6-[4-Chloro-3-(difluoromethoxy)phenyl]pyrazin-2-yl]methyl]-2-methyl-8-oxa-2,6-diazaspiro[3.4]octan-7-one.

79. A compound, or a pharmaceutically acceptable salt, solvate, isotopic variant, or N-oxide thereof, wherein the compound is 5-[[6-[3-(Difluoromethyl)-4-fluoro-phenyl]pyrazin-2-yl]methyl]-7-oxa-5-azaspiro[2.4]heptan-6-one;

3-[[6-[3-(Difluoromethoxy)-4-fluoro-phenyl]pyrazin-2-yl]methyl]-1,3-oxazinan-2-one;

5-[[6-[4-Chloro-3-(difluoromethoxy)phenyl]pyrazin-2-yl]methyl]-7-oxa-5-azaspiro[2.4]heptan-6-one;

3-[[6-[4-Chloro-3-(difluoromethoxy)phenyl]pyrazin-2-yl]methyl]-1,3-oxazinan-2-one; or 3-[[6-[3-(Difluoromethoxy)-4-fluoro-phenyl]-3-methyl-pyrazin-2-yl]methyl]-1,3-oxazinan-2-one.

80. The compound of any one of embodiments 1 to 79, or a pharmaceutically acceptable salt or solvate thereof.

81. The compound of any one of embodiments 1 to 79, or a pharmaceutically acceptable salt or N-oxide thereof.

82. The compound of any one of embodiments 1 to 79, or a pharmaceutically acceptable salt thereof.

83. The compound of any one of embodiments 1 to 79.

84. A pharmaceutically acceptable salt of the compound of any one of embodiments 1 to 79.

85. A pharmaceutical composition comprising the compound of any one of embodiments 1 to 79, or a pharmaceutically acceptable salt, solvate, isotopic variant, or N-oxide thereof, and a pharmaceutically acceptable excipient.

86. A pharmaceutical composition comprising the compound of any one of embodiments 1 to 79, or a pharmaceutically acceptable salt or solvate thereof, and a pharmaceutically acceptable excipient.

87. A pharmaceutical composition comprising the compound of any one of embodiments 1 to 79, or a pharmaceutically acceptable salt or N-oxide thereof, and a pharmaceutically acceptable excipient.

88. A pharmaceutical composition comprising the compound of any one of embodiments 1 to 79, or a pharmaceutically acceptable salt thereof, and a pharmaceutically acceptable excipient.

89. A pharmaceutical composition comprising the compound of any one of embodiments 1 to 79 and a pharmaceutically acceptable excipient.

90. A pharmaceutical composition comprising a pharmaceutically acceptable salt of the compound of any one of embodiments 1 to 79, and a pharmaceutically acceptable excipient.

91. A unit dosage form comprising a therapeutically effective amount of the pharmaceutical composition of any one of embodiments 85 to 90.

92. A method of treating a subject suffering from or diagnosed with a disease, disorder, or medical condition mediated by GluN2B receptor activity, comprising administering to the subject a therapeutically effective amount of the compound of any one of embodiments 1 to 79, or a pharmaceutically acceptable salt, solvate, isotopic variant, or N-oxide thereof.

93. A method of treating a subject suffering from or diagnosed with a disease, disorder, or medical condition mediated by GluN2B receptor activity, comprising administering to the subject a therapeutically effective amount of the compound of any one of embodiments 1 to 79, or a pharmaceutically acceptable salt, or solvate thereof.

94. A method of treating a subject suffering from or diagnosed with a disease, disorder, or medical condition mediated by GluN2B receptor activity, comprising administering to the subject a therapeutically effective amount of the compound of any one of embodiments 1 to 79, or a pharmaceutically acceptable salt or N-oxide thereof.

95. A method of treating a subject suffering from or diagnosed with a disease, disorder, or medical condition mediated by GluN2B receptor activity, comprising administering to the subject a therapeutically effective amount of the compound of any one of embodiments 1 to 79, or a pharmaceutically acceptable salt thereof.

96. A method of treating a subject suffering from or diagnosed with a disease, disorder, or medical condition mediated by GluN2B receptor activity, comprising administering to the subject a therapeutically effective amount of the pharmaceutical composition of any one of embodiments 85 to 90 or the unit dosage form of embodiment 91.

97. The method of any one of embodiments 92 to 96, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

98. The method of embodiment 97, wherein the disease, disorder or medical condition mediated by GluN2B receptor activity comprises bipolar disorder, a mood disorder, treatment resistant depression, major depressive disorder, or epilepsy.

99. The method of embodiment 98, wherein the disease, disorder or medical condition mediated by GluN2B receptor activity comprises bipolar disorder.

100. The method of embodiment 98, wherein the disease, disorder or medical condition mediated by GluN2B receptor activity comprises a mood disorder.

101. The method of embodiment 98, wherein the disease, disorder or medical condition mediated by GluN2B receptor activity comprises treatment resistant depression.

102. The method of embodiment 98, wherein the disease, disorder or medical condition mediated by GluN2B receptor activity comprises major depressive disorder.

103. The method of embodiment 98, wherein the disease, disorder or medical condition mediated by GluN2B receptor activity comprises epilepsy.

7. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A compound of Formula (I):

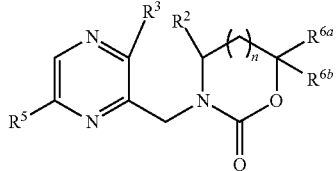

(I)

or a pharmaceutically acceptable salt, solvate, isotopic variant, or N-oxide thereof, wherein:

n is 0 or 1;

$R^2$ is H or $C_1$-$C_6$alkyl;

$R^3$ is H or $C_1$-$C_6$alkyl;

$R^5$ is aryl which is optionally substituted with one or two substituents each of which is independently halogen, $C_1$-$C_6$haloalkyl, or O—$C_1$-$C_6$haloalkyl; and $R^{6a}$ and $R^{6b}$ are, each independent from the other, H or $C_1$-$C_6$alkyl which is optionally substituted with (=O) and a 4 to 6 membered heterocycloalkyl, —NHCH$_3$, or —N(CH$_3$)$_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_6$alkyl.

2. The compound of claim 1, or a pharmaceutically acceptable salt, solvate, isotopic variant, or N-oxide thereof, having the structure of Formula (Ia):

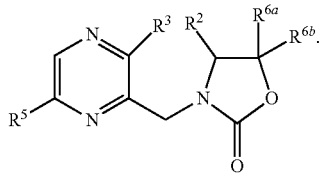

(Ia)

3. The compound of claim 1, or a pharmaceutically acceptable salt, solvate, isotopic variant, or N-oxide thereof, having the structure of Formula (Ib):

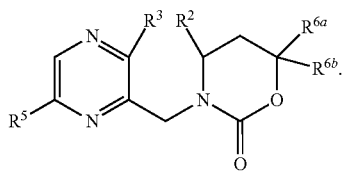

(Ib)

4. The compound of claim 1, or a pharmaceutically acceptable salt, solvate, isotopic variant, or N-oxide thereof, wherein $R^2$ is H or —CH$_3$.

5. The compound of claim 1, or a pharmaceutically acceptable salt, solvate, isotopic variant, or N-oxide thereof, wherein $R^2$ is other than H and the stereochemistry at the carbon to which $R^2$ is attached is (R).

6. The compound of claim 1, or a pharmaceutically acceptable salt, solvate, isotopic variant, or N-oxide thereof, wherein $R^2$ is other than H and the stereochemistry at the carbon to which $R^2$ is attached is (S).

7. The compound of claim 1, or a pharmaceutically acceptable salt, solvate, isotopic variant, or N-oxide thereof, wherein $R^3$ is H or —CH$_3$.

8. The compound of claim 1, or a pharmaceutically acceptable salt, solvate, isotopic variant, or N-oxide thereof, wherein $R^5$ is

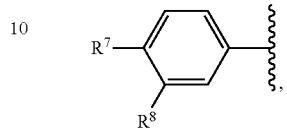

wherein $R^7$ is H or halogen, and $R^8$ is $C_1$-$C_6$haloalkyl or O—$C_1$-$C_6$haloalkyl.

9. The compound of claim 2, or a pharmaceutically acceptable salt, solvate, isotopic variant, or N-oxide thereof, having the structure of Formula (Ic):

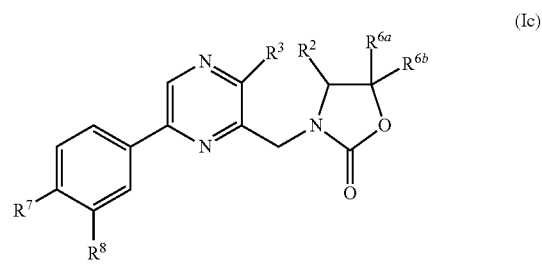

(Ic)

wherein $R^7$ is H or halogen, and $R^8$ is $C_1$-$C_6$haloalkyl or O—$C_1$-$C_6$haloalkyl.

10. The compound of claim 3, or a pharmaceutically acceptable salt, solvate, isotopic variant, or N-oxide thereof, having the structure of Formula (Id):

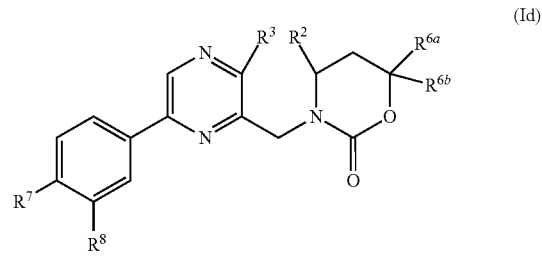

(Id)

wherein $R^7$ is H or halogen, and $R^8$ is $C_1$-$C_6$haloalkyl or O—$C_1$-$C_6$haloalkyl.

11. The compound of claim 8, or a pharmaceutically acceptable salt, solvate, isotopic variant, or N-oxide thereof, wherein $R^7$ is H, F, or Cl.

12. The compound of claim 8, or a pharmaceutically acceptable salt, solvate, isotopic variant, or N-oxide thereof, wherein $R^8$ is —CHF$_2$, —CF$_2$CH$_3$, or —OCHF$_2$.

13. The compound of claim 1, or a pharmaceutically acceptable salt, solvate, isotopic variant, or N-oxide thereof, wherein $R^5$ is:

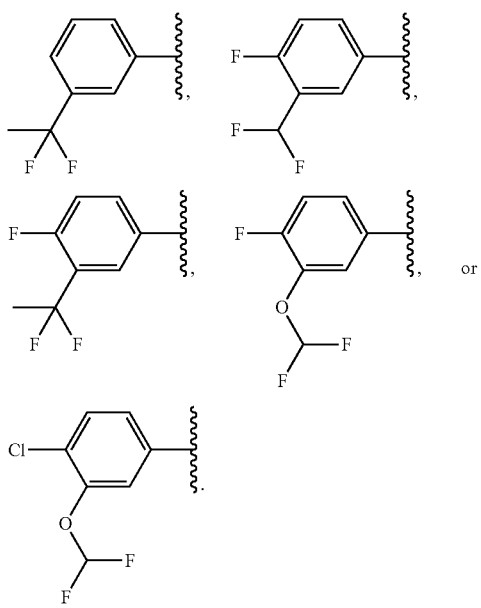

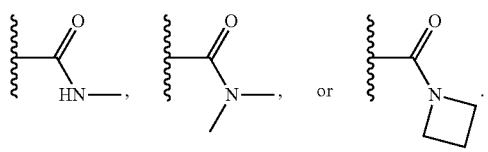

14. The compound of claim 1, or a pharmaceutically acceptable salt, solvate, isotopic variant, or N-oxide thereof, wherein $R^{6a}$ and $R^{6b}$ are both H.

15. The compound of claim 1, or a pharmaceutically acceptable salt, solvate, isotopic variant, or N-oxide thereof, wherein one of $R^{6a}$ and $R^{6b}$ is H and the other is $C_1$-$C_6$alkyl which is optionally substituted with (=O) and a 4 to 6 membered heterocycloalkyl, —NHCH$_3$, or —N(CH$_3$)$_2$; or $R^{6a}$ and $R^{6b}$ together with the carbon atom to which they are attached form (i) a $C_3$-$C_6$cycloalkyl ring or (ii) a 4 to 6 membered heterocycloalkyl ring which is optionally substituted with $C_1$-$C_6$alkyl.

16. The compound of claim 15, or a pharmaceutically acceptable salt, solvate, isotopic variant, or N-oxide thereof, wherein one of $R^{6a}$ and $R^{6b}$ is H and the other is —CH$_3$,

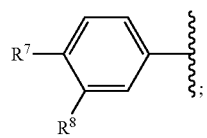

17. The compound of claim 1, or a pharmaceutically acceptable salt, solvate, isotopic variant, or N-oxide thereof, wherein $R^{6a}$ and $R^{6b}$ are both $C_1$-$C_6$alkyl.

18. The compound of claim 17, or a pharmaceutically acceptable salt, solvate, isotopic variant, or N-oxide thereof, wherein $R^{6a}$ and $R^{6b}$ are both —CH$_3$.

19. The compound of claim 1, or a pharmaceutically acceptable salt, solvate, isotopic variant, or N-oxide thereof, wherein $R^{6a}$ and $R^{6b}$ together with the carbon atom to which they are attached form a cyclopropyl ring.

20. The compound of claim 1, or a pharmaceutically acceptable salt, solvate, isotopic variant, or N-oxide thereof, wherein $R^{6a}$ and $R^{6b}$ together with the carbon atom to which they are attached is:

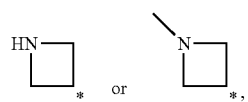

wherein * denotes the point of attachment of the ring to the remainder of the molecule.

21. The compound of claim 2, or a pharmaceutically acceptable salt, solvate, isotopic variant, or N-oxide thereof, wherein:
$R^2$ is H or —CH$_3$;
$R^3$ is H or —CH$_3$;
$R^5$ is

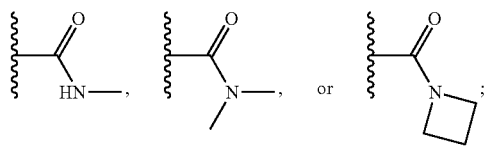

$R^{6a}$ and $R^{6b}$ are both H; or one of $R^{6a}$ and $R^{6b}$ is H and the other is —CH$_3$,

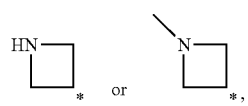

or $R^{6a}$ and $R^{6b}$ are both —CH$_3$; or $R^{6a}$ and $R^{6b}$ together with the carbon atom to which they are attached form a cyclopropyl ring,

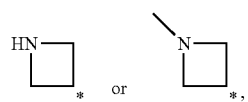

wherein * denotes the point of attachment of the ring to the remainder of the molecule;
$R^7$ is H, F, or Cl; and
$R^8$ is —CHF$_2$, —CF$_2$CH$_3$, or —OCHF$_2$.

22. The compound of claim 21, wherein one of $R^{6a}$ and $R^{6b}$ is H and the other is —CH$_3$.

23. The compound of claim 21, wherein $R^{6a}$ and $R^{6b}$ together with the carbon atom to which they are attached form a cyclopropyl ring.

24. The compound of claim 3, or a pharmaceutically acceptable salt, solvate, isotopic variant, or N-oxide thereof, wherein:
$R^2$ is H;
$R^3$ is H or —CH$_3$;
$R^5$ is

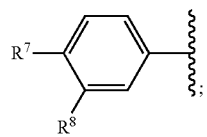

$R^{6a}$ and $R^{6b}$ are both H; or $R^{6a}$ and $R^{6b}$ together with the carbon atom to which they are attached form a cyclopropyl ring;
$R^7$ is H, F, or Cl; and
$R^8$ is —CHF$_2$, —CF$_2$CH$_3$, or —OCHF$_2$.

25. The compound of claim 21, wherein $R^5$ is

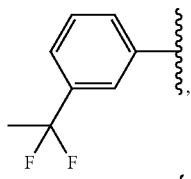 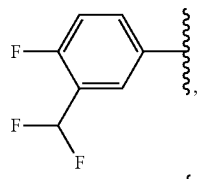

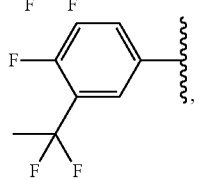 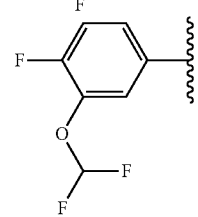

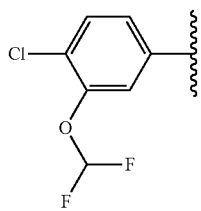  or

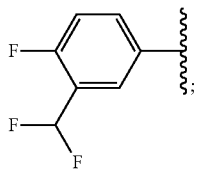 [SMILES: *c1ccc(F)c(C(F)F)c1]

26. The compound of claim 1, or a pharmaceutically acceptable salt, solvate, isotopic variant, or N-oxide thereof, wherein:
$R^2$ is H or C$_1$-C$_3$alkyl;
$R^3$ is H or C$_1$-C$_3$alkyl;
$R^5$ is

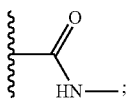

and
$R^{6a}$ and $R^{6b}$ are both H; or one of $R^{6a}$ and $R^{6b}$ is H and the other is or $R^{6a}$ and $R^{6b}$ together with the carbon atom to which they are attached form a cyclopropyl ring.

27. A compound, or a pharmaceutically acceptable salt, solvate, isotopic variant, or N-oxide thereof, wherein the compound is
3-[[6-[3-(Difluoromethyl)-4-fluoro-phenyl]pyrazin-2-yl]methyl]oxazolidin-2-one;
3-[[6-[3-(Difluoromethoxy)-4-fluoro-phenyl]pyrazin-2-yl]methyl]oxazolidin-2-one;
5-[[6-[3-(Difluoromethyl)-4-fluoro-phenyl]pyrazin-2-yl]methyl]-7-oxa-5-azaspiro[2.4]heptan-6-one;
3-[[6-[3-(Difluoromethyl)-4-fluoro-phenyl]pyrazin-2-yl]methyl]-5,5-dimethyl-oxazolidin-2-one;
(5R)-3-[[6-[3-(Difluoromethyl)-4-fluoro-phenyl]pyrazin-2-yl]methyl]-5-methyl-oxazolidin-2-one;
(5S)-3-[[6-[3-(Difluoromethyl)-4-fluoro-phenyl]pyrazin-2-yl]methyl]-5-methyl-oxazolidin-2-one;
(4R)-3-[[6-[3-(Difluoromethyl)-4-fluoro-phenyl]pyrazin-2-yl]methyl]-4-methyl-oxazolidin-2-one;
(4S)-3-[[6-[3-(Difluoromethyl)-4-fluoro-phenyl]pyrazin-2-yl]methyl]-4-methyl-oxazolidin-2-one;
3-[[6-[3-(Difluoromethyl)-4-fluoro-phenyl]pyrazin-2-yl]methyl]-1,3-oxazinan-2-one;
5-[[6-[3-(Difluoromethyl)-4-fluoro-phenyl]-3-methyl-pyrazin-2-yl]methyl]-7-oxa-5-azaspiro[2.4]heptan-6-one;
(4R)-3-[[6-[3-(Difluoromethyl)-4-fluoro-phenyl]-3-methyl-pyrazin-2-yl]methyl]-4-methyl-oxazolidin-2-one;
(4S)-3-[[6-[3-(Difluoromethyl)-4-fluoro-phenyl]-3-methyl-pyrazin-2-yl]methyl]-4-methyl-oxazolidin-2-one;
(5R)-3-[[6-[3-(Difluoromethyl)-4-fluoro-phenyl]-3-methyl-pyrazin-2-yl]methyl]-5-methyl-oxazolidin-2-one;
(5S)-3-[[6-[3-(Difluoromethyl)-4-fluoro-phenyl]-3-methyl-pyrazin-2-yl]methyl]-5-methyl-oxazolidin-2-one;
3-[[6-[3-(Difluoromethyl)-4-fluoro-phenyl]-3-methyl-pyrazin-2-yl]methyl]-1,3-oxazinan-2-one;
5-[[6-[3-(Difluoromethoxy)-4-fluoro-phenyl]pyrazin-2-yl]methyl]-7-oxa-5-azaspiro[2.4]heptan-6-one;
3-[[6-[3-(Difluoromethoxy)-4-fluoro-phenyl]pyrazin-2-yl]methyl]-5,5-dimethyl-oxazolidin-2-one;
(4R)-3-[[6-[3-(Difluoromethoxy)-4-fluoro-phenyl]pyrazin-2-yl]methyl]-4-methyl-oxazolidin-2-one;
(4S)-3-[[6-[3-(Difluoromethoxy)-4-fluoro-phenyl]pyrazin-2-yl]methyl]-4-methyl-oxazolidin-2-one;
(5R)-3-[[6-[3-(Difluoromethoxy)-4-fluoro-phenyl]pyrazin-2-yl]methyl]-5-methyl-oxazolidin-2-one;
(5S)-3-[[6-[3-(Difluoromethoxy)-4-fluoro-phenyl]pyrazin-2-yl]methyl]-5-methyl-oxazolidin-2-one;
3-[[6-[3-(Difluoromethoxy)-4-fluoro-phenyl]pyrazin-2-yl]methyl]-1,3-oxazinan-2-one;
5-[[6-[3-(Difluoromethoxy)-4-fluoro-phenyl]-3-methyl-pyrazin-2-yl]methyl]-7-oxa-5-azaspiro[2.4]heptan-6-one;
(4R)-3-[[6-[3-(Difluoromethoxy)-4-fluoro-phenyl]-3-methyl-pyrazin-2-yl]methyl]-4-methyl-oxazolidin-2-one;
(4S)-3-[[6-[3-(Difluoromethoxy)-4-fluoro-phenyl]-3-methyl-pyrazin-2-yl]methyl]-4-methyl-oxazolidin-2-one;
(5R)-3-[[6-[3-(Difluoromethoxy)-4-fluoro-phenyl]-3-methyl-pyrazin-2-yl]methyl]-5-methyl-oxazolidin-2-one;
(5S)-3-[[6-[3-(Difluoromethoxy)-4-fluoro-phenyl]-3-methyl-pyrazin-2-yl]methyl]-5-methyl-oxazolidin-2-one;
3-[[6-[3-(Difluoromethoxy)-4-fluoro-phenyl]-3-methyl-pyrazin-2-yl]methyl]-1,3-oxazinan-2-one;
5-[[6-[4-Chloro-3-(difluoromethoxy)phenyl]pyrazin-2-yl]methyl]-7-oxa-5-azaspiro[2.4]heptan-6-one;
3-[[6-[4-Chloro-3-(difluoromethoxy)phenyl]pyrazin-2-yl]methyl]-5,5-dimethyl-oxazolidin-2-one;
(5R)-3-[[6-[4-Chloro-3-(difluoromethoxy)phenyl]pyrazin-2-yl]methyl]-5-methyl-oxazolidin-2-one;

(5S)-3-[[6-[4-Chloro-3-(difluoromethoxy)phenyl]
pyrazin-2-yl]methyl]-5-methyl-oxazolidin-2-one;
(4R)-3-[[6-[4-Chloro-3-(difluoromethoxy)phenyl]
pyrazin-2-yl]methyl]-4-methyl-oxazolidin-2-one;
(4S)-3-[[6-[4-Chloro-3-(difluoromethoxy)phenyl]
pyrazin-2-yl]methyl]-4-methyl-oxazolidin-2-one;
3-[[6-[4-Chloro-3-(difluoromethoxy)phenyl]pyrazin-2-
yl]methyl]-1,3-oxazinan-2-one;
5-[[6-[4-Chloro-3-(difluoromethoxy)phenyl]-3-methyl-
pyrazin-2-yl]methyl]-7-oxa-5-azaspiro[2.4]heptan-6-
one;
3-[[6-[4-Chloro-3-(difluoromethoxy)phenyl]-3-methyl-
pyrazin-2-yl]methyl]-1,3-oxazinan-2-one;
5-[[6-[3-(1,1-Difluoroethyl)phenyl]pyrazin-2-yl]methyl]-
7-oxa-5-azaspiro[2.4]heptan-6-one;
3-[[6-[3-(1,1-Difluoroethyl)phenyl]pyrazin-2-yl]methyl]-
5,5-dimethyl-oxazolidin-2-one;
(5R)-3-[[6-[3-(1,1-Difluoroethyl)phenyl]pyrazin-2-yl]
methyl]-5-methyl-oxazolidin-2-one;
(5S)-3-[[6-[3-(1,1-Difluoroethyl)phenyl]pyrazin-2-yl]
methyl]-5-methyl-oxazolidin-2-one;
3-[[6-[3-(1,1-Difluoroethyl)phenyl]pyrazin-2-yl]methyl]-
1,3-oxazinan-2-one;
5-[[6-[3-(1,1-Difluoroethyl)phenyl]-3-methyl-pyrazin-2-
yl]methyl]-7-oxa-5-azaspiro[2.4]heptan-6-one;
3-[[6-[3-(1,1-Difluoroethyl)phenyl]-3-methyl-pyrazin-2-
yl]methyl]-5,5-dimethyl-oxazolidin-2-one;
3-[[6-[3-(1,1-Difluoroethyl)phenyl]-3-methyl-pyrazin-2-
yl]methyl]-1,3-oxazinan-2-one;
(4R)-3-[[6-[3-(1,1-Difluoroethyl)-4-fluoro-phenyl]
pyrazin-2-yl]methyl]-4-methyl-oxazolidin-2-one;
(4S)-3-[[6-[3-(1,1-Difluoroethyl)-4-fluoro-phenyl]
pyrazin-2-yl]methyl]-4-methyl-oxazolidin-2-one;
6-[[6-[3-(1,1-Difluoroethyl)phenyl]pyrazin-2-yl]methyl]-
8-oxa-6-azaspiro[2.5]octan-7-one;
6-[[6-[3-(Difluoromethoxy)-4-fluoro-phenyl]pyrazin-2-
yl]methyl]-8-oxa-6-azaspiro[2.5]octan-7-one;
6-[[6-[4-Chloro-3-(difluoromethoxy)phenyl]pyrazin-2-
yl]methyl]-8-oxa-6-azaspiro[2.5]octan-7-one;
6-[[6-[4-Chloro-3-(difluoromethoxy)phenyl]-3-methyl-
pyrazin-2-yl]methyl]-8-oxa-6-azaspiro[2.5]octan-7-
one;
6-[[6-[3-(Difluoromethyl)-4-fluoro-phenyl]pyrazin-2-yl]
methyl]-8-oxa-6-azaspiro[2.5]octan-7-one;
6-[[6-[3-(Difluoromethyl)-4-fluoro-phenyl]-3-methyl-
pyrazin-2-yl]methyl]-8-oxa-6-azaspiro[2.5]octan-7-
one;
6-[[6-[3-(Difluoromethoxy)-4-fluoro-phenyl]-3-methyl-
pyrazin-2-yl]methyl]-8-oxa-6-azaspiro[2.5]octan-7-
one;
(R/S)-3-[[6-[4-Chloro-3-(difluoromethoxy)phenyl]
pyrazin-2-yl]methyl]-N,N-dimethyl-2-oxo-oxazoli-
dine-5-carboxamide;
(R/S)-3-[[6-[4-Chloro-3-(difluoromethoxy)phenyl]
pyrazin-2-yl]methyl]-N-methyl-2-oxo-oxazolidine-5-
carboxamide;
5-(Azetidine-1-carbonyl)-3-[[6-[4-chloro-3-(difluo-
romethoxy)phenyl]pyrazin-2-yl]methyl]oxazolidin-2-
one;
(R/S)-5-(Azetidine-1-carbonyl)-3-[[6-[3-(difluorom-
ethyl)-4-fluoro-phenyl]pyrazin-2-yl]methyl]oxazoli-
din-2-one;
(R/S)-3-[[6-[3-(Difluoromethyl)-4-fluoro-phenyl]
pyrazin-2-yl]methyl]-N-methyl-2-oxo-oxazolidine-5-
carboxamide;

(R/S)-3-[[6-[3-(Difluoromethoxy)-4-fluoro-phenyl]
pyrazin-2-yl]methyl]-N-methyl-2-oxo-oxazolidine-5-
carboxamide;
(R/S)-5-(Azetidine-1-carbonyl)-3-[[6-[3-(difluo-
romethoxy)-4-fluoro-phenyl]pyrazin-2-yl]methyl]oxa-
zolidin-2-one;
(R/S)-3-[[6-[3-(1,1-Difluoroethyl)-4-fluoro-phenyl]
pyrazin-2-yl]methyl]-N,N-dimethyl-2-oxo-oxazoli-
dine-5-carboxamide;
(R/S)-3-[[6-[3-(1,1-Difluoroethyl)-4-fluoro-phenyl]
pyrazin-2-yl]methyl]-N-methyl-2-oxo-oxazolidine-5-
carboxamide;
(R/S)-5-(Azetidine-1-carbonyl)-3-[[6-[3-(1,1-difluoro-
ethyl)-4-fluoro-phenyl]pyrazin-2-yl]methyl]oxazoli-
din-2-one;
(R/S)-3-[[6-[3-(Difluoromethyl)-4-fluoro-phenyl]
pyrazin-2-yl]methyl]-N,N-dimethyl-2-oxo-oxazoli-
dine-5-carboxamide;
(R/S)-3-[[6-[3-(Difluoromethoxy)-4-fluoro-phenyl]
pyrazin-2-yl]methyl]-N,N-dimethyl-2-oxo-oxazoli-
dine-5-carboxamide;
6-[[6-[4-Chloro-3-(difluoromethoxy)phenyl]pyrazin-2-
yl]methyl]-8-oxa-2,6-diazaspiro[3.4]octan-7-one; or
6-[[6-[4-Chloro-3-(difluoromethoxy)phenyl]pyrazin-2-
yl]methyl]-2-methyl-8-oxa-2,6-diazaspiro[3.4]octan-
7-one.

28. A compound, or a pharmaceutically acceptable salt, solvate, isotopic variant, or N-oxide thereof, wherein the compound is 5-[[6-[3-(Difluoromethyl)-4-fluoro-phenyl]pyrazin-2-yl]
methyl]-7-oxa-5-azaspiro[2.4]heptan-6-one;
3-[[6-[3-(Difluoromethoxy)-4-fluoro-phenyl]pyrazin-2-
yl]methyl]-1,3-oxazinan-2-one;
5-[[6-[4-Chloro-3-(difluoromethoxy)phenyl]pyrazin-2-
yl]methyl]-7-oxa-5-azaspiro[2.4]heptan-6-one;
3-[[6-[4-Chloro-3-(difluoromethoxy)phenyl]pyrazin-2-
yl]methyl]-1,3-oxazinan-2-one; or
3-[[6-[3-(Difluoromethoxy)-4-fluoro-phenyl]-3-methyl-
pyrazin-2-yl]methyl]-1,3-oxazinan-2-one.

29. A pharmaceutical composition comprising: (A) the compound of claim 1, or a pharmaceutically acceptable salt, solvate, isotopic variant, or N-oxide thereof, and (B) at least one pharmaceutically acceptable excipient.

30. A method of treating a subject suffering from or diagnosed with a disease, disorder, or medical condition mediated by GluN2B receptor activity, comprising administering to the subject a therapeutically effective amount of the compound of claim 1, or a pharmaceutically acceptable salt, solvate, isotopic variant, or N-oxide thereof.

31. The method of claim 30, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

32. The method of claim 31, wherein the disease, disorder or medical condition mediated by GluN2B receptor activity comprises bipolar disorder, a mood disorder, treatment resistant depression, major depressive disorder, or epilepsy.

* * * * *